(12) United States Patent  (10) Patent No.: US 7,658,196 B2
Ferreri et al.  (45) Date of Patent: Feb. 9, 2010

(54) SYSTEM AND METHOD FOR DETERMINING IMPLANTED DEVICE ORIENTATION

(75) Inventors: Annie L. Ferreri, Loveland, OH (US); Daniel F. Dlugos, Middletown, OH (US); David N. Plescia, Cincinnati, OH (US); William L. Hassler, Jr., Carlsbad, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 285 days.

(21) Appl. No.: 11/739,778

(22) Filed: Apr. 25, 2007

(65) Prior Publication Data

US 2007/0213837 A1  Sep. 13, 2007

Related U.S. Application Data

(63) Continuation-in-part of application No. 11/369,682, filed on Mar. 7, 2006, which is a continuation-in-part of application No. 11/065,410, filed on Feb. 24, 2005.

(51) Int. Cl.
*A61B 19/00* (2006.01)
(52) U.S. Cl. .......................................... 128/899; 600/37
(58) Field of Classification Search ......... 128/897–899; 600/29–32, 37, 593; 604/27–28, 909; 606/139–141, 606/151, 157, 201–203, 213, 228; 607/41
See application file for complete search history.

(56) References Cited

U.S. PATENT DOCUMENTS

| | | |
|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |

(Continued)

FOREIGN PATENT DOCUMENTS

AU  729 467  2/2001

(Continued)

OTHER PUBLICATIONS

EPO Search Report dated Jul. 12, 2007, for EP Application No. 07250931.8.

(Continued)

*Primary Examiner*—John P Lacyk
(74) *Attorney, Agent, or Firm*—Frost Brown Todd LLC

(57) ABSTRACT

A system is operable to detect the orientation of an implant component. The system comprises an implantable component, an external component, and a logic component. The implantable component comprises a first coil operable to transmit a first signal having a phase. The external component comprises a second coil operable to transmit a second signal having a phase. The logic component is operable to compare the phase of the first signal with the phase of the second signal. The logic component is further configured to determine an orientation of the first coil relative to the second coil based on a comparison of the phase of the first signal with the phase of the second signal. The system may be used to determine the orientation of an injection port in an implanted gastric band system. The system may alternatively be used in a variety of other types of systems.

17 Claims, 17 Drawing Sheets

U.S. PATENT DOCUMENTS

| | | |
|---|---|---|
| 322,388 A | 7/1885 | Lord |
| 400,401 A | 3/1889 | Gutzkow |
| D23,637 S | 9/1894 | Casad et al. |
| D24,900 S | 11/1895 | Clemecet |
| D25,318 S | 3/1896 | Perkey |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |
| 953,875 A | 4/1910 | Waring |
| 991,192 A | 5/1911 | Battenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff et al. |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,178,463 A | 10/1939 | Bahnson |
| 2,180,599 A | 11/1939 | Menasco |
| 2,177,564 A | 12/1939 | Havill |
| 2,203,460 A | 6/1940 | Fieber |
| 2,206,038 A | 7/1940 | Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,396,351 A | 3/1946 | Thompson |
| 2,426,392 A | 8/1947 | Fennema |
| 2,426,817 A | 9/1947 | Carlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |

| | | | | | |
|---|---|---|---|---|---|
| 3,070,373 A | 12/1962 | Mathews et al. | 3,399,667 A | 9/1968 | Nishimoto et al. |
| 3,082,414 A | 3/1963 | Papaminas | 3,400,734 A | 9/1968 | Rosenberg |
| 3,085,577 A | 4/1963 | Berman et al. | 3,403,237 A | 9/1968 | Wysong |
| 3,096,410 A | 7/1963 | Anderson | 3,409,924 A | 11/1968 | Slama |
| 3,099,262 A | 7/1963 | Bigliano | 3,411,347 A | 11/1968 | Wirth et al. |
| 3,125,028 A | 3/1964 | Rohde | 3,417,476 A | 12/1968 | Martens |
| 3,126,029 A | 3/1964 | Englesson | 3,420,325 A | 1/1969 | McAlister et al. |
| 3,129,072 A | 4/1964 | Cook et al. | 3,422,324 A | 1/1969 | Webb |
| 3,135,914 A | 6/1964 | Callan et al. | 3,426,165 A | 2/1969 | Beaman |
| 3,144,017 A | 8/1964 | Muth | 3,438,391 A | 4/1969 | Yocum |
| 3,151,258 A | 9/1964 | Sonderegger et al. | 3,443,608 A | 5/1969 | Copping et al. |
| 3,153,460 A | 10/1964 | Raskin | 3,445,335 A | 5/1969 | Gluntz |
| 3,161,051 A | 12/1964 | Perry, Jr. | 3,447,281 A | 6/1969 | Bufford et al. |
| 3,167,044 A | 1/1965 | Henrickson | 3,450,153 A | 6/1969 | Hildebrandt et al. |
| 3,171,549 A | 3/1965 | Orloff | 3,453,546 A | 7/1969 | Fryer |
| 3,172,700 A | 3/1965 | Haas | 3,453,848 A | 7/1969 | Williamson |
| 3,173,269 A | 3/1965 | Imbertson | 3,456,134 A | 7/1969 | Ko |
| 3,182,494 A | 5/1965 | Beatty et al. | 3,457,909 A | 7/1969 | Laird |
| 3,187,181 A | 6/1965 | Keller | 3,460,557 A | 8/1969 | Gallant |
| 3,187,745 A | 6/1965 | Baum et al. | 3,463,338 A | 8/1969 | Schneider |
| 3,190,388 A | 6/1965 | Moser et al. | 3,469,818 A | 9/1969 | Cowan |
| 3,205,547 A | 9/1965 | Riekse | 3,470,725 A | 10/1969 | Brown et al. |
| 3,208,255 A | 9/1965 | Burk | 3,472,230 A | 10/1969 | Fogarty |
| 3,209,570 A | 10/1965 | Hills | 3,478,344 A | 11/1969 | Schwitzgebel et al. |
| 3,221,468 A | 12/1965 | Casey | 3,482,449 A | 12/1969 | Werner |
| 3,228,703 A | 1/1966 | Wilson | 3,482,816 A | 12/1969 | Arnold |
| 3,229,684 A | 1/1966 | Nagumo et al. | 3,487,959 A | 1/1970 | Pearne et al. |
| 3,236,088 A | 2/1966 | Moller | 3,491,842 A | 1/1970 | Delacour et al. |
| 3,238,624 A | 3/1966 | McCabe | 3,492,638 A | 1/1970 | Lane |
| 3,240,510 A | 3/1966 | Spouge | 3,502,829 A | 3/1970 | Reynolds |
| 3,245,642 A | 4/1966 | Dicke | 3,503,116 A | 3/1970 | Strack |
| 3,255,568 A | 6/1966 | Martin et al. | 3,504,664 A | 4/1970 | Haddad |
| 3,260,091 A | 7/1966 | Shaw, Jr. | 3,505,808 A | 4/1970 | Eschle |
| 3,265,822 A | 8/1966 | Moulten | 3,509,754 A | 5/1970 | Massingill et al. |
| 3,266,489 A | 8/1966 | Watkins et al. | 3,512,517 A | 5/1970 | Kadish et al. |
| 3,273,447 A | 9/1966 | Frank | 3,514,919 A | 6/1970 | Ashton et al. |
| 3,283,352 A | 11/1966 | Hu | 3,516,220 A | 6/1970 | Buford et al. |
| 3,290,919 A | 12/1966 | Malinak et al. | 3,517,553 A | 6/1970 | Williams et al. |
| 3,292,493 A | 12/1966 | Franklin | 3,527,226 A | 9/1970 | Hakin et al. |
| 3,292,888 A | 12/1966 | Fischer | 3,529,908 A | 9/1970 | Smith |
| 3,294,988 A | 12/1966 | Packard | 3,530,449 A | 9/1970 | Anderson |
| 3,299,603 A | 1/1967 | Shaw | 3,533,403 A | 10/1970 | Woodson |
| 3,299,882 A | 1/1967 | Masino | 3,534,728 A | 10/1970 | Barrows |
| 3,301,514 A | 1/1967 | Sugaya | 3,534,872 A | 10/1970 | Roth et al. |
| 3,302,457 A | 2/1967 | Mayes | 3,535,914 A | 10/1970 | Veith et al. |
| 3,306,384 A | 2/1967 | Ross | 3,539,009 A | 11/1970 | Kudlkaty |
| 3,313,314 A | 4/1967 | Burke et al. | 3,543,744 A | 12/1970 | LePar |
| 3,316,935 A | 5/1967 | Kaiser et al. | 3,545,275 A | 12/1970 | Harrison et al. |
| 3,320,750 A | 5/1967 | Haise et al. | 3,550,583 A | 12/1970 | Chiku |
| 3,321,035 A | 5/1967 | Tarpley | 3,550,847 A | 12/1970 | Scott |
| 3,332,788 A | 7/1967 | Barnby | 3,563,094 A | 2/1971 | Rieschel |
| 3,334,510 A | 8/1967 | Hallesy | 3,563,245 A | 2/1971 | McLean et al. |
| 3,339,401 A | 9/1967 | Peters | 3,566,083 A | 2/1971 | McMillin |
| 3,340,868 A | 9/1967 | Darling | 3,566,875 A | 3/1971 | Stoehr |
| 3,347,162 A | 10/1967 | Braznell | 3,568,367 A | 3/1971 | Myers |
| 3,350,944 A | 11/1967 | De Michele | 3,568,636 A | 3/1971 | Lockwood |
| 3,353,364 A | 11/1967 | Blanding et al. | 3,576,554 A | 4/1971 | Temps, Jr. et al. |
| 3,353,481 A | 11/1967 | Antonucci | 3,580,082 A | 5/1971 | Strack |
| 3,356,334 A | 12/1967 | Scaramucci | 3,581,402 A | 6/1971 | London et al. |
| 3,356,510 A | 12/1967 | Barnby | 3,583,387 A | 6/1971 | Garner et al. |
| 3,357,218 A | 12/1967 | Mitchell | 3,587,204 A | 6/1971 | George |
| 3,357,461 A | 12/1967 | Friendship | 3,590,809 A | 7/1971 | London |
| 3,359,741 A | 12/1967 | Nelson | 3,590,818 A | 7/1971 | Lemole |
| 3,361,300 A | 1/1968 | Kaplan | 3,590,992 A | 7/1971 | Soderstrom et al. |
| 3,364,929 A | 1/1968 | Ide et al. | 3,592,183 A | 7/1971 | Watkins et al. |
| 3,365,684 A | 1/1968 | Stemke | 3,594,519 A | 7/1971 | Schmidlin |
| 3,378,456 A | 4/1968 | Roberts | 3,602,885 A | 8/1971 | Grajeda |
| 3,380,445 A | 4/1968 | Frasier | 3,610,016 A | 10/1971 | Bultman |
| 3,380,649 A | 4/1968 | Roberts | 3,610,851 A | 10/1971 | Krupski |
| 3,385,022 A | 5/1968 | Anderson | 3,611,811 A | 10/1971 | Lissau |
| 3,389,355 A | 6/1968 | Schroeder, Jr. | 3,614,926 A | 10/1971 | Brechtel |
| 3,393,612 A | 7/1968 | Gorgens et al. | 3,614,955 A | 10/1971 | Mirowski et al. |
| 3,396,561 A | 8/1968 | Day | 3,619,742 A | 11/1971 | Rud, Jr. |

| | | | | | |
|---|---|---|---|---|---|
| 3,623,371 A | 11/1971 | Jullien-Davin | 3,833,238 A | 9/1974 | Liard et al. |
| 3,624,854 A | 12/1971 | Strong | 3,834,167 A | 9/1974 | Tabor |
| 3,630,242 A | 12/1971 | Schieser et al. | 3,834,739 A | 9/1974 | Abildgaard et al. |
| 3,631,847 A | 1/1972 | Hobbs, II | 3,835,523 A | 9/1974 | Stansfield et al. |
| 3,633,881 A | 1/1972 | Yurdin | 3,839,708 A | 10/1974 | Bredesen et al. |
| 3,635,061 A | 1/1972 | Rydell et al. | 3,842,483 A | 10/1974 | Cramer |
| 3,635,074 A | 1/1972 | Moos et al. | 3,842,668 A | 10/1974 | Lippke et al. |
| 3,638,496 A | 2/1972 | King | 3,845,664 A | 11/1974 | Perry, Jr. |
| 3,644,883 A | 2/1972 | Borman et al. | 3,845,751 A | 11/1974 | Runstetler |
| 3,648,687 A | 3/1972 | Ramsey, III | 3,845,757 A | 11/1974 | Weyer |
| 3,651,289 A | 3/1972 | Nagashima et al. | 3,847,434 A | 11/1974 | Weman et al. |
| 3,651,405 A | 3/1972 | Whitney et al. | 3,850,208 A | 11/1974 | Hamilton |
| 3,653,671 A | 4/1972 | Shipes | 3,853,117 A | 12/1974 | Murr |
| 3,659,615 A | 5/1972 | Enger | 3,854,469 A | 12/1974 | Giori et al. |
| 3,677,685 A | 7/1972 | Aoki et al. | 3,855,902 A | 12/1974 | Kirst et al. |
| 3,686,958 A | 8/1972 | Porter et al. | 3,857,399 A | 12/1974 | Zacouto et al. |
| 3,688,568 A | 9/1972 | Karper et al. | 3,857,452 A | 12/1974 | Hartman |
| 3,701,392 A | 10/1972 | Wirth et al. | 3,857,745 A | 12/1974 | Grausch et al. |
| 3,702,677 A | 11/1972 | Heffington | 3,858,581 A | 1/1975 | Kamen |
| 3,703,099 A | 11/1972 | Rouse et al. | 3,863,622 A | 2/1975 | Buuck |
| 3,712,138 A | 1/1973 | Alinari et al. | 3,863,933 A | 2/1975 | Tredway |
| 3,713,124 A | 1/1973 | Durland et al. | 3,867,950 A | 2/1975 | Fischell |
| 3,719,524 A | 3/1973 | Ripley et al. | 3,868,008 A | 2/1975 | Brumbaugh |
| 3,721,412 A | 3/1973 | Kindorf | 3,868,679 A | 2/1975 | Arneson |
| 3,723,247 A | 3/1973 | Leine et al. | 3,871,599 A | 3/1975 | Takada et al. |
| 3,724,000 A | 4/1973 | Eakman | 3,872,285 A | 3/1975 | Shum et al. |
| 3,727,463 A | 4/1973 | Intraub | 3,874,388 A | 4/1975 | King et al. |
| 3,727,615 A | 4/1973 | Lenzkes | 3,876,980 A | 4/1975 | Haemmig et al. |
| 3,730,174 A | 5/1973 | Madison | 3,878,908 A | 4/1975 | Andersson et al. |
| 3,730,560 A | 5/1973 | Abildgaard et al. | 3,881,528 A | 5/1975 | Mackenzie |
| 3,731,679 A | 5/1973 | Wilhelmson et al. | 3,886,948 A | 6/1975 | Hakim et al. |
| 3,731,681 A | 5/1973 | Blackshear et al. | 3,893,111 A | 7/1975 | Cotter |
| 3,732,731 A | 5/1973 | Fussell, Jr. | 3,893,451 A | 7/1975 | Durand et al. |
| 3,735,040 A | 5/1973 | Punt et al. | 3,895,681 A | 7/1975 | Griffin et al. |
| 3,736,930 A | 6/1973 | Georgi | 3,899,862 A | 8/1975 | Muys et al. |
| 3,738,356 A | 6/1973 | Workman | 3,904,234 A | 9/1975 | Hill et al. |
| 3,740,921 A | 6/1973 | Meyer et al. | 3,908,334 A | 9/1975 | Rychiger et al. |
| 3,746,111 A | 7/1973 | Berthiaume et al. | 3,908,461 A | 9/1975 | Turpen |
| 3,748,378 A | 7/1973 | Ballou. | 3,908,721 A | 9/1975 | McGahey et al. |
| 3,749,098 A | 7/1973 | De Bennetot et al. | 3,910,087 A | 10/1975 | Jones |
| 3,749,422 A | 7/1973 | Abildgaard et al. | 3,912,168 A | 10/1975 | Mullins et al. |
| 3,749,423 A | 7/1973 | Abildgaard et al. | 3,912,304 A | 10/1975 | Abildgaard et al. |
| 3,750,194 A | 8/1973 | Summers | 3,918,286 A | 11/1975 | Whitehead |
| 3,757,770 A | 9/1973 | Brayshaw et al. | 3,918,291 A | 11/1975 | Pauly et al. |
| 3,759,095 A | 9/1973 | Short, Jr. et al. | 3,920,965 A | 11/1975 | Sohrwardy et al. |
| 3,760,638 A | 9/1973 | Lawson et al. | 3,921,682 A | 11/1975 | McGahey et al. |
| 3,763,960 A | 10/1973 | John et al. | 3,922,951 A | 12/1975 | Linsinger et al. |
| 3,765,142 A | 10/1973 | Lindquist et al. | 3,923,060 A | 12/1975 | Ellinwood, Jr. |
| 3,765,494 A | 10/1973 | Kielman, Jr. | 3,924,635 A | 12/1975 | Hakim et al. |
| 3,769,156 A | 10/1973 | Brecy et al. | 3,928,980 A | 12/1975 | Ganzinotti et al. |
| 3,769,830 A | 11/1973 | Porter et al. | 3,929,175 A | 12/1975 | Coone |
| 3,774,243 A | 11/1973 | Ny et al. | 3,930,682 A | 1/1976 | Booth |
| 3,776,333 A | 12/1973 | Mathauser | 3,930,852 A | 1/1976 | Tanaka et al. |
| 3,778,051 A | 12/1973 | Allen et al. | 3,936,028 A | 2/1976 | Norton et al. |
| 3,780,578 A | 12/1973 | Sellman et al. | 3,939,823 A | 2/1976 | Kaye et al. |
| 3,781,902 A | 12/1973 | Shim et al. | 3,940,122 A | 2/1976 | Janzen |
| 3,783,585 A | 1/1974 | Hoyland et al. | 3,940,630 A | 2/1976 | Bergonz |
| 3,789,667 A | 2/1974 | Porter et al. | 3,942,299 A | 3/1976 | Bory et al. |
| 3,796,095 A | 3/1974 | Fussell, Jr. | 3,942,382 A | 3/1976 | Hok |
| 3,807,219 A | 4/1974 | Wallskog | 3,942,536 A | 3/1976 | Mirowski et al. |
| 3,811,429 A | 5/1974 | Fletcher et al. | 3,943,915 A | 3/1976 | Severson |
| 3,815,722 A | 6/1974 | Sessoms | 3,945,704 A | 3/1976 | Kraus et al. |
| 3,818,765 A | 6/1974 | Eriksen et al. | 3,946,613 A | 3/1976 | Silver |
| 3,820,400 A | 6/1974 | Russo | 3,946,615 A | 3/1976 | Hluchan |
| 3,820,795 A | 6/1974 | Taylor | 3,946,724 A | 3/1976 | La Balme et al. |
| 3,823,610 A | 7/1974 | Fussell, Jr. | 3,948,141 A | 4/1976 | Shinjo et al. |
| 3,825,065 A | 7/1974 | Lloyd et al. | 3,949,388 A | 4/1976 | Fuller |
| 3,825,963 A | 7/1974 | Abildgaard et al. | 3,953,289 A | 4/1976 | Costes et al. |
| 3,825,964 A | 7/1974 | Groswith, III et al. | 3,954,271 A | 5/1976 | Tredway, Sr. |
| 3,828,672 A | 8/1974 | Gazzola et al. | 3,958,558 A | 5/1976 | Dunphy et al. |
| 3,828,766 A | 8/1974 | Krasnow | 3,960,142 A | 6/1976 | Elliott et al. |
| 3,831,588 A | 8/1974 | Rindner | 3,961,425 A | 6/1976 | Swanson et al. |
| 3,831,942 A | 8/1974 | Del Mar | 3,961,646 A | 6/1976 | Schon |

| Patent No. | Date | Name | Patent No. | Date | Name |
|---|---|---|---|---|---|
| 3,962,895 A | 6/1976 | Rydell | 4,077,882 A | 3/1978 | Gangemi |
| 3,962,921 A | 6/1976 | Lips | 4,078,620 A | 3/1978 | Westlake et al. |
| 3,963,019 A | 6/1976 | Quandt | 4,080,653 A | 3/1978 | Barnes, Jr. et al. |
| 3,964,485 A | 6/1976 | Neumeier | 4,084,752 A | 4/1978 | Hagiwara et al. |
| 3,964,770 A | 6/1976 | Abildgaard et al. | 4,086,488 A | 4/1978 | Hill |
| 3,967,737 A | 7/1976 | Peralta et al. | 4,087,568 A | 5/1978 | Fay et al. |
| 3,968,473 A | 7/1976 | Patton et al. | 4,088,417 A | 5/1978 | Kosmowski |
| 3,968,594 A | 7/1976 | Kawakami | 4,089,329 A | 5/1978 | Couvillon, Jr. et al. |
| 3,972,320 A | 8/1976 | Kalman | 4,090,802 A | 5/1978 | Bilz et al. |
| 3,973,753 A | 8/1976 | Wheeler | 4,092,719 A | 5/1978 | Salmon et al. |
| 3,973,858 A | 8/1976 | Poisson et al. | 4,092,925 A | 6/1978 | Fromson |
| 3,974,655 A | 8/1976 | Halpern et al. | 4,096,866 A | 6/1978 | Fischell |
| 3,974,865 A | 8/1976 | Fenton et al. | 4,098,293 A | 7/1978 | Kramer et al. |
| 3,976,278 A | 8/1976 | Dye et al. | 4,103,496 A | 8/1978 | Colamussi et al. |
| 3,977,391 A | 8/1976 | Fleischmann | 4,106,370 A | 8/1978 | Kraus et al. |
| 3,980,871 A | 9/1976 | Lindstrom et al. | 4,107,689 A | 8/1978 | Jellinek |
| 3,982,571 A | 9/1976 | Fenton et al. | 4,107,995 A | 8/1978 | Ligman et al. |
| 3,983,948 A | 10/1976 | Jeter | 4,108,148 A | 8/1978 | Cannon, III |
| 3,985,133 A | 10/1976 | Jenkins et al. | 4,108,575 A | 8/1978 | Schal et al. |
| 3,987,860 A | 10/1976 | Jabsen | 4,109,148 A | 8/1978 | Jaulmes et al. |
| 3,989,005 A | 11/1976 | Bowler, Jr. et al. | 4,109,518 A | 8/1978 | Dooley et al. |
| 3,991,749 A | 11/1976 | Zent | 4,109,644 A | 8/1978 | Kojima |
| 3,992,948 A | 11/1976 | D'Antonio et al. | 4,111,056 A | 9/1978 | Mastromatteo |
| 3,993,149 A | 11/1976 | Harvey | 4,111,629 A | 9/1978 | Nussbaumer |
| 3,996,927 A | 12/1976 | Frank | 4,114,424 A | 9/1978 | Johnson |
| 3,996,962 A | 12/1976 | Sutherland | 4,114,603 A | 9/1978 | Wilkinson |
| 4,003,141 A | 1/1977 | Le Roy | 4,114,606 A | 9/1978 | Seylar |
| 4,005,282 A | 1/1977 | Jennings | 4,120,097 A | 10/1978 | Jeter |
| 4,005,593 A | 2/1977 | Goldberg | 4,120,134 A | 10/1978 | Scholle |
| 4,006,735 A | 2/1977 | Hittman et al. | 4,121,635 A | 10/1978 | Hansel |
| 4,009,375 A | 2/1977 | White et al. | 4,123,310 A | 10/1978 | Varon et al. |
| 4,009,591 A | 3/1977 | Hester | 4,124,023 A | 11/1978 | Fleischmann et al. |
| 4,010,449 A | 3/1977 | Faggin et al. | 4,127,110 A | 11/1978 | Bullara |
| 4,014,319 A | 3/1977 | Favre et al. | 4,130,169 A | 12/1978 | Denison |
| 4,014,321 A | 3/1977 | March | 4,131,596 A | 12/1978 | Allen |
| 4,016,764 A | 4/1977 | Rice | 4,133,355 A | 1/1979 | Mayer |
| 4,017,329 A | 4/1977 | Larson | 4,133,367 A | 1/1979 | Abell |
| 4,018,134 A | 4/1977 | Linsinger | 4,135,509 A | 1/1979 | Shannon |
| 4,022,190 A | 5/1977 | Meyer | 4,140,131 A | 2/1979 | Dutcher et al. |
| 4,024,864 A | 5/1977 | Davies et al. | 4,141,348 A | 2/1979 | Hittman |
| 4,025,912 A | 5/1977 | Rice | 4,141,349 A | 2/1979 | Ory et al. |
| 4,026,276 A | 5/1977 | Chubbuck | 4,143,661 A | 3/1979 | LaForge et al. |
| 4,027,661 A | 6/1977 | Lyon et al. | 4,146,029 A | 3/1979 | Ellinwood, Jr. |
| 4,031,899 A | 6/1977 | Renirie | 4,147,161 A | 4/1979 | Ikebe et al. |
| 4,036,775 A | 7/1977 | Trautvetter et al. | 4,148,096 A | 4/1979 | Haas et al. |
| 4,039,069 A | 8/1977 | Kwan et al. | 4,149,423 A | 4/1979 | Frosch et al. |
| 4,041,954 A | 8/1977 | Ohara et al. | 4,151,823 A | 5/1979 | Grosse et al. |
| 4,042,504 A | 8/1977 | Drori et al. | 4,153,085 A | 5/1979 | Adams |
| 4,045,345 A | 8/1977 | Drori et al. | 4,156,422 A | 5/1979 | Hildebrandt et al. |
| 4,047,296 A | 9/1977 | Ishida et al. | 4,160,448 A | 7/1979 | Jackson |
| 4,047,851 A | 9/1977 | Bender | 4,160,971 A | 7/1979 | Jones et al. |
| 4,048,494 A | 9/1977 | Liesting et al. | 4,166,469 A | 9/1979 | Littleford |
| 4,048,879 A | 9/1977 | Cox | 4,167,304 A | 9/1979 | Gelbke |
| 4,049,004 A | 9/1977 | Walters | 4,167,952 A | 9/1979 | Reinicke |
| 4,051,338 A | 9/1977 | Harris, III | 4,168,567 A | 9/1979 | Leguy et al. |
| 4,052,991 A | 10/1977 | Zacouto et al. | 4,170,280 A | 10/1979 | Schwarz |
| 4,055,074 A | 10/1977 | Thimons et al. | 4,171,218 A | 10/1979 | Hoshino et al. |
| 4,055,175 A | 10/1977 | Clemens et al. | 4,173,228 A | 11/1979 | Van Steenwyk et al. |
| 4,056,854 A | 11/1977 | Boretos et al. | 4,183,124 A | 1/1980 | Hoffman |
| 4,058,007 A | 11/1977 | Exner et al. | 4,183,247 A | 1/1980 | Allen et al. |
| 4,062,351 A | 12/1977 | Hastwell et al. | 4,185,641 A | 1/1980 | Minior et al. |
| 4,062,354 A | 12/1977 | Taylor et al. | 4,186,287 A | 1/1980 | Scott |
| 4,062,360 A | 12/1977 | Bentley | 4,186,749 A | 2/1980 | Fryer |
| 4,063,439 A | 12/1977 | Besson et al. | 4,186,751 A | 2/1980 | Fleischmann |
| 4,064,882 A | 12/1977 | Johnson et al. | 4,190,057 A | 2/1980 | Hill et al. |
| 4,070,239 A | 1/1978 | Bevilacqua | 4,191,004 A | 3/1980 | Gmuer et al. |
| 4,072,047 A | 2/1978 | Reismuller et al. | 4,191,187 A | 3/1980 | Wright et al. |
| 4,073,292 A | 2/1978 | Edelman | 4,192,192 A | 3/1980 | Schnell |
| 4,075,099 A | 2/1978 | Pelton et al. | 4,193,397 A | 3/1980 | Tucker et al. |
| 4,075,602 A | 2/1978 | Clothier | 4,204,547 A | 5/1980 | Allocca |
| 4,077,072 A | 3/1978 | Dezura | 4,206,755 A | 6/1980 | Klein et al. |
| 4,077,394 A | 3/1978 | McCurdy | 4,206,761 A | 6/1980 | Cosman et al. |
| 4,077,405 A | 3/1978 | Haerten et al. | 4,206,762 A | 6/1980 | Cosman et al. |

| | | | | | | |
|---|---|---|---|---|---|---|
| 4,207,903 A | 6/1980 | O'Neill | | 4,380,427 A | 4/1983 | Hehl et al. |
| 4,212,074 A | 7/1980 | Kuno et al. | | 4,385,636 A | 5/1983 | Cosman |
| 4,217,221 A | 8/1980 | Masso | | 4,386,422 A | 5/1983 | Mumby et al. |
| 4,217,588 A | 8/1980 | Freeny, Jr. | | 4,387,715 A | 6/1983 | Hakim et al. |
| 4,220,189 A | 9/1980 | Marquez | | 4,387,907 A | 6/1983 | Hiestand et al. |
| 4,221,219 A | 9/1980 | Tucker | | 4,392,368 A | 7/1983 | Folkesson et al. |
| 4,221,523 A | 9/1980 | Eberle | | 4,393,899 A | 7/1983 | Tsuji et al. |
| 4,223,837 A | 9/1980 | Gubbiotti | | 4,393,951 A | 7/1983 | Horst-Rudolf et al. |
| 4,226,124 A | 10/1980 | Kersten et al. | | 4,395,232 A | 7/1983 | Koch |
| 4,226,229 A | 10/1980 | Eckhart et al. | | 4,395,258 A | 7/1983 | Wang et al. |
| 4,227,533 A | 10/1980 | Godfrey | | 4,395,916 A | 8/1983 | Martin |
| 4,231,376 A | 11/1980 | Lyon et al. | | 4,398,983 A | 8/1983 | Suzuki et al. |
| 4,232,682 A | 11/1980 | Veth | | 4,399,705 A | 8/1983 | Weiger et al. |
| 4,237,900 A | 12/1980 | Schulman et al. | | 4,399,707 A | 8/1983 | Wamstad |
| 4,241,247 A | 12/1980 | Byrne et al. | | 4,399,809 A | 8/1983 | Baro et al. |
| 4,241,870 A | 12/1980 | Marcus | | 4,399,821 A | 8/1983 | Bowers |
| 4,245,593 A | 1/1981 | Stein | | 4,403,984 A | 9/1983 | Ash et al. |
| 4,246,877 A | 1/1981 | Kennedy | | 4,404,968 A | 9/1983 | Evans, Sr. |
| 4,247,850 A | 1/1981 | Marcus | | 4,404,974 A | 9/1983 | Titus |
| 4,248,238 A | 2/1981 | Joseph et al. | | 4,405,318 A | 9/1983 | Whitney et al. |
| 4,248,241 A | 2/1981 | Tacchi | | 4,407,125 A | 10/1983 | Parsons et al. |
| 4,256,094 A | 3/1981 | Kapp et al. | | 4,407,271 A | 10/1983 | Schiff |
| 4,256,118 A | 3/1981 | Nagel | | 4,407,296 A | 10/1983 | Anderson |
| 4,262,343 A | 4/1981 | Claycomb | | 4,407,326 A | 10/1983 | Wilhelm |
| 4,262,632 A | 4/1981 | Hanton et al. | | 4,408,597 A | 10/1983 | Tenney, Jr. |
| 4,265,241 A | 5/1981 | Portner et al. | | 4,415,071 A | 11/1983 | Butler et al. |
| 4,265,252 A | 5/1981 | Chubbuck et al. | | 4,416,282 A | 11/1983 | Saulson et al. |
| 4,271,018 A | 6/1981 | Drori et al. | | 4,418,899 A | 12/1983 | Zimmermann et al. |
| 4,273,070 A | 6/1981 | Hoefelmayr | | 4,419,393 A | 12/1983 | Hanson et al. |
| 4,274,444 A | 6/1981 | Ruyak | | 4,421,124 A | 12/1983 | Marshall |
| 4,275,600 A | 6/1981 | Turner et al. | | 4,421,505 A | 12/1983 | Schwartz |
| 4,275,913 A | 6/1981 | Marcus | | 4,424,720 A | 1/1984 | Bucchianeri |
| 4,278,540 A | 7/1981 | Drori et al. | | 4,428,228 A | 1/1984 | Banzhaf et al. |
| 4,280,036 A | 7/1981 | Fukatsu et al. | | 4,428,365 A | 1/1984 | Hakky |
| 4,280,775 A | 7/1981 | Wood | | 4,430,899 A | 2/1984 | Wessel |
| 4,281,666 A | 8/1981 | Cosman | | 4,431,009 A | 2/1984 | Marino, Jr. et al. |
| 4,281,667 A | 8/1981 | Cosman | | 4,431,365 A | 2/1984 | Sturtz, Jr. |
| 4,284,073 A | 8/1981 | Krause et al. | | 4,432,363 A | 2/1984 | Kakegawa et al. |
| 4,285,770 A | 8/1981 | Chi et al. | | 4,435,173 A | 3/1984 | Siposs et al. |
| 4,291,699 A | 9/1981 | Geddes et al. | | 4,439,186 A | 3/1984 | Kuhl et al. |
| 4,295,963 A | 10/1981 | Drori et al. | | 4,441,491 A | 4/1984 | Evans, Sr. |
| 4,297,927 A | 11/1981 | Kuroda et al. | | 4,441,501 A | 4/1984 | Parent |
| 4,303,075 A | 12/1981 | Heilman et al. | | 4,444,194 A | 4/1984 | Burcham |
| 4,305,402 A | 12/1981 | Katims | | 4,444,498 A | 4/1984 | Heinemann |
| 4,312,374 A | 1/1982 | Drori et al. | | 4,445,385 A | 5/1984 | Endo |
| 4,314,480 A | 2/1982 | Becker | | 4,446,711 A | 5/1984 | Valente |
| 4,316,693 A | 2/1982 | Baxter et al. | | 4,447,224 A | 5/1984 | DeCant, Jr. et al. |
| 4,325,387 A | 4/1982 | Helfer | | 4,449,493 A | 5/1984 | Kopec et al. |
| 4,327,804 A | 5/1982 | Reed | | 4,450,811 A | 5/1984 | Ichikawa |
| 4,328,654 A | 5/1982 | Van Ginkel et al. | | 4,450,946 A | 5/1984 | Olding et al. |
| 4,332,254 A | 6/1982 | Lundquist | | 4,451,033 A | 5/1984 | Nestegard |
| 4,332,255 A | 6/1982 | Hakim et al. | | 4,453,537 A | 6/1984 | Spitzer |
| 4,339,831 A | 7/1982 | Johnson | | 4,453,578 A | 6/1984 | Wilder |
| 4,342,218 A | 8/1982 | Fox | | 4,460,835 A | 7/1984 | Masuoka et al. |
| 4,342,308 A | 8/1982 | Trick | | 4,464,170 A | 8/1984 | Clemens et al. |
| 4,346,604 A | 8/1982 | Snook et al. | | 4,465,015 A | 8/1984 | Osta et al. |
| 4,347,851 A | 9/1982 | Jundanian | | 4,465,474 A | 8/1984 | Mardorf et al. |
| 4,350,647 A | 9/1982 | de la Cruz | | 4,466,290 A | 8/1984 | Frick |
| 4,350,970 A | 9/1982 | von Tomkewitsch et al. | | 4,468,172 A | 8/1984 | Dixon et al. |
| 4,351,037 A | 9/1982 | Scherbatskoy | | 4,468,762 A | 8/1984 | Jurgens et al. |
| 4,351,116 A | 9/1982 | Scott, Jr. | | 4,469,365 A | 9/1984 | Marcus et al. |
| 4,356,486 A | 10/1982 | Mount | | 4,471,182 A | 9/1984 | Wielgos et al. |
| 4,360,010 A | 11/1982 | Finney | | 4,471,786 A | 9/1984 | Inagaki et al. |
| 4,360,277 A | 11/1982 | Daniel et al. | | 4,473,067 A | 9/1984 | Schiff |
| 4,361,153 A | 11/1982 | Slocum et al. | | 4,473,078 A | 9/1984 | Angel |
| 4,363,236 A | 12/1982 | Meyers | | 4,476,721 A | 10/1984 | Hochreuther et al. |
| 4,364,276 A | 12/1982 | Schimazoe et al. | | 4,478,213 A | 10/1984 | Redding |
| 4,365,425 A | 12/1982 | Gotchel | | 4,478,538 A | 10/1984 | Kakino |
| 4,368,937 A | 1/1983 | Palombo et al. | | 4,483,196 A | 11/1984 | Kurtz et al. |
| 4,369,013 A | 1/1983 | Abildgaard et al. | | 4,484,135 A | 11/1984 | Ishihara et al. |
| 4,373,527 A | 2/1983 | Fischell | | 4,485,813 A | 12/1984 | Anderson et al. |
| 4,376,523 A | 3/1983 | Goyen et al. | | 4,489,916 A | 12/1984 | Stevens |
| 4,378,809 A | 4/1983 | Cosman | | 4,492,632 A | 1/1985 | Mattson |

| | | | | | |
|---|---|---|---|---|---|
| 4,494,411 A | 1/1985 | Koschke et al. | 4,614,137 A | 9/1986 | Jones |
| 4,494,950 A | 1/1985 | Fischell | 4,615,691 A | 10/1986 | Hakim et al. |
| 4,497,176 A | 2/1985 | Rubin et al. | 4,617,016 A | 10/1986 | Blomberg et al. |
| 4,497,201 A | 2/1985 | Allen et al. | 4,618,861 A | 10/1986 | Gettens et al. |
| 4,499,394 A | 2/1985 | Koal | 4,620,807 A | 11/1986 | Polit |
| 4,499,691 A | 2/1985 | Karazim et al. | 4,621,331 A | 11/1986 | Iwata |
| 4,499,750 A | 2/1985 | Gerber et al. | 4,622,871 A | 11/1986 | Van Sickle et al. |
| 4,503,678 A | 3/1985 | Wimbush | 4,626,462 A | 12/1986 | Kober et al. |
| 4,511,974 A | 4/1985 | Nakane et al. | 4,633,304 A | 12/1986 | Nagasaki et al. |
| 4,513,295 A | 4/1985 | Jones et al. | 4,633,878 A | 1/1987 | Bombardieri et al. |
| 4,515,004 A | 5/1985 | Jaenson | 4,635,182 A | 1/1987 | Hintz |
| 4,515,750 A | 5/1985 | Pardini et al. | 4,637,736 A | 1/1987 | Andeen et al. |
| 4,516,866 A | 5/1985 | Yamauchi et al. | 4,638,665 A | 1/1987 | Benson et al. |
| 4,518,637 A | 5/1985 | Takeda et al. | 4,644,246 A | 2/1987 | Knapen et al. |
| 4,519,401 A | 5/1985 | Ko et al. | 4,646,553 A | 3/1987 | Tufte et al. |
| 4,520,443 A | 5/1985 | Yuki et al. | 4,648,363 A | 3/1987 | Kronich |
| 4,522,213 A | 6/1985 | Wallroth et al. | 4,648,406 A | 3/1987 | Miller |
| 4,527,568 A | 7/1985 | Rickards et al. | 4,658,358 A | 4/1987 | Leach et al. |
| 4,529,401 A | 7/1985 | Leslie et al. | 4,658,760 A | 4/1987 | Zehuhr |
| 4,531,526 A | 7/1985 | Genest | 4,660,568 A | 4/1987 | Cosman |
| 4,531,936 A | 7/1985 | Gordon | 4,665,511 A | 5/1987 | Rodney et al. |
| 4,536,000 A | 8/1985 | Rohm et al. | 4,665,896 A | 5/1987 | LaForge et al. |
| 4,537,005 A | 8/1985 | Hoyland et al. | 4,669,484 A | 6/1987 | Masters |
| 4,537,129 A | 8/1985 | Heinemann et al. | 4,672,974 A | 6/1987 | Lee |
| 4,538,616 A | 9/1985 | Rogoff | 4,674,457 A | 6/1987 | Berger et al. |
| 4,540,404 A | 9/1985 | Wolvek | 4,674,546 A | 6/1987 | Fournier et al. |
| 4,542,461 A | 9/1985 | Eldridge et al. | 4,678,408 A | 7/1987 | Nason et al. |
| 4,544,369 A | 10/1985 | Skakoon et al. | 4,681,559 A | 7/1987 | Hooven |
| 4,545,185 A | 10/1985 | Chikatani | 4,683,850 A | 8/1987 | Bauder et al. |
| 4,546,524 A | 10/1985 | Kreft | 4,685,463 A | 8/1987 | Williams |
| 4,548,209 A | 10/1985 | Wielders et al. | 4,685,469 A | 8/1987 | Keller et al. |
| 4,551,128 A | 11/1985 | Hakim et al. | 4,685,903 A | 8/1987 | Cable et al. |
| 4,552,150 A | 11/1985 | Zacouto et al. | 4,686,979 A | 8/1987 | Gruen et al. |
| 4,553,226 A | 11/1985 | Scherbatskoy | 4,686,987 A | 8/1987 | Salo et al. |
| 4,556,063 A | 12/1985 | Thompson et al. | 4,687,530 A | 8/1987 | Berscheid et al. |
| 4,556,086 A | 12/1985 | Raines | 4,691,694 A | 9/1987 | Boyd et al. |
| 4,557,269 A | 12/1985 | Reynolds et al. | 4,691,710 A | 9/1987 | Dickens et al. |
| 4,557,332 A | 12/1985 | Denison et al. | 4,693,253 A | 9/1987 | Adams |
| 4,559,815 A | 12/1985 | Needham et al. | 4,695,237 A | 9/1987 | Inaba et al. |
| 4,560,979 A | 12/1985 | Rosskopf et al. | 4,696,189 A | 9/1987 | Hochreuther et al. |
| 4,561,442 A | 12/1985 | Vollmann et al. | 4,697,574 A | 10/1987 | Karcher et al. |
| 4,562,751 A | 1/1986 | Nason et al. | 4,698,038 A | 10/1987 | Key et al. |
| 4,563,175 A | 1/1986 | LaFond | 4,700,497 A | 10/1987 | Sato et al. |
| 4,565,116 A | 1/1986 | Hehl | 4,700,610 A | 10/1987 | Bauer et al. |
| 4,566,456 A | 1/1986 | Koning et al. | 4,701,143 A | 10/1987 | Key et al. |
| 4,569,623 A | 2/1986 | Goldmann | 4,703,756 A | 11/1987 | Gough et al. |
| 4,570,351 A | 2/1986 | Szanto et al. | 4,705,507 A | 11/1987 | Boyles |
| 4,571,161 A | 2/1986 | Leblanc et al. | 4,706,948 A | 11/1987 | Kroecher et al. |
| 4,571,749 A | 2/1986 | Fischell | 4,711,249 A | 12/1987 | Brooks |
| 4,571,995 A | 2/1986 | Timme | 4,712,562 A | 12/1987 | Ohayon et al. |
| 4,573,835 A | 3/1986 | Eckardt et al. | 4,718,425 A | 1/1988 | Tanaka et al. |
| 4,574,792 A | 3/1986 | Trick | 4,722,348 A | 2/1988 | Ligtenberg et al. |
| 4,576,181 A | 3/1986 | Wallace et al. | 4,724,806 A | 2/1988 | Hartwig et al. |
| 4,576,183 A | 3/1986 | Plicchi et al. | 4,724,830 A | 2/1988 | Fischell |
| 4,577,512 A | 3/1986 | Lowenheck et al. | 4,725,826 A | 2/1988 | Hunter |
| 4,581,018 A | 4/1986 | Jassawalla et al. | 4,727,887 A | 3/1988 | Haber |
| 4,581,915 A | 4/1986 | Haulsee et al. | 4,728,479 A | 3/1988 | Merkovsky |
| 4,587,840 A | 5/1986 | Dobler et al. | 4,729,517 A | 3/1988 | Krokor et al. |
| 4,589,805 A | 5/1986 | Duffner et al. | 4,730,188 A | 3/1988 | Milheiser |
| 4,592,339 A | 6/1986 | Kuzmak et al. | 4,730,420 A | 3/1988 | Stratmann et al. |
| 4,592,340 A | 6/1986 | Boyles | 4,730,619 A | 3/1988 | Koning et al. |
| 4,593,703 A | 6/1986 | Cosman | 4,731,058 A | 3/1988 | Doan |
| 4,595,228 A | 6/1986 | Chu | 4,735,205 A | 4/1988 | Chachques et al. |
| 4,595,390 A | 6/1986 | Hakim et al. | 4,738,267 A | 4/1988 | Lazorthes et al. |
| 4,596,563 A | 6/1986 | Pande | 4,738,268 A | 4/1988 | Kipnis |
| 4,599,943 A | 7/1986 | Kobler et al. | 4,741,345 A | 5/1988 | Matthews et al. |
| 4,600,855 A | 7/1986 | Strachan et al. | 4,741,732 A | 5/1988 | Crankshaw et al. |
| 4,602,541 A | 7/1986 | Benzinger et al. | 4,743,129 A | 5/1988 | Keryhuel et al. |
| 4,604,089 A | 8/1986 | Santangelo et al. | 4,745,541 A | 5/1988 | Vaniglia et al. |
| 4,605,354 A | 8/1986 | Daly | 4,746,830 A | 5/1988 | Holland |
| 4,606,419 A | 8/1986 | Perini | 4,750,495 A | 6/1988 | Moore et al. |
| 4,606,478 A | 8/1986 | Hack et al. | 4,752,115 A | 6/1988 | Murray, Jr. et al. |
| 4,610,256 A | 9/1986 | Wallace | 4,752,658 A | 6/1988 | Mack |

| | | | | | | |
|---|---|---|---|---|---|---|
| 4,757,463 A | 7/1988 | Ballou et al. | | 4,905,698 A * | 3/1990 | Strohl et al. ................ 600/424 |
| 4,759,386 A | 7/1988 | Grouw, III | | 4,909,678 A | 3/1990 | Kakimoto et al. |
| 4,763,649 A | 8/1988 | Merrick | | 4,913,147 A | 4/1990 | Fahlstrom et al. |
| 4,765,001 A | 8/1988 | Smith | | 4,919,143 A | 4/1990 | Ayers |
| 4,767,406 A | 8/1988 | Wadham et al. | | 4,924,872 A | 5/1990 | Frank |
| 4,769,001 A | 9/1988 | Prince | | 4,926,903 A | 5/1990 | Kawai et al. |
| 4,772,257 A | 9/1988 | Hakim et al. | | 4,932,406 A | 6/1990 | Berkovits |
| 4,772,896 A | 9/1988 | Nakatsu et al. | | 4,934,369 A | 6/1990 | Maxwell |
| 4,773,401 A | 9/1988 | Citak et al. | | 4,936,304 A | 6/1990 | Kresh et al. |
| 4,774,950 A | 10/1988 | Cohen | | 4,940,037 A | 7/1990 | Eckert et al. |
| 4,774,955 A | 10/1988 | Jones | | 4,941,718 A | 7/1990 | Alexander, III et al. |
| 4,777,953 A | 10/1988 | Ash et al. | | 4,942,004 A | 7/1990 | Catanzaro |
| 4,779,626 A | 10/1988 | Peel et al. | | 4,944,050 A | 7/1990 | Shames et al. |
| 4,781,192 A | 11/1988 | Demer | | 4,944,298 A | 7/1990 | Sholder |
| 4,782,826 A | 11/1988 | Fogarty | | 4,944,307 A | 7/1990 | Hon et al. |
| 4,783,106 A | 11/1988 | Nutter | | 4,945,761 A | 8/1990 | Lessi et al. |
| 4,785,822 A | 11/1988 | Wallace | | 4,949,724 A | 8/1990 | Mahutte et al. |
| 4,788,847 A | 12/1988 | Sterghos | | 4,952,205 A | 8/1990 | Mauerer et al. |
| 4,791,318 A | 12/1988 | Lewis et al. | | 4,952,928 A | 8/1990 | Carroll et al. |
| 4,794,803 A | 1/1989 | Osterhout et al. | | 4,953,563 A | 9/1990 | Kaiser et al. |
| 4,796,641 A | 1/1989 | Mills et al. | | 4,954,677 A | 9/1990 | Alberter et al. |
| 4,798,211 A | 1/1989 | Goor et al. | | 4,958,630 A | 9/1990 | Rosenbluth et al. |
| 4,798,227 A | 1/1989 | Goodwin | | 4,958,645 A | 9/1990 | Cadell et al. |
| 4,799,491 A | 1/1989 | Eckerle | | 4,960,424 A | 10/1990 | Grooters |
| 4,799,625 A | 1/1989 | Weaver, Jr. et al. | | 4,960,966 A | 10/1990 | Evans et al. |
| 4,802,488 A | 2/1989 | Eckerle | | 4,967,585 A | 11/1990 | Grimaldo |
| 4,803,987 A | 2/1989 | Calfee et al. | | 4,967,761 A | 11/1990 | Nathanielsz |
| 4,804,368 A | 2/1989 | Skakoon et al. | | 4,970,823 A | 11/1990 | Chen et al. |
| 4,807,321 A | 2/1989 | Grasselli et al. | | 4,971,251 A | 11/1990 | Dobrick et al. |
| 4,808,167 A | 2/1989 | Mann et al. | | 4,977,896 A | 12/1990 | Robinson et al. |
| 4,812,823 A | 3/1989 | Dickerson | | 4,978,335 A | 12/1990 | Arthur, III |
| 4,819,656 A | 4/1989 | Spector | | 4,978,338 A | 12/1990 | Melsky et al. |
| 4,820,265 A | 4/1989 | DeSatnick et al. | | 4,979,730 A | 12/1990 | Holbrook et al. |
| 4,820,953 A | 4/1989 | Saubolle et al. | | 4,980,671 A | 12/1990 | McCurdy |
| 4,821,167 A | 4/1989 | Wiebe | | 4,981,141 A | 1/1991 | Segalowitz |
| 4,821,723 A | 4/1989 | Baker, Jr. et al. | | 4,981,173 A | 1/1991 | Perkins et al. |
| 4,823,779 A | 4/1989 | Daly et al. | | 4,981,426 A | 1/1991 | Aoki et al. |
| 4,830,006 A | 5/1989 | Haluska et al. | | 4,987,897 A | 1/1991 | Funke et al. |
| 4,832,034 A | 5/1989 | Pizziconi et al. | | 4,988,337 A | 1/1991 | Ito |
| 4,833,384 A | 5/1989 | Munro et al. | | 4,992,794 A | 2/1991 | Brouwers |
| 4,834,731 A | 5/1989 | Nowak et al. | | 4,997,556 A | 3/1991 | Yano et al. |
| 4,838,857 A | 6/1989 | Strowe et al. | | 5,001,528 A | 3/1991 | Bahraman |
| 4,840,068 A | 6/1989 | Mayhew, Jr. | | 5,003,807 A | 4/1991 | Terrell et al. |
| 4,840,350 A | 6/1989 | Cook | | 5,003,975 A | 4/1991 | Hafelfinger et al. |
| 4,844,002 A | 7/1989 | Yasue et al. | | 5,003,976 A | 4/1991 | Alt |
| 4,846,153 A | 7/1989 | Berci | | 5,004,472 A | 4/1991 | Wallace |
| 4,846,191 A | 7/1989 | Brockway et al. | | 5,004,873 A | 4/1991 | Schnut |
| 4,846,664 A | 7/1989 | Hehl et al. | | 5,005,574 A | 4/1991 | Fearnot et al. |
| 4,854,328 A | 8/1989 | Pollack | | 5,005,586 A | 4/1991 | Lahr |
| 4,863,470 A | 9/1989 | Carter | | 5,006,844 A | 4/1991 | Ohta et al. |
| 4,865,587 A | 9/1989 | Walling | | 5,006,997 A | 4/1991 | Reich |
| 4,867,160 A | 9/1989 | Schaldach | | 5,007,401 A | 4/1991 | Grohn et al. |
| 4,867,498 A | 9/1989 | Delphia et al. | | 5,007,430 A | 4/1991 | Dardik |
| 4,867,618 A | 9/1989 | Brohammer | | 5,007,919 A | 4/1991 | Silva et al. |
| 4,869,252 A | 9/1989 | Gilli | | 5,009,662 A | 4/1991 | Wallace et al. |
| 4,870,258 A | 9/1989 | Mochizuki et al. | | 5,010,893 A | 4/1991 | Sholder |
| 4,871,351 A | 10/1989 | Feingold et al. | | 5,012,286 A | 4/1991 | Kawano et al. |
| 4,872,483 A | 10/1989 | Shah | | 5,012,810 A | 5/1991 | Strand et al. |
| 4,872,869 A | 10/1989 | Johns | | 5,013,292 A | 5/1991 | Lemay et al. |
| 4,873,677 A | 10/1989 | Sakamoto et al. | | 5,014,040 A | 5/1991 | Weaver et al. |
| 4,875,483 A | 10/1989 | Vollmann et al. | | 5,019,032 A | 5/1991 | Robertson |
| 4,880,004 A | 11/1989 | Baker, Jr. et al. | | 5,019,041 A | 5/1991 | Robinson et al. |
| 4,882,678 A | 11/1989 | Hollis et al. | | 5,020,845 A | 6/1991 | Falcoff et al. |
| 4,886,392 A | 12/1989 | Iio et al. | | 5,021,046 A | 6/1991 | Wallace |
| 4,893,630 A | 1/1990 | Bray, Jr. | | 5,022,395 A | 6/1991 | Russie |
| 4,895,151 A | 1/1990 | Grevis et al. | | 5,024,965 A | 6/1991 | Chang et al. |
| 4,896,594 A | 1/1990 | Baur et al. | | 5,026,180 A | 6/1991 | Tajima et al. |
| 4,898,158 A | 2/1990 | Daly et al. | | 5,026,360 A | 6/1991 | Johnsen et al. |
| 4,898,578 A | 2/1990 | Rubalcaba, Jr. | | 5,028,918 A | 7/1991 | Giles et al. |
| 4,899,751 A | 2/1990 | Cohen | | 5,032,822 A | 7/1991 | Sweet |
| 4,899,752 A | 2/1990 | Cohen | | 5,036,869 A | 8/1991 | Inahara et al. |
| 4,902,277 A | 2/1990 | Mathies et al. | | 5,038,800 A | 8/1991 | Oba |
| 4,903,701 A | 2/1990 | Moore et al. | | 5,041,086 A | 8/1991 | Koenig et al. |

| | | | | | | |
|---|---|---|---|---|---|---|
| 5,041,826 A | 8/1991 | Milheiser | | 5,184,132 A | 2/1993 | Baird |
| 5,042,503 A | 8/1991 | Torok et al. | | 5,184,614 A | 2/1993 | Collins et al. |
| 5,044,770 A | 9/1991 | Haghkar | | 5,184,619 A | 2/1993 | Austin |
| 5,046,661 A | 9/1991 | Kimura et al. | | 5,185,535 A | 2/1993 | Farb et al. |
| 5,048,060 A | 9/1991 | Arai et al. | | 5,186,224 A | 2/1993 | Schirmacher et al. |
| 5,050,922 A | 9/1991 | Falcoff | | 5,188,106 A | 2/1993 | Nappholz et al. |
| 5,052,910 A | 10/1991 | Hehl et al. | | 5,188,604 A | 2/1993 | Orth |
| 5,053,008 A | 10/1991 | Bajaj | | 5,192,314 A | 3/1993 | Daskalakis |
| 5,057,078 A | 10/1991 | Foote et al. | | 5,195,362 A | 3/1993 | Eason |
| 5,058,583 A | 10/1991 | Geddes et al. | | 5,197,322 A | 3/1993 | Indravudh |
| 5,061,239 A | 10/1991 | Shiels | | 5,199,427 A | 4/1993 | Strickland |
| 5,062,052 A | 10/1991 | Sparer et al. | | 5,199,428 A | 4/1993 | Obel et al. |
| 5,062,053 A | 10/1991 | Shirai et al. | | 5,201,753 A | 4/1993 | Lampropoulos et al. |
| 5,064,974 A | 11/1991 | Vigneau et al. | | 5,204,670 A | 4/1993 | Stinton |
| 5,067,960 A | 11/1991 | Grandjean et al. | | 5,207,429 A | 5/1993 | Walmsley et al. |
| 5,068,779 A | 11/1991 | Sullivan et al. | | 5,209,223 A | 5/1993 | McGorry et al. |
| 5,069,680 A | 12/1991 | Grandjean et al. | | 5,209,732 A | 5/1993 | Lampropoulos et al. |
| 5,077,102 A | 12/1991 | Chong | | 5,211,129 A | 5/1993 | Taylor et al. |
| 5,077,870 A | 1/1992 | Melbye et al. | | 5,211,161 A | 5/1993 | Stef et al. |
| 5,078,139 A | 1/1992 | Strand et al. | | 5,212,476 A | 5/1993 | Maloney |
| 5,082,006 A | 1/1992 | Jonasson et al. | | 5,213,331 A | 5/1993 | Avanzini |
| 5,083,563 A | 1/1992 | Collins et al. | | 5,215,523 A | 6/1993 | Williams et al. |
| 5,084,699 A | 1/1992 | DeMichele | | 5,218,343 A | 6/1993 | Stobbe et al. |
| 5,085,224 A | 2/1992 | Galen et al. | | 5,218,957 A | 6/1993 | Strickland |
| 5,085,258 A | 2/1992 | Fink, Jr. et al. | | 5,226,429 A | 7/1993 | Kuzmak |
| 5,089,673 A | 2/1992 | Strzodka | | 5,226,604 A | 7/1993 | Seiffert et al. |
| 5,089,979 A | 2/1992 | McEachern et al. | | 5,230,694 A | 7/1993 | Rosenblum |
| 5,095,309 A | 3/1992 | Troyk et al. | | 5,233,985 A | 8/1993 | Hudrlik |
| 5,096,271 A | 3/1992 | Portman | | 5,235,326 A | 8/1993 | Beigel et al. |
| 5,097,831 A | 3/1992 | Lekholm | | 5,244,269 A | 9/1993 | Harriehausen et al. |
| 5,098,384 A | 3/1992 | Abrams | | 5,244,461 A | 9/1993 | Derlien et al. |
| 5,099,845 A | 3/1992 | Besz et al. | | 5,246,008 A | 9/1993 | Mueller et al. |
| 5,103,832 A | 4/1992 | Jackson | | 5,249,858 A | 10/1993 | Nusser |
| 5,105,810 A | 4/1992 | Collins et al. | | 5,250,020 A | 10/1993 | Bley |
| 5,107,850 A | 4/1992 | Olive | | 5,254,096 A | 10/1993 | Rondelet et al. |
| 5,112,344 A | 5/1992 | Petros et al. | | 5,256,157 A | 10/1993 | Samiotes et al. |
| 5,113,859 A | 5/1992 | Funke et al. | | 5,263,244 A | 11/1993 | Centa et al. |
| 5,113,869 A | 5/1992 | Nappholz et al. | | 5,263,981 A | 11/1993 | Polyak et al. |
| 5,115,676 A | 5/1992 | Lee | | 5,267,940 A | 12/1993 | Moulder |
| 5,117,825 A | 6/1992 | Grevious | | 5,267,942 A | 12/1993 | Saperston |
| 5,120,313 A | 6/1992 | Elftman | | 5,269,891 A | 12/1993 | Colin et al. |
| 5,121,777 A | 6/1992 | Leininger et al. | | 5,271,395 A | 12/1993 | Wahlstrand et al. |
| 5,127,451 A | 7/1992 | Fink, Jr. et al. | | 5,274,859 A | 1/1994 | Redman et al. |
| 5,129,394 A | 7/1992 | Mehra | | 5,280,789 A | 1/1994 | Potts |
| 5,129,806 A | 7/1992 | Hehl et al. | | 5,282,839 A | 2/1994 | Roline et al. |
| 5,131,145 A | 7/1992 | Badoureaux et al. | | 5,282,840 A | 2/1994 | Hudrlik |
| 5,131,388 A | 7/1992 | Pless et al. | | 5,291,894 A | 3/1994 | Nagy et al. |
| 5,133,358 A | 7/1992 | Gustafson et al. | | 5,292,219 A | 3/1994 | Merin et al. |
| 5,135,488 A | 8/1992 | Foote et al. | | 5,295,967 A | 3/1994 | Rondelet et al. |
| 5,139,484 A | 8/1992 | Hazon et al. | | 5,298,022 A | 3/1994 | Bernardi et al. |
| 5,144,949 A | 9/1992 | Olson | | 5,298,884 A | 3/1994 | Gilmore et al. |
| 5,148,580 A | 9/1992 | Dyckow et al. | | 5,300,093 A | 4/1994 | Koestner |
| 5,148,695 A | 9/1992 | Ellis | | 5,300,120 A | 4/1994 | Knapp et al. |
| 5,152,770 A | 10/1992 | Bangmark et al. | | 5,304,112 A | 4/1994 | Mrklas et al. |
| 5,152,776 A | 10/1992 | Pinchuk | | 5,305,923 A | 4/1994 | Kirschner et al. |
| 5,154,170 A | 10/1992 | Bennett et al. | | 5,312,443 A | 5/1994 | Adams et al. |
| 5,154,171 A | 10/1992 | Chirife et al. | | 5,312,452 A | 5/1994 | Salo |
| 5,154,693 A | 10/1992 | East et al. | | 5,312,453 A | 5/1994 | Shelton et al. |
| 5,156,972 A | 10/1992 | Issachar et al. | | 5,313,953 A | 5/1994 | Yomtov et al. |
| 5,158,078 A | 10/1992 | Bennett et al. | | 5,314,451 A | 5/1994 | Mulier |
| 5,163,429 A | 11/1992 | Cohen | | 5,314,457 A | 5/1994 | Jeutter et al. |
| 5,163,904 A | 11/1992 | Lampropoulos et al. | | 5,324,315 A | 6/1994 | Grevious |
| 5,167,615 A | 12/1992 | East et al. | | 5,325,834 A | 7/1994 | Ballheimer et al. |
| 5,168,757 A | 12/1992 | Rabenau et al. | | 5,326,249 A | 7/1994 | Weissfloch et al. |
| 5,168,982 A | 12/1992 | Hakanen et al. | | 5,328,460 A | 7/1994 | Lord et al. |
| 5,171,299 A | 12/1992 | Heitzmann et al. | | 5,330,511 A | 7/1994 | Boute et al. |
| 5,173,873 A | 12/1992 | Wu et al. | | 5,337,750 A | 8/1994 | Wallock |
| 5,174,286 A | 12/1992 | Chirige et al. | | 5,341,430 A | 8/1994 | Aulia et al. |
| 5,174,291 A | 12/1992 | Schoonen et al. | | 5,342,401 A | 8/1994 | Spano et al. |
| 5,176,502 A | 1/1993 | Sanderson et al. | | 5,342,406 A | 8/1994 | Thompson |
| 5,178,197 A | 1/1993 | Healy | | 5,344,388 A | 9/1994 | Maxwell et al. |
| 5,181,423 A | 1/1993 | Philipps et al. | | 5,347,476 A | 9/1994 | McBean, Sr. |
| 5,181,517 A | 1/1993 | Hickey | | 5,348,210 A | 9/1994 | Linzell et al. |

| | | | | | | |
|---|---|---|---|---|---|---|
| 5,348,536 A | 9/1994 | Young et al. | | 5,540,731 A | 7/1996 | Testerman |
| 5,350,413 A | 9/1994 | Miller et al. | | 5,541,857 A | 7/1996 | Walter et al. |
| 5,352,180 A | 10/1994 | Candelon et al. | | 5,545,140 A | 8/1996 | Conero et al. |
| 5,353,622 A | 10/1994 | Theener | | 5,545,151 A | 8/1996 | O'Connor et al. |
| 5,353,800 A | 10/1994 | Pohndorf et al. | | 5,545,186 A | 8/1996 | Olson et al. |
| 5,354,200 A | 10/1994 | Klein et al. | | 5,545,214 A | 8/1996 | Stevens |
| 5,354,316 A | 10/1994 | Keimel | | 5,547,470 A | 8/1996 | Johnson et al. |
| 5,354,319 A | 10/1994 | Wyborny et al. | | 5,551,427 A | 9/1996 | Altman |
| 5,360,407 A | 11/1994 | Leonard et al. | | 5,551,439 A | 9/1996 | Hickey |
| 5,365,462 A | 11/1994 | McBean, Sr. | | 5,554,185 A | 9/1996 | Block et al. |
| 5,365,619 A | 11/1994 | Solomon | | 5,558,644 A | 9/1996 | Boyd et al. |
| 5,365,985 A | 11/1994 | Todd et al. | | 5,564,434 A | 10/1996 | Halperin et al. |
| 5,368,040 A | 11/1994 | Carney | | 5,575,770 A | 11/1996 | Melsky et al. |
| 5,370,665 A | 12/1994 | Hudrlik | | 5,584,803 A | 12/1996 | Stevens et al. |
| 5,373,852 A | 12/1994 | Harrison et al. | | 5,586,629 A | 12/1996 | Shoberg et al. |
| 5,375,073 A | 12/1994 | McBean | | 5,591,171 A | 1/1997 | Brown |
| 5,377,128 A | 12/1994 | McBean | | 5,592,939 A * | 1/1997 | Martinelli ............... 600/424 |
| 5,378,231 A | 1/1995 | Johnson et al. | | 5,593,430 A | 1/1997 | Renger |
| 5,382,232 A | 1/1995 | Hague et al. | | 5,594,665 A | 1/1997 | Walter et al. |
| 5,383,915 A | 1/1995 | Adams | | 5,596,986 A | 1/1997 | Goldfarb |
| 5,388,578 A | 2/1995 | Yomtov et al. | | 5,597,284 A | 1/1997 | Weltlich et al. |
| 5,388,586 A | 2/1995 | Lee et al. | | 5,610,083 A | 3/1997 | Chan et al. |
| 5,388,831 A | 2/1995 | Quadri et al. | | 5,611,768 A | 3/1997 | Tutrone, Jr. |
| 5,394,909 A | 3/1995 | Mitchell et al. | | 5,612,497 A | 3/1997 | Walter et al. |
| 5,396,899 A | 3/1995 | Strittmatter | | 5,615,671 A | 4/1997 | Schoonen et al. |
| 5,402,944 A | 4/1995 | Pape et al. | | 5,619,991 A | 4/1997 | Sloane |
| 5,406,957 A | 4/1995 | Tansey | | 5,622,869 A | 4/1997 | Lewis et al. |
| 5,409,009 A | 4/1995 | Olson | | 5,625,946 A | 5/1997 | Wildeson et al. |
| 5,411,031 A | 5/1995 | Yomtov | | 5,626,623 A | 5/1997 | Kieval et al. |
| 5,411,551 A | 5/1995 | Winston et al. | | 5,626,630 A | 5/1997 | Markowitz et al. |
| 5,411,552 A | 5/1995 | Andersen et al. | | 5,630,836 A | 5/1997 | Prem et al. |
| 5,416,372 A | 5/1995 | Ljungstroem et al. | | 5,634,255 A | 6/1997 | Bishop et al. |
| 5,417,226 A | 5/1995 | Juma | | 5,637,083 A | 6/1997 | Bertrand et al. |
| 5,417,717 A | 5/1995 | Salo et al. | | 5,643,207 A | 7/1997 | Rise |
| 5,425,362 A | 6/1995 | Siker et al. | | 5,645,065 A * | 7/1997 | Shapiro et al. ............. 600/424 |
| 5,425,713 A | 6/1995 | Taylor et al. | | 5,645,116 A | 7/1997 | McDonald |
| 5,431,171 A | 7/1995 | Harrison et al. | | 5,650,766 A | 7/1997 | Burgmann et al. |
| 5,431,629 A | 7/1995 | Lampropoulos et al. | | 5,673,585 A | 10/1997 | Bishop et al. |
| 5,431,694 A | 7/1995 | Snaper et al. | | 5,676,690 A | 10/1997 | Noren et al. |
| 5,433,694 A | 7/1995 | Lim et al. | | 5,681,285 A | 10/1997 | Ford et al. |
| 5,437,605 A | 8/1995 | Helmy et al. | | 5,686,831 A | 11/1997 | Vandervalk et al. |
| 5,443,215 A | 8/1995 | Fackler | | 5,687,734 A | 11/1997 | Dempsey et al. |
| 5,447,519 A | 9/1995 | Peterson | | 5,693,076 A | 12/1997 | Kaemmerer |
| 5,449,345 A | 9/1995 | Taylor et al. | | 5,702,368 A | 12/1997 | Stevens et al. |
| 5,449,368 A | 9/1995 | Kuzmak | | 5,702,427 A | 12/1997 | Ecker et al. |
| 5,456,690 A | 10/1995 | Duong-Van | | 5,702,431 A | 12/1997 | Wang et al. |
| 5,461,293 A | 10/1995 | Rozman et al. | | 5,704,352 A | 1/1998 | Tremblay et al. |
| 5,461,390 A | 10/1995 | Hoshen | | 5,711,302 A | 1/1998 | Lampropoulos et al. |
| 5,464,435 A | 11/1995 | Neumann | | 5,715,786 A | 2/1998 | Seiberth et al. |
| 5,467,627 A | 11/1995 | Smith et al. | | 5,715,837 A | 2/1998 | Chen |
| 5,474,226 A | 12/1995 | Joseph | | 5,716,342 A | 2/1998 | Dumbraveanu et al. |
| 5,479,818 A | 1/1996 | Walter et al. | | 5,720,436 A | 2/1998 | Buschor et al. |
| 5,482,049 A | 1/1996 | Addiss et al. | | 5,721,382 A | 2/1998 | Kriesel et al. |
| 5,487,760 A | 1/1996 | Villafana | | 5,730,101 A | 3/1998 | Aupperle |
| 5,490,514 A | 2/1996 | Rosenberg | | 5,732,710 A | 3/1998 | Rabinovich et al. |
| 5,493,738 A | 2/1996 | Sanderson et al. | | 5,733,313 A | 3/1998 | Barreras, Sr. et al. |
| 5,494,036 A | 2/1996 | Uber, III et al. | | 5,738,652 A | 4/1998 | Boyd et al. |
| 5,494,193 A | 2/1996 | Kirschner et al. | | 5,742,233 A | 4/1998 | Hoffman et al. |
| 5,504,474 A | 4/1996 | Libman et al. | | 5,743,267 A | 4/1998 | Nikolic et al. |
| 5,505,916 A | 4/1996 | Berry, Jr. | | 5,749,369 A | 5/1998 | Rabinovich et al. |
| 5,507,412 A | 4/1996 | Ebert et al. | | 5,749,909 A | 5/1998 | Schroeppel et al. |
| 5,507,737 A | 4/1996 | Palmskog et al. | | 5,755,687 A | 5/1998 | Donlon |
| 5,507,785 A | 4/1996 | Deno | | 5,755,748 A | 5/1998 | Borza |
| 5,509,888 A | 4/1996 | Miller | | 5,765,568 A | 6/1998 | Sweezer, Jr. et al. |
| 5,509,891 A | 4/1996 | DeRidder | | 5,769,812 A | 6/1998 | Stevens et al. |
| 5,513,945 A | 5/1996 | Hartmann et al. | | 5,771,903 A * | 6/1998 | Jakobsson ............... 128/898 |
| 5,514,103 A | 5/1996 | Srisathapat et al. | | 5,782,774 A | 7/1998 | Shmulewitz |
| 5,518,504 A | 5/1996 | Polyak | | 5,787,520 A | 8/1998 | Dunbar |
| 5,520,606 A | 5/1996 | Schoolman et al. | | 5,791,344 A | 8/1998 | Schulman et al. |
| 5,523,740 A | 6/1996 | Burgmann et al. | | 5,792,094 A | 8/1998 | Stevens et al. |
| 5,534,018 A | 7/1996 | Wahlstrand et al. | | 5,792,179 A | 8/1998 | Sideris |
| 5,535,752 A | 7/1996 | Halperin et al. | | 5,795,325 A | 8/1998 | Valley et al. |
| 5,538,005 A | 7/1996 | Harrison et al. | | 5,796,827 A | 8/1998 | Coppersmith et al. |

| | | | | | | |
|---|---|---|---|---|---|---|
| 5,797,403 | A | 8/1998 | DiLorenzo | 6,152,885 A | 11/2000 | Taepke |
| 5,800,375 | A | 9/1998 | Sweezer et al. | 6,158,965 A | 12/2000 | Butterfield et al. |
| 5,803,917 | A | 9/1998 | Butterfield et al. | 6,159,156 A | 12/2000 | Van Bockel et al. |
| 5,807,265 | A | 9/1998 | Itoigawa et al. | 6,162,180 A | 12/2000 | Miesel et al. |
| 5,807,336 | A | 9/1998 | Russo et al. | 6,162,245 A | 12/2000 | Jayaraman |
| 5,810,015 | A | 9/1998 | Flaherty | 6,168,614 B1 | 1/2001 | Andersen et al. |
| 5,810,757 | A | 9/1998 | Sweezer, Jr. et al. | 6,171,252 B1 | 1/2001 | Roberts |
| 5,810,841 | A | 9/1998 | McNeirney et al. | 6,210,347 B1 | 4/2001 | Forsell |
| 5,814,016 | A | 9/1998 | Valley et al. | 6,216,028 B1 | 4/2001 | Haynor et al. |
| 5,817,093 | A | 10/1998 | Williamson, IV et al. | 6,234,745 B1 | 5/2001 | Pugh et al. |
| 5,833,603 | A | 11/1998 | Kovacs et al. | 6,240,316 B1 | 5/2001 | Richmond et al. |
| 5,836,300 | A | 11/1998 | Mault | 6,240,318 B1 | 5/2001 | Phillips |
| 5,836,886 | A | 11/1998 | Itoigawa et al. | 6,245,102 B1 | 6/2001 | Jayaraman |
| 5,840,081 | A | 11/1998 | Andersen et al. | 6,248,080 B1 | 6/2001 | Miesel et al. |
| 5,849,225 | A | 12/1998 | Ebina et al. | 6,251,093 B1 | 6/2001 | Valley et al. |
| 5,855,597 | A | 1/1999 | Jayaraman et al. | 6,269,819 B1 | 8/2001 | Oz et al. |
| 5,855,601 | A | 1/1999 | Bessler et al. | 6,277,078 B1 | 8/2001 | Porat et al. |
| 5,860,938 | A | 1/1999 | LaFontaine et al. | 6,285,897 B1 | 9/2001 | Kilcoyne et al. |
| 5,861,018 | A | 1/1999 | Feierbach | 6,292,697 B1 | 9/2001 | Roberts |
| 5,863,366 | A | 1/1999 | Snow | 6,305,381 B1 | 10/2001 | Weijand et al. |
| 5,868,702 | A | 2/1999 | Stevens et al. | 6,309,350 B1 | 10/2001 | Van Tassel et al. |
| 5,873,837 | A | 2/1999 | Lieber et al. | 6,315,769 B1 | 11/2001 | Peer et al. |
| 5,875,953 | A | 3/1999 | Shioya et al. | 6,319,208 B1 | 11/2001 | Abita et al. |
| 5,879,499 | A | 3/1999 | Corvi | 6,328,699 B1 | 12/2001 | Eigler et al. |
| 5,881,919 | A | 3/1999 | Womac et al. | 6,338,735 B1 | 1/2002 | Stevens |
| 5,885,238 | A | 3/1999 | Stevens et al. | 6,357,438 B1 | 3/2002 | Hansen |
| 5,887,475 | A | 3/1999 | Muldner | 6,360,122 B1 | 3/2002 | Fischell et al. |
| 5,899,927 | A | 5/1999 | Ecker et al. | 6,360,822 B1 | 3/2002 | Robertson et al. |
| 5,916,179 | A | 6/1999 | Sharrock | 6,366,799 B1 | 4/2002 | Acker et al. |
| 5,916,237 | A | 6/1999 | Schu | 6,366,817 B1 | 4/2002 | Kung |
| 5,928,182 | A | 7/1999 | Kraus et al. | 6,379,308 B1 | 4/2002 | Brockway et al. |
| 5,935,078 | A | 8/1999 | Feierbach | 6,379,380 B1 | 4/2002 | Satz |
| 5,935,083 | A | 8/1999 | Williams | 6,398,752 B1 | 6/2002 | Sweezer, Jr. et al. |
| 5,938,669 | A | 8/1999 | Klaiber et al. | 6,409,674 B1 | 6/2002 | Brockway et al. |
| 5,951,487 | A | 9/1999 | Brehmeier-Flick et al. | 6,416,291 B1 | 7/2002 | Butterfield et al. |
| 5,957,861 | A | 9/1999 | Combs et al. | 6,423,031 B1 | 7/2002 | Donlon |
| 5,967,986 | A | 10/1999 | Cimochowski et al. | 6,430,444 B1 | 8/2002 | Borza et al. |
| 5,970,801 | A | 10/1999 | Ciobanu et al. | 6,431,175 B1 | 8/2002 | Penner et al. |
| 5,971,934 | A | 10/1999 | Scherer et al. | 6,432,040 B1 | 8/2002 | Meah |
| 5,974,873 | A | 11/1999 | Nelson et al. | 6,443,887 B1 | 9/2002 | Derus et al. |
| 5,978,985 | A | 11/1999 | Thurman | 6,443,893 B1 | 9/2002 | Schnakenberg et al. |
| 5,991,664 | A | 11/1999 | Seligman | 6,450,173 B1 | 9/2002 | Forsell |
| 5,993,395 | A | 11/1999 | Shulze | 6,450,543 B1 | 9/2002 | Fukano et al. |
| 5,993,398 | A | 11/1999 | Alperin | 6,450,946 B1 | 9/2002 | Forsell |
| 5,995,874 | A | 11/1999 | Borza et al. | 6,453,907 B1 | 9/2002 | Forsell et al. |
| 6,009,878 | A | 1/2000 | Weijand et al. | 6,454,698 B1 | 9/2002 | Forsell et al. |
| 6,010,482 | A | 1/2000 | Kriesel et al. | 6,454,699 B1 | 9/2002 | Forsell |
| 6,015,386 | A | 1/2000 | Kensey et al. | 6,454,700 B1 | 9/2002 | Forsell |
| 6,015,387 | A | 1/2000 | Schwartz et al. | 6,454,701 B1 | 9/2002 | Forsell |
| 6,019,729 | A | 2/2000 | Itoigawa et al. | 6,460,543 B1 | 10/2002 | Forsell et al. |
| 6,024,704 | A | 2/2000 | Meador et al. | 6,461,292 B1 | 10/2002 | Forsell et al. |
| 6,030,413 | A | 2/2000 | Lazarus | 6,461,293 B1 | 10/2002 | Forsell |
| 6,035,461 | A | 3/2000 | Nguyen | 6,463,329 B1 | 10/2002 | Goedeke |
| 6,053,873 | A | 4/2000 | Govari et al. | 6,463,935 B1 | 10/2002 | Forsell |
| 6,056,723 | A | 5/2000 | Donlon | 6,464,628 B1 | 10/2002 | Forsell |
| 6,058,330 | A | 5/2000 | Borza et al. | 6,470,212 B1 | 10/2002 | Weijand et al. |
| 6,059,757 | A | 5/2000 | Macoviak et al. | 6,470,213 B1 | 10/2002 | Alley |
| 6,067,474 | A | 5/2000 | Schulman et al. | 6,470,892 B1 | 10/2002 | Forsell |
| 6,067,991 | A | 5/2000 | Forsell et al. | 6,471,635 B1 | 10/2002 | Forsell |
| 6,071,267 | A | 6/2000 | Zamierowski | 6,475,136 B1 | 11/2002 | Forsell |
| 6,076,016 | A | 6/2000 | Feierbach | 6,475,170 B1 | 11/2002 | Doron et al. |
| 6,083,174 | A | 7/2000 | Brehmeier-Flick et al. | 6,481,292 B1 | 11/2002 | Reich |
| 6,089,831 | A | 7/2000 | Bruehmann et al. | 6,482,145 B1 | 11/2002 | Forsell |
| 6,090,096 | A | 7/2000 | St. Goar et al. | 6,482,171 B1 | 11/2002 | Corvi et al. |
| 6,102,678 | A | 8/2000 | Peciat | 6,482,177 B1 | 11/2002 | Leinders et al. |
| 6,102,856 | A | 8/2000 | Groff et al. | 6,486,588 B2 | 11/2002 | Doron et al. |
| 6,102,922 | A | 8/2000 | Jakobsson et al. | 6,503,189 B1 | 1/2003 | Forsell et al. |
| 6,106,477 | A | 8/2000 | Miesel et al. | 6,503,208 B1 | 1/2003 | Skovlund |
| 6,106,551 | A | 8/2000 | Crossett et al. | 6,504,286 B1 | 1/2003 | Porat et al. |
| 6,110,145 | A | 8/2000 | Macoviak | 6,505,062 B1 | 1/2003 | Ritter et al. |
| 6,113,553 | A | 9/2000 | Chubbuck | 6,511,490 B2 * | 1/2003 | Robert .................. 606/151 |
| 6,131,664 | A | 10/2000 | Sonnier | 6,516,212 B1 | 2/2003 | Bladen et al. |
| 6,135,945 | A | 10/2000 | Sultan | 6,531,739 B2 | 3/2003 | Cable et al. |

| | | | | | | |
|---|---|---|---|---|---|---|
| 6,533,719 B2 | 3/2003 | Kuyava et al. | | 7,153,262 B2 | 12/2006 | Stivoric et al. |
| 6,533,733 B1 | 3/2003 | Ericson et al. | | 7,187,978 B2 | 3/2007 | Makek et al. |
| 6,542,350 B1 | 4/2003 | Rogers | | 7,225,032 B2 | 5/2007 | Schmeling et al. |
| 6,543,907 B2 | 4/2003 | Nishiyama et al. | | 7,257,438 B2 | 8/2007 | Kinast |
| 6,558,321 B1 | 5/2003 | Burd et al. | | 7,285,090 B2 | 10/2007 | Stivoric et al. |
| 6,558,994 B2 | 5/2003 | Cha et al. | | 2001/0011543 A1 | 8/2001 | Forsell |
| 6,573,563 B2 | 6/2003 | Lee et al. | | 2001/0041823 A1 | 11/2001 | Snyder et al. |
| 6,582,462 B1 | 6/2003 | Andersen et al. | | 2002/0049394 A1 | 4/2002 | Roy et al. |
| 6,587,709 B2 | 7/2003 | Solf et al. | | 2002/0120200 A1 | 8/2002 | Brockway et al. |
| 6,589,189 B2 | 7/2003 | Meyerson et al. | | 2002/0138009 A1 | 9/2002 | Brockway et al. |
| 6,599,250 B2 | 7/2003 | Webb et al. | | 2002/0177782 A1 | 11/2002 | Penner |
| 6,605,112 B1 | 8/2003 | Moll et al. | | 2003/0009201 A1 | 1/2003 | Forsell |
| 6,629,534 B1 | 10/2003 | Dell et al. | | 2003/0023134 A1 | 1/2003 | Tracey |
| 6,640,137 B2 | 10/2003 | MacDonald | | 2003/0030893 A1 | 2/2003 | Cornelius et al. |
| 6,641,610 B2 | 11/2003 | Briefs et al. | | 2003/0032857 A1 | 2/2003 | Forsell |
| 6,645,143 B2 | 11/2003 | Van Tassel et al. | | 2003/0037591 A1 | 2/2003 | Ashton et al. |
| 6,654,629 B2 | 11/2003 | Montegrande | | 2003/0045775 A1 | 3/2003 | Forsell |
| 6,673,109 B2 | 1/2004 | Cox | | 2003/0066536 A1 | 4/2003 | Forsell |
| 6,678,561 B2 | 1/2004 | Forsell et al. | | 2003/0088148 A1 | 5/2003 | Forsell |
| 6,682,480 B1 | 1/2004 | Habib et al. | | 2003/0092962 A1 | 5/2003 | Forsell |
| 6,682,503 B1 | 1/2004 | Fariss et al. | | 2003/0093117 A1 | 5/2003 | Saadat |
| 6,682,559 B2 | 1/2004 | Myers | | 2003/0100929 A1 | 5/2003 | Forsell |
| 6,689,046 B2 | 2/2004 | Sayet et al. | | 2003/0105385 A1 | 6/2003 | Forsell |
| 6,690,963 B2 | 2/2004 | Ben-Haim et al. | | 2003/0109771 A1 | 6/2003 | Forsell |
| 6,695,866 B1 | 2/2004 | Kuehn et al. | | 2003/0114729 A1 | 6/2003 | Forsell |
| 6,709,385 B2 | 3/2004 | Forsell et al. | | 2003/0120150 A1 | 6/2003 | Govari |
| 6,718,200 B2 | 4/2004 | Marmaropoulos et al. | | 2003/0125605 A1 | 7/2003 | Forsell |
| 6,719,787 B2 | 4/2004 | Cox | | 2003/0125768 A1 | 7/2003 | Peter |
| 6,719,788 B2 | 4/2004 | Cox | | 2003/0135089 A1 | 7/2003 | Forsell |
| 6,719,789 B2 | 4/2004 | Cox | | 2003/0135090 A1 | 7/2003 | Forsell |
| 6,731,976 B2 | 5/2004 | Penn et al. | | 2003/0136417 A1 | 7/2003 | Fonseca et al. |
| 6,733,525 B2 | 5/2004 | Yang et al. | | 2003/0144648 A1 | 7/2003 | Forsell |
| 6,736,846 B2 | 5/2004 | Cox | | 2003/0163079 A1 | 8/2003 | Burnett |
| 6,752,813 B2 | 6/2004 | Goldfarb et al. | | 2003/0216666 A1 | 11/2003 | Ericson et al. |
| 6,757,557 B1 | 6/2004 | Bladen et al. | | 2003/0225371 A1 | 12/2003 | Hadzic et al. |
| 6,779,851 B2 | 8/2004 | Bouchiere | | 2004/0014456 A1 | 1/2004 | Vnnen |
| 6,796,942 B1 | 9/2004 | Kreiner et al. | | 2004/0016874 A1 | 1/2004 | Rao et al. |
| 6,822,343 B2 | 11/2004 | Estevez | | 2004/0039256 A1 | 2/2004 | Kawatahara et al. |
| 6,851,628 B1 | 2/2005 | Garrison et al. | | 2004/0054351 A1 | 3/2004 | Deniega et al. |
| 6,855,115 B2 | 2/2005 | Fonseca et al. | | 2004/0054352 A1 | 3/2004 | Adams et al. |
| 6,889,772 B2 | 5/2005 | Buytaert et al. | | 2004/0055610 A1 | 3/2004 | Forsell |
| 6,890,300 B2 | 5/2005 | Lloyd et al. | | 2004/0064030 A1 | 4/2004 | Forsell |
| 6,896,651 B2 | 5/2005 | Gross et al. | | 2004/0082867 A1 | 4/2004 | Esch et al. |
| 6,898,690 B2 | 5/2005 | Lambrecht et al. | | 2004/0082904 A1 | 4/2004 | Houde et al. |
| 6,913,600 B2 | 7/2005 | Valley et al. | | 2004/0113790 A1 | 6/2004 | Hamel et al. |
| 6,915,165 B2 | 7/2005 | Forsell et al. | | 2004/0133092 A1 | 7/2004 | Kain |
| 6,926,246 B2 | 8/2005 | Ginggen et al. | | 2004/0143212 A1 | 7/2004 | Trombley et al. |
| 6,929,653 B2 | 8/2005 | Strecter | | 2004/0147969 A1 | 7/2004 | Mann et al. |
| 6,932,792 B1 | 8/2005 | St. Goar et al. | | 2004/0172087 A1 | 9/2004 | Forsell |
| 6,951,229 B2 | 10/2005 | Garrison et al. | | 2004/0186396 A1 | 9/2004 | Roy et al. |
| 6,951,571 B1 | 10/2005 | Srivastava | | 2004/0193045 A1 | 9/2004 | Scarborough et al. |
| 6,953,429 B2 | 10/2005 | Forsell et al. | | 2004/0215159 A1 | 10/2004 | Forsell |
| 6,961,619 B2 | 11/2005 | Casey | | 2004/0243148 A1 | 12/2004 | Wasielewski |
| 6,970,742 B2 | 11/2005 | Mann et al. | | 2004/0254537 A1 | 12/2004 | Conlon et al. |
| 6,979,350 B2 | 12/2005 | Moll et al. | | 2005/0004516 A1 | 1/2005 | Vanney |
| 6,985,078 B2 | 1/2006 | Suzuki et al. | | 2005/0015014 A1 | 1/2005 | Fonseca et al. |
| 6,989,027 B2 | 1/2006 | Allen et al. | | 2005/0025979 A1 | 2/2005 | Sandt et al. |
| 7,011,095 B2 | 3/2006 | Wolf et al. | | 2005/0027175 A1 | 2/2005 | Yang |
| 7,011,624 B2 | 3/2006 | Forsell et al. | | 2005/0027998 A1 | 2/2005 | Teglia et al. |
| 7,017,583 B2 | 3/2006 | Forsell et al. | | 2005/0038328 A1 | 2/2005 | Stoehrer et al. |
| 7,018,406 B2 | 3/2006 | Seguin et al. | | 2005/0061079 A1 | 3/2005 | Schulman |
| 7,021,402 B2 | 4/2006 | Beato et al. | | 2005/0065450 A1 | 3/2005 | Stuebe et al. |
| 7,025,727 B2 | 4/2006 | Brockway et al. | | 2005/0102026 A1 | 5/2005 | Turner et al. |
| 7,044,920 B2 | 5/2006 | Letort et al. | | 2005/0159789 A1 | 7/2005 | Brockway et al. |
| 7,060,080 B2 | 6/2006 | Bachmann et al. | | 2005/0165317 A1 | 7/2005 | Turner et al. |
| 7,081,683 B2 | 7/2006 | Ariav et al. | | 2005/0182330 A1 | 8/2005 | Brockway et al. |
| 7,109,933 B2 | 9/2006 | Ito et al. | | 2005/0187482 A1 | 8/2005 | O'Brien et al. |
| 7,131,447 B2 | 11/2006 | Sterman et al. | | 2005/0187488 A1 | 8/2005 | Wolf |
| 7,131,945 B2 | 11/2006 | Fink et al. | | 2005/0192642 A1 | 9/2005 | Forsell |
| 7,134,580 B2 | 11/2006 | Garrison et al. | | 2005/0203360 A1 | 9/2005 | Brauker et al. |
| 7,143,462 B2 | 12/2006 | Hohlbein | | 2005/0240144 A1 | 10/2005 | Wassemann et al. |
| 7,144,400 B2 | 12/2006 | Byrum et al. | | 2005/0240155 A1 | 10/2005 | Conlon |
| 7,147,640 B2 | 12/2006 | Huebner et al. | | 2005/0240156 A1 | 10/2005 | Conlon |

| | | | | | | |
|---|---|---|---|---|---|---|
| 2005/0250979 | A1 | 11/2005 | Coe | 2007/0156013 A1 | 7/2007 | Birk |
| 2005/0267406 | A1 | 12/2005 | Hassler | 2007/0167672 A1 | 7/2007 | Dlugos et al. |
| 2005/0267500 | A1 | 12/2005 | Hassler, Jr. et al. | 2007/0173881 A1 | 7/2007 | Birk et al. |
| 2005/0272968 | A1 | 12/2005 | Byrum et al. | 2007/0179583 A1 | 8/2007 | Goetzinger et al. |
| 2005/0277960 | A1 | 12/2005 | Hassler et al. | 2007/0208313 A1 | 9/2007 | Conlon et al. |
| 2005/0277974 | A1 | 12/2005 | Hassler et al. | 2007/0225781 A1 | 9/2007 | Saadat et al. |
| 2005/0288604 | A1 | 12/2005 | Eigler et al. | 2008/0009680 A1 | 1/2008 | Hassler |
| 2005/0288720 | A1 | 12/2005 | Ross et al. | 2008/0172072 A1 | 7/2008 | Pool et al. |
| 2005/0288721 | A1 | 12/2005 | Girouard et al. | 2008/0250340 A1 | 10/2008 | Dlugos et al. |
| 2005/0288739 | A1 | 12/2005 | Hassler et al. | 2008/0250341 A1 | 10/2008 | Dlugos et al. |
| 2005/0288740 | A1 | 12/2005 | Hassler | 2009/0005703 A1 | 1/2009 | Fasciano |
| 2005/0288741 | A1 | 12/2005 | Hassler et al. | | | |
| 2005/0288742 | A1 | 12/2005 | Giordano et al. | FOREIGN PATENT DOCUMENTS | | |
| 2006/0002035 | A1 | 1/2006 | Gao et al. | CA | 1059035 | 7/1979 |
| 2006/0010090 | A1 | 1/2006 | Brockway et al. | CA | 1119469 | 3/1982 |
| 2006/0020224 | A1 | 1/2006 | Geiger | CA | 1275135 | 10/1990 |
| 2006/0020305 | A1 | 1/2006 | Desai et al. | CA | 1277885 | 12/1990 |
| 2006/0035446 | A1 | 2/2006 | Chang et al. | CA | 1317482 | 5/1993 |
| 2006/0047205 | A1 | 3/2006 | Ludomirsky et al. | CA | 2082015 | 5/1993 |
| 2006/0049714 | A1 | 3/2006 | Liu et al. | CA | 1327191 | 2/1994 |
| 2006/0058627 | A1 | 3/2006 | Flaherty et al. | CA | 2119101 | 9/1994 |
| 2006/0064134 | A1 | 3/2006 | Mazar et al. | CA | 2305998 | 4/1999 |
| 2006/0085051 | A1 | 4/2006 | Fritsch | CN | 1119469 | 3/1982 |
| 2006/0089571 | A1 | 4/2006 | Gertner | CN | 1059035 | 2/1992 |
| 2006/0089619 | A1 | 4/2006 | Ginggen | CN | 1241003 | 1/2000 |
| 2006/0094966 | A1 | 5/2006 | Brockway et al. | DE | 9416395 | 12/1994 |
| 2006/0100531 | A1 | 5/2006 | Moser | DE | 1015694 | 6/2003 |
| 2006/0113187 | A1 | 6/2006 | Deng et al. | EA | 4581 | 6/2004 |
| 2006/0118793 | A1 | 6/2006 | Yang et al. | EP | 0417171 | 3/1991 |
| 2006/0122285 | A1 | 6/2006 | Falloon et al. | EP | 0508141 | 10/1992 |
| 2006/0122863 | A1 | 6/2006 | Gottesman et al. | EP | 0568730 | 11/1993 |
| 2006/0142635 | A1 | 6/2006 | Forsell | EP | 0605302 | 7/1994 |
| 2006/0149124 | A1 | 7/2006 | Forsell | EP | 0 654 232 | 5/1995 |
| 2006/0149161 | A1 | 7/2006 | Wilson et al. | EP | 0660482 | 6/1995 |
| 2006/0149324 | A1 | 7/2006 | Mann et al. | EP | 0714017 | 5/1996 |
| 2006/0149327 | A1 | 7/2006 | Hedberg et al. | EP | 0769340 | 4/1997 |
| 2006/0157701 | A1 | 7/2006 | Bauer et al. | EP | 0846475 | 6/1998 |
| 2006/0161186 | A1 | 7/2006 | Hassler et al. | EP | 0848780 | 6/1998 |
| 2006/0178617 | A1 | 8/2006 | Adams et al. | EP | 0876808 | 11/1998 |
| 2006/0178695 | A1 | 8/2006 | Decant et al. | EP | 0888079 | 1/1999 |
| 2006/0183967 | A1 | 8/2006 | Lechner | EP | 0914059 | 5/1999 |
| 2006/0184206 | A1 | 8/2006 | Baker et al. | EP | 0981293 | 3/2000 |
| 2006/0189887 | A1 | 8/2006 | Hassler et al. | EP | 0997680 | 5/2000 |
| 2006/0189888 | A1 | 8/2006 | Hassler et al. | EP | 1003021 | 5/2000 |
| 2006/0189889 | A1 | 8/2006 | Gertner | EP | 1022983 | 8/2000 |
| 2006/0199997 | A1 | 9/2006 | Hassler, Jr. et al. | EP | 1050265 | 11/2000 |
| 2006/0211912 | A1 | 9/2006 | Dlugos et al. | EP | 1115329 | 7/2001 |
| 2006/0211913 | A1 | 9/2006 | Dlugos et al. | EP | 1119314 | 8/2001 |
| 2006/0211914 | A1 | 9/2006 | Hassler et al. | EP | 1128871 | 9/2001 |
| 2006/0217668 | A1 | 9/2006 | Schulze et al. | EP | 1202674 | 5/2002 |
| 2006/0217673 | A1 | 9/2006 | Schulze et al. | EP | 1213991 | 6/2002 |
| 2006/0235310 | A1 | 10/2006 | O'Brien et al. | EP | 1253877 | 11/2002 |
| 2006/0235439 | A1 | 10/2006 | Molitor et al. | EP | 1253879 | 11/2002 |
| 2006/0235448 | A1 | 10/2006 | Roslin et al. | EP | 1253880 | 11/2002 |
| 2006/0244914 | A1 | 11/2006 | Cech et al. | EP | 1253881 | 11/2002 |
| 2006/0247682 | A1 | 11/2006 | Gerber et al. | EP | 1253883 | 11/2002 |
| 2006/0247719 | A1 | 11/2006 | Maschino et al. | EP | 1253888 | 11/2002 |
| 2006/0247721 | A1 | 11/2006 | Maschino et al. | EP | 1255511 | 11/2002 |
| 2006/0247722 | A1 | 11/2006 | Maschino et al. | EP | 1255513 | 11/2002 |
| 2006/0247723 | A1 | 11/2006 | Gerber et al. | EP | 1255514 | 11/2002 |
| 2006/0247724 | A1 | 11/2006 | Gerber et al. | EP | 1263355 | 12/2002 |
| 2006/0247725 | A1 | 11/2006 | Gerber et al. | EP | 1263357 | 12/2002 |
| 2006/0252982 | A1 | 11/2006 | Hassler et al. | EP | 1284691 | 2/2003 |
| 2006/0293625 | A1 | 12/2006 | Hunt et al. | EP | 1374758 | 1/2004 |
| 2006/0293626 | A1 | 12/2006 | Byrum et al. | EP | 1442715 | 8/2004 |
| 2006/0293627 | A1 | 12/2006 | Byrum et al. | EP | 1488735 | 12/2004 |
| 2007/0010790 | A1 | 1/2007 | Byrum et al. | EP | 1500411 | 1/2005 |
| 2007/0027356 | A1 | 2/2007 | Ortiz | EP | 1510306 | 3/2005 |
| 2007/0027493 | A1 | 2/2007 | Ben-Haim et al. | EP | 1518514 | 3/2005 |
| 2007/0067206 | A1 | 3/2007 | Haggerty et al. | EP | 1545303 | 6/2005 |
| 2007/0070906 | A1 | 3/2007 | Thakur | EP | 1547549 | 6/2005 |
| 2007/0072452 | A1 | 3/2007 | Inagaki et al. | EP | 1563814 | 8/2005 |
| 2007/0081304 | A1 | 4/2007 | Takeguchi | | | |

| | | |
|---|---|---|
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1600120 | 11/2005 |
| EP | 1609440 | 12/2005 |
| EP | 1649884 | 4/2006 |
| EP | 1674033 | 6/2006 |
| EP | 1 676 527 | 7/2006 |
| EP | 1704833 | 9/2006 |
| EP | 1 736 123 | 12/2006 |
| EP | 1799119 | 6/2007 |
| GB | 2355937 | 5/2001 |
| JP | 2006/175191 | 7/2006 |
| WO | WO 89/11244 | 11/1989 |
| WO | WO 89/11701 | 11/1989 |
| WO | WO 90/04368 | 5/1990 |
| WO | WO 95/11057 | 4/1995 |
| WO | WO 97/15351 | 5/1997 |
| WO | WO 97/33513 | 9/1997 |
| WO | WO 98/33554 | 8/1998 |
| WO | WO 98/35610 | 8/1998 |
| WO | WO 99/01063 | 1/1999 |
| WO | WO 99/18850 | 4/1999 |
| WO | WO 00/04945 | 2/2000 |
| WO | WO 00/33738 | 6/2000 |
| WO | WO 00/72899 | 12/2000 |
| WO | WO 01/04487 | 1/2001 |
| WO | WO 01/12075 | 2/2001 |
| WO | WO 01/12076 | 2/2001 |
| WO | WO 01/12077 | 2/2001 |
| WO | WO 01/12078 | 2/2001 |
| WO | WO 01/21066 | 3/2001 |
| WO | WO 01/36014 | 5/2001 |
| WO | WO 01/45485 | 6/2001 |
| WO | WO 01/45486 | 6/2001 |
| WO | WO 01/47431 | 7/2001 |
| WO | WO 01/47432 | 7/2001 |
| WO | WO 01/47433 | 7/2001 |
| WO | WO 01/47434 | 7/2001 |
| WO | WO 01/47435 | 7/2001 |
| WO | WO 01/47440 | 7/2001 |
| WO | WO 01/47575 | 7/2001 |
| WO | WO 01/48451 | 7/2001 |
| WO | WO 01/49245 | 7/2001 |
| WO | WO 01/50832 | 7/2001 |
| WO | WO 01/50833 | 7/2001 |
| WO | WO 01/54626 | 8/2001 |
| WO | WO 01/58388 | 8/2001 |
| WO | WO 01/58390 | 8/2001 |
| WO | WO 01/58391 | 8/2001 |
| WO | WO 01/58393 | 8/2001 |
| WO | WO 01/60453 | 8/2001 |
| WO | WO 01/81890 | 11/2001 |
| WO | WO 02/00118 | 1/2002 |
| WO | WO 02/15769 | 2/2002 |
| WO | WO 02/053228 | 7/2002 |
| WO | WO 02/055126 | 7/2002 |
| WO | WO 02/058551 | 8/2002 |
| WO | WO 02/065894 | 8/2002 |
| WO | WO 02/076289 | 10/2002 |
| WO | WO 02/082984 | 10/2002 |
| WO | WO 02/089655 | 11/2002 |
| WO | WO 02/090894 | 11/2002 |
| WO | WO 02/100481 | 12/2002 |
| WO | WO 03/002192 | 1/2003 |
| WO | WO 03/002193 | 1/2003 |
| WO | WO 03/020182 | 3/2003 |
| WO | WO 03/043534 | 5/2003 |
| WO | WO 03/061467 | 7/2003 |
| WO | WO 03/061504 | 7/2003 |
| WO | WO 03/096889 | 11/2003 |
| WO | WO 2004/014245 | 2/2004 |
| WO | WO 2004/014456 | 2/2004 |
| WO | WO 2004/019773 | 3/2004 |
| WO | WO 2004/030541 | 4/2004 |
| WO | WO 2004/058101 | 7/2004 |
| WO | WO 2004/066879 | 8/2004 |
| WO | WO 2004/110263 | 12/2004 |
| WO | WO 2005/000206 | 1/2005 |
| WO | WO 2005/007075 | 1/2005 |
| WO | WO 2005/027998 | 3/2005 |
| WO | WO 2005/084544 | 9/2005 |
| WO | WO 2005/107583 | 11/2005 |
| WO | WO 2006/001851 | 1/2006 |
| WO | WO 2006/018927 | 2/2006 |
| WO | WO 2006/035446 | 4/2006 |
| WO | WO 2006/113187 | 10/2006 |
| WO | WO 2006/122285 | 11/2006 |
| WO | WO 2007/067206 | 6/2007 |
| WO | WO 2007/070906 | 6/2007 |
| WO | WO 2007/072452 | 6/2007 |
| WO | WO 2007/081304 | 7/2007 |
| WO | WO 2007/104356 | 9/2007 |
| WO | WO 2007/140430 | 12/2007 |
| WO | WO 2008/088949 | 7/2008 |

OTHER PUBLICATIONS

EPO Search Report dated Jul. 23, 2007, for EP Application No. 07250932.6.
U.S. Appl. No. 12/039,014, filed Feb. 28, 2008, Dlugos, Jr. et al.
EP Search Report dated Jun. 13, 2007 for Application No. 07250931.
EP Search Report dated Jun. 18, 2007 for Application No. 07250932.
Kirchner, G., "Honeywell and Synopsys: Concept-to-Parts Solutions for Next Generation Rad-Hard ASICs," in online magazine Compiler, http://www.synopsys.com/news/pubs/compiler/artlead_redasic-apr05.html,(Apr. 2005), pp. 1-5.
Neukomm, P.A. et al., "Passive Wireless Actuator Control and Sensor Signal Transmission," Sensors and Actuators, A21-A23 (1990) pp. 258-262.
Lechner, W., "In Vivo Band Manometry: a New Access to Band Adjustment," Obesity Surgery, vol. 15 (2005) pp. 1432-1436.
European Search Report dated May 2, 2008 for Application No. EP 06250968.
European Examination Report dated Dec. 9, 2008 for Application No. EP 06250968.
European Search Report dated Nov. 3, 2008 for Application No. EP 08251508.
European Examination Report dated Jul. 23, 2007 for Application No. EP 06253286.
European Search Report dated Sep. 28, 2006 for Application No. EP 06253286.
European Search Report dated Feb. 10, 2009 for Application No. EP 07250915.
Abstract for JP2006/175191.
European Search Report dated Jun. 19, 2009 for Application No. 09250581.
European Search Report dated Jul. 10, 2009 for Application No. 09250590.
European Search Report dated Jul. 10, 2009 for Application No. 09250600.
European Search Report dated Aug. 13, 2009 for Application No. 08251093.
International Search Report and Written Opinion dated Sep. 22, 2008 for Application No. PCT/US2008/053394.

* cited by examiner

SYSTEM AND METHOD FOR DETERMINING IMPLANTED DEVICE ORIENTATION

PRIORITY

This application is a continuation-in-part of prior co-pending U.S. Non-Provisional application Ser. No. 11/369,682, filed Mar. 7, 2006, entitled "System and Method for Determining Implanted Device Positioning and Obtaining Pressure Data," and published as U.S. Pub. No. 2006/0211914; which is a continuation-in-part of prior co-pending U.S. Non-Provisional application Ser. No. 11/065,410, filed Feb. 24, 2005, entitled "Device for Non-Invasive Measurement of Fluid Pressure in an Adjustable Restriction Device," published as U.S. Pub. No. 2006/0189888. The disclosure of each of those applications and publications is incorporated by reference herein.

BACKGROUND

Many devices and methods for treating obesity have been made and used, including but not limited to adjustable gastric bands. An example of such an adjustable gastric band is disclosed in U.S. Pat. No. 6,067,991, entitled "Mechanical Food Intake Restriction Device" which issued on May 30, 2000, and which is incorporated herein by reference. Some fluid-based adjustable gastric band systems include an implanted port for the injection and withdrawal of fluid from the gastric band system. Insertion of a needle, or otherwise engaging a port, may be difficult in some situations where the port is oriented within a patient in certain ways (e.g., when a port is flipped upside-down). The foregoing examples are merely illustrative and not exhaustive. While a variety of techniques and devices have been used treat obesity, it is believed that no one prior to the inventors has previously made or used an invention as described in the appended claims.

BRIEF DESCRIPTION OF THE FIGURES

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
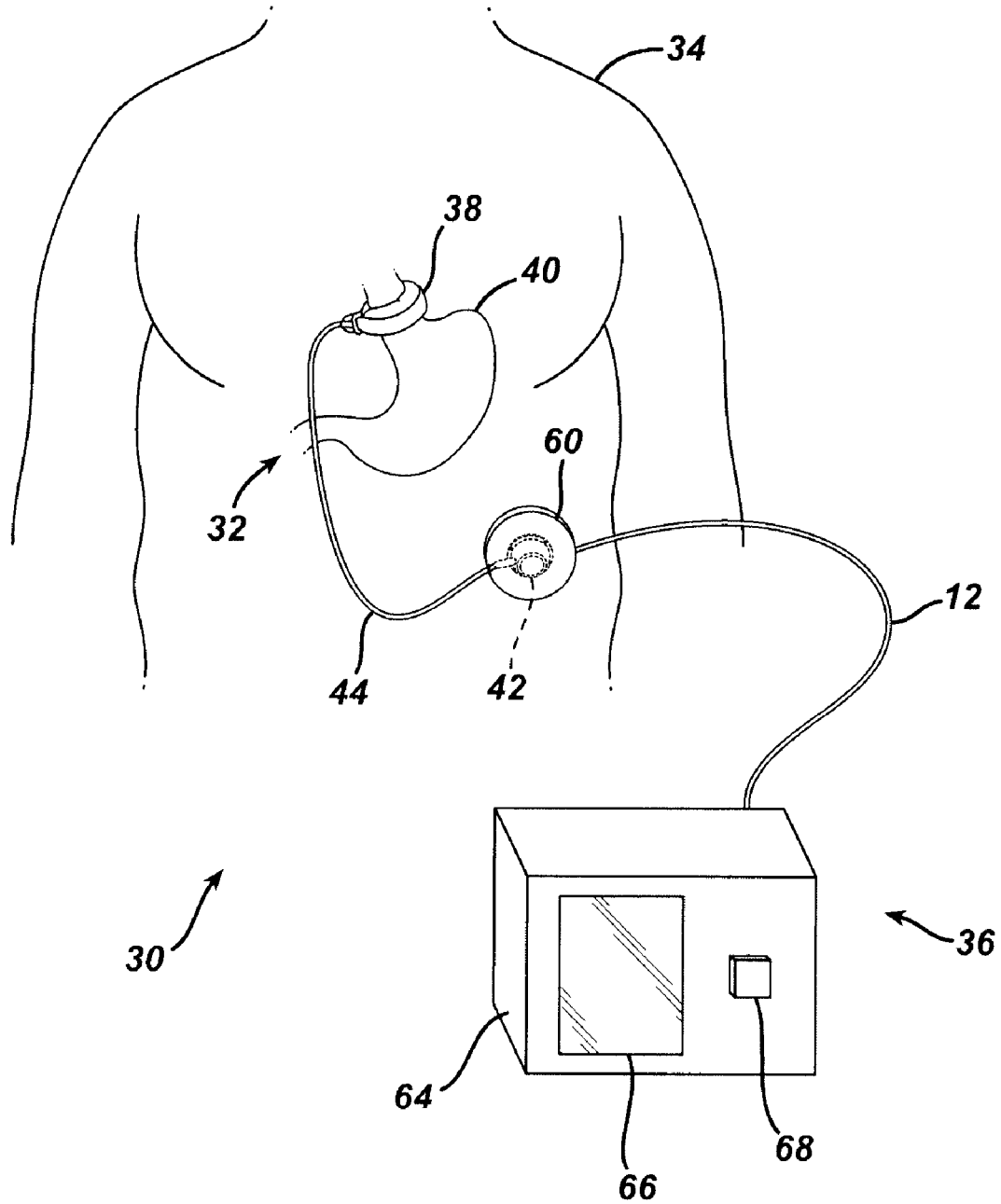
FIG. 1 is a schematic illustration of an exemplary food intake restriction device.

Referring now to the drawings in detail, wherein like numerals indicate the same elements throughout the views, FIG. 1 illustrates a food intake restriction system 30. System 30 comprises a first portion, identified generally as 32, implanted inside of a patient 34, and a second portion, identified generally as 36, located external to the patient. Implanted portion 32 comprises an adjustable gastric band 38 positioned on the upper portion of the patient's stomach 40. Adjustable band 38 may include a cavity made of silicone rubber, or another type of biocompatible material, that inflates inwardly against stomach 40 when filled with a fluid. Alternatively, band 38 may comprise a mechanically adjustable device having a fluid cavity that experiences pressure changes with band adjustments, or a combination hydraulic/mechanical adjustable band. An injection port 42, which will be described in greater detail below, is implanted in a body region accessible for needle injections and/or telemetry communication signals. In the embodiment shown, injection port 42 fluidly communicates with adjustable band 38 via a catheter 44. A surgeon may position and permanently implant injection port 42 inside the body of the patient in order to perform adjustments of the food intake restriction or stoma. Those skilled in the art will recognize that the surgical methods for placing gastric band systems such as implantable portion 32 have evolved greatly during recent years so that the patient may derive optimal therapeutic effect with minimal complications. The surgeon, for example, typically implants injection port 42 in the lateral, subcostal region of the patient's abdomen under the skin and layers of fatty tissue. The surgeon may also implant injection port 42 on the sternum of the patient.

Figure 2:
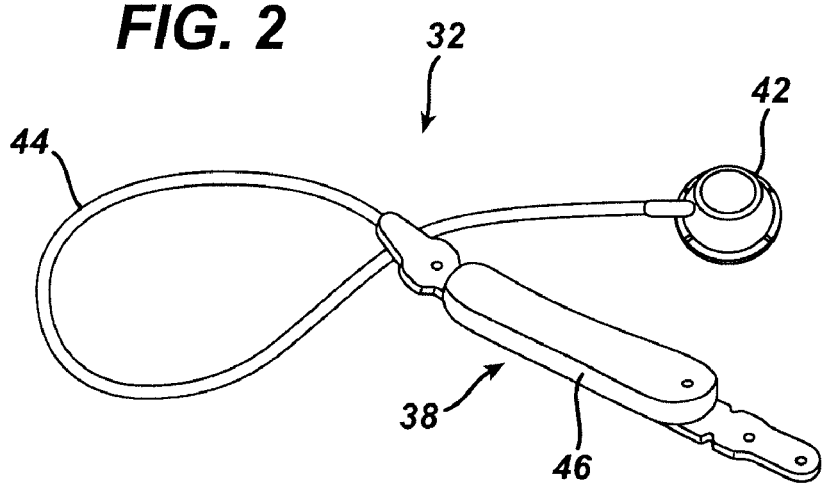
FIG. 2 is a more detailed perspective view of an exemplary implantable portion for the food intake restriction device of FIG. 1.

FIG. 2 illustrates an exemplary adjustable gastric band in greater detail. In this embodiment, band 38 includes a variable volume cavity 46 that expands or contracts against the outer wall of the stomach to form an adjustable stoma for controllably restricting food intake into the stomach. A physician may decrease the size of the stoma opening by adding fluid to variable volume cavity 46 or, alternatively, may increase the stoma size by withdrawing fluid from the cavity. Fluid may be added or withdrawn by inserting a needle into injection port 42. Alternatively, fluid may be transferred in a non-invasive manner between band 38 and injection port 42 using telemetry command signals. The fluid may be, but is not restricted to, a 0.9 percent saline solution.

Figure 3:
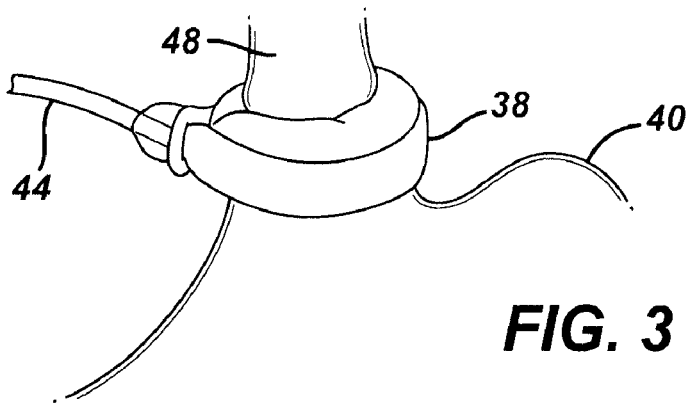
FIG. 3 is a perspective view of the adjustable gastric band of FIG. 2, showing the band positioned around the gastro-esophageal junction of a patient.
Figure 4:
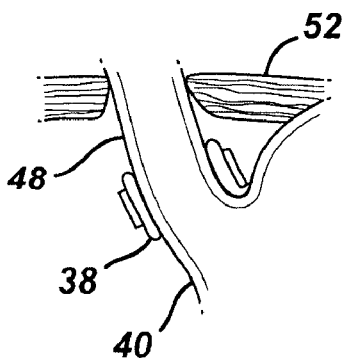
FIG. 4 is a cross-sectional view of the adjustable gastric band of FIG. 2, shown in a deflated configuration.
Figure 5:
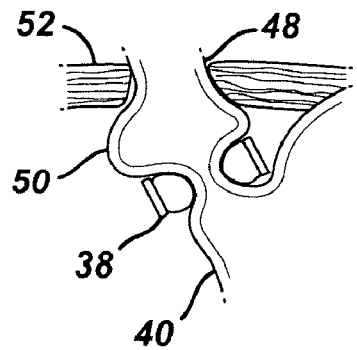
FIG. 5 is a cross-sectional view of the adjustable gastric band of FIG. 2, shown in an inflated configuration to create a food intake restriction.

FIG. 3 shows the adjustable gastric band 38 of FIG. 2 applied about the gastro-esophageal junction of a patient. As shown in FIG. 3, band 38 at least substantially encloses the upper portion of stomach 40 near the junction with esophagus 48. FIG. 4 is a sectional view of band 38, showing the band in a deflated configuration. In this view, band 38 contains little to no fluid, thereby maximizing the size of the stoma opening into stomach 40. FIG. 5 is a cross-sectional view of band 38 and stomach 40, similar to FIG. 4, showing band 38 in an inflated, fluid-filled configuration. In this view, the pressure of band 38 against stomach 40 is increased due to the fluid within the band, thereby decreasing the stoma opening to create a food intake restriction. FIG. 5 also schematically illustrates the dilation of esophagus 48 above band 38 to form an upper pouch 50 beneath the diaphragm muscle 52 of the patient.

Returning now to FIG. 1, external portion 36 of food restriction system 30 comprises a pressure-reading device 60 electrically connected (in this embodiment via an electrical cable assembly 62) to a control box 64. Control box 64 includes a display 66, one or more control switches 68, and an external control module, which will be explained in further detail below. Control box 64 may be configured for use, for example, in a physician's office or examination room. Some ways to mount control box 64 include placement upon a desktop, attachment to an examination table, or hanging on a portable stand. Control box 64 may also be configured for carrying in the physician's lab coat pocket, holding by hand, or placing upon the examination table or the reclining patient. Electrical cable assembly 62 may be detachably connected to control box 64 or pressure-reading device 60 to facilitate cleaning, maintenance, usage, and storage of external portion 36 of system 30. Pressure-reading device 60 non-invasively measures the pressure of the fluid within implanted portion 32 even when injection port 42 is implanted beneath thick (at least over 10 centimeters) subcutaneous fat tissue. The physician may hold pressure-reading device 60 against the patient's skin near the location of injection port 42 in the patient and observe the pressure reading on display 66 of control box 64. Pressure-reading device 60 may also be removably attached to the patient, such as during a prolonged examination, using straps, adhesives, and other well-known methods. Pressure-reading device 60 operates through conventional cloth or paper surgical drapes, and may also include a disposal cover (not shown) that may be replaced for each patient.

Figure 6:
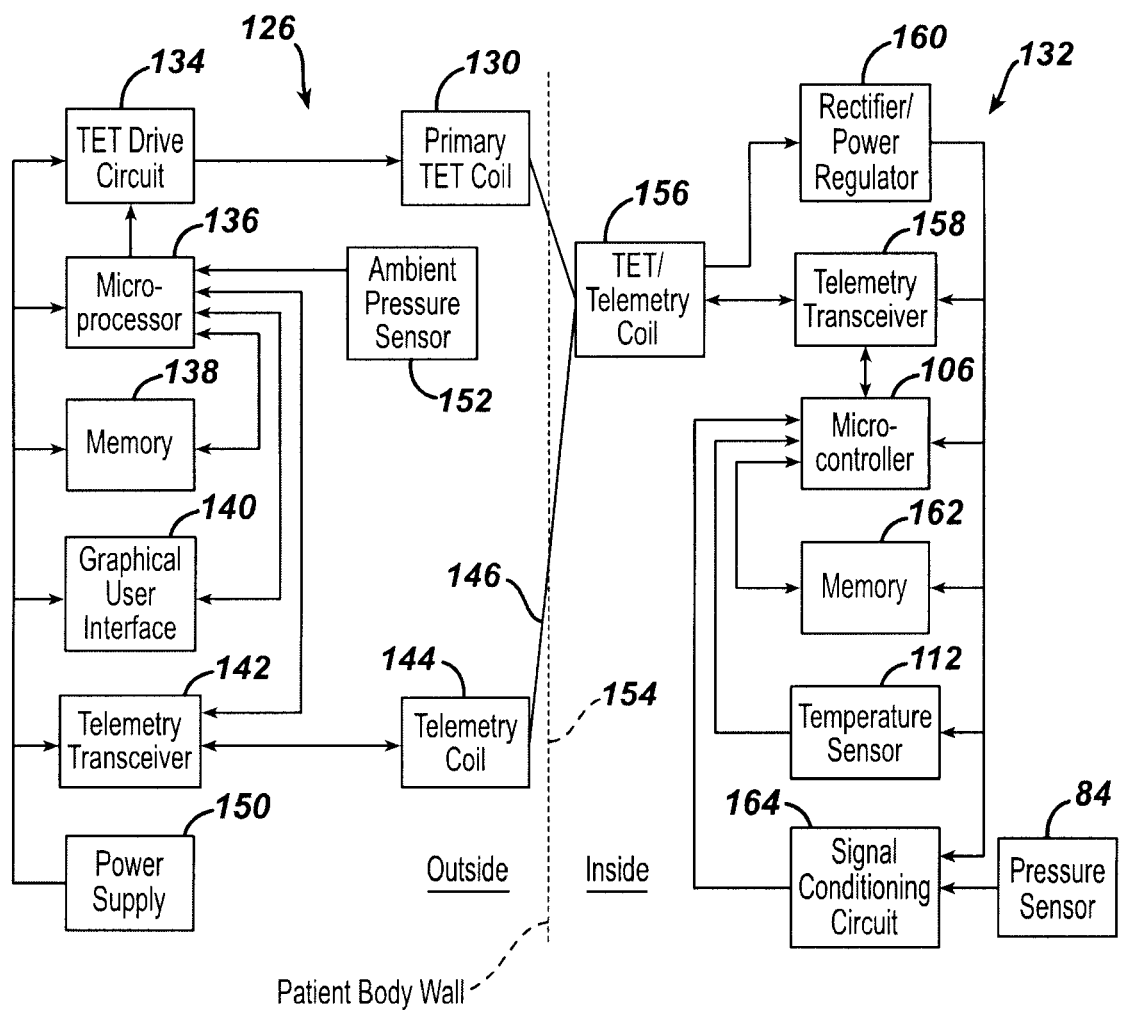
FIG. 6 is a block diagram representing an exemplary pressure measurement system.

FIG. 6 is a block diagram of an exemplary pressure measurement system consistent with embodiments described in greater detail below. As shown in FIG. 6, an external control module 126 of the system includes a primary TET coil 130 for transmitting a power signal to the internal control module, indicated generally as 132. Primary TET coil 130 is located in pressure reading device 60 shown in FIG. 1. A TET drive circuit 134 controls the application of a power signal to primary TET coil 130. TET drive circuit 134 is controlled by a microprocessor 136 having an associated memory 138. A graphical user interface 140 is connected to microprocessor 136 for controlling the data shown on display 66. External control module 126 also includes a primary telemetry transceiver 142 for transmitting interrogation commands to and receiving response data, including fluid pressure readings, from implant control module 132 via telemetry coil 144.

While TET coil 130 and telemetry coil 144 are shown as separate coils, it will be appreciated that functions of TET and telemetry may alternatively be provided by the same coil or by one or more other structures. In this example, primary transceiver 142 is electrically connected to microprocessor 136 for inputting and receiving command and data signals. Primary transceiver 142 resonates at a selected RF communication frequency to generate a downlink alternating magnetic field 146 that transmits command data to implant control module 132. A power supply 150 supplies energy to external control module 126 in order to power system 30. An ambient pressure sensor 152 is connected to microprocessor 136. Microprocessor 136 uses the signal from ambient pressure sensor 152 to adjust the pressure reading for variations in atmospheric pressure due to, for example, variations in barometric conditions or altitude, in order to increase the accuracy of the pressure measurement. Of course, all of these components are merely exemplary, and any of these components may be omitted, substituted, supplemented, or rearranged as desired.

Figure 12:
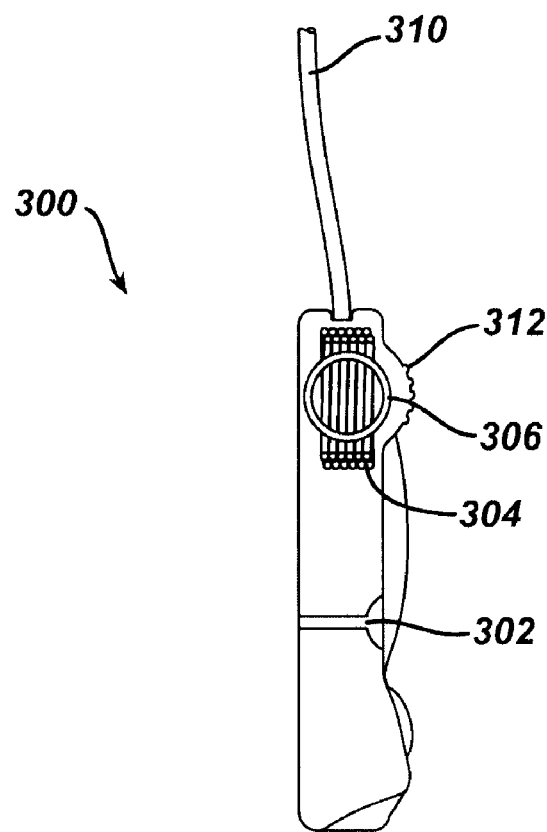
FIG. 12 is a side, cross-sectional view of the sense head of FIG. 11, taken along line 12-12.
Figure 13:
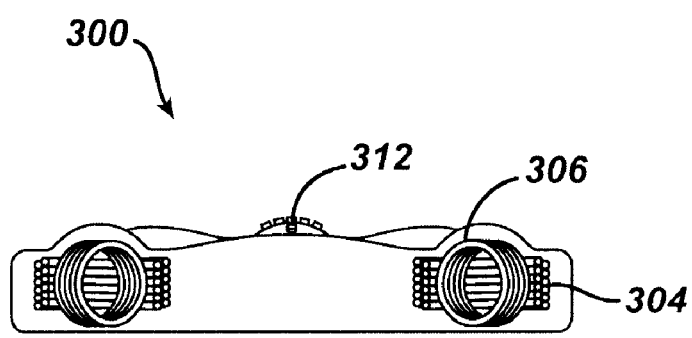
FIG. 13 is a side, cross-sectional view of the sense head of FIG. 11, taken along line 13-13.

FIG. 6 also illustrates internal control module 132 implanted beneath the patient's skin 154. Internal control module 132 is located within injection port 42 in this example. As shown in FIG. 12, a secondary TET/telemetry coil 156 in internal control module 132 receives power and communication signals from external control module 126. Coil 156 forms a tuned tank circuit that is inductively coupled with either primary TET coil 130 to power the implant, or primary telemetry coil 144 to receive and transmit data. A telemetry transceiver 158 controls data exchange with coil 156. Additionally, internal control module 132 includes a rectifier/power regulator 160, microcontroller 106 described above, a memory 162 associated with the microcontroller, temperature sensor 112, pressure sensor 84 and a signal conditioning circuit 164 for amplifying the signal from the pressure sensor. Internal control module 132 transmits the temperature adjusted pressure measurement from pressure sensor 84 to external control module 126. In external module 126, the received pressure measurement signal is adjusted for changes in ambient pressure and shown on display 66. Again, though, these components are merely exemplary, and any of these components may be omitted, substituted, supplemented, or rearranged as desired.

Figure 7:
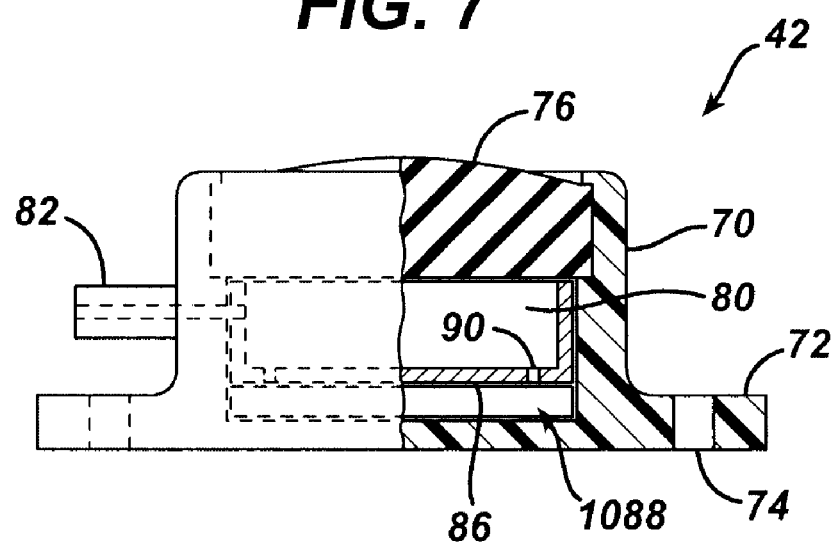
FIG. 7 is a side, partially cross-sectioned view of the injection port shown in FIG. 2.

Turning now to FIG. 7, which depicts a side, partially sectioned view of injection port 42 containing a pressure sensing system for non-invasively measuring the fluid pressure within implanted portion 32. As shown in FIG. 7, injection port 42 comprises a rigid housing 70 having an annular flange 72 containing a plurality of attachment holes 74 for fastening the injection port to tissue in a patient. A surgeon may attach injection port 42 to the tissue, such as the fascia covering an abdominal muscle, using any one of numerous surgical fasteners including suture filaments, staples, and clips. Injection port 42 further comprises a septum 76 typically made of a silicone rubber and compressively retained in housing 70. Septum 76 is penetrable by a Huber needle, or a similar type of injection instrument, for adding or withdrawing fluid from the port. Septum 76 self-seals upon withdrawal of the syringe needle to maintain the volume of fluid inside of injection port 42.

Injection port 42 of the present example further comprises a reservoir 80 for retaining a working fluid and a catheter connector 82. Connector 82 attaches to catheter 44, shown in FIG. 2, to form a closed hydraulic circuit between reservoir 80 inside of injection port 42 and cavity 46 within adjustable band 38. Fluid from reservoir 80 may be used to expand the volume of band cavity 46. Alternatively, fluid may be removed from cavity 46 and retained in reservoir 80 in order to temporarily decrease the volume of cavity 46. Housing 70 and connector 82 may be integrally molded from a biocompatible polymer, constructed from a metal such as titanium or stainless steel, or be made from any other suitable material(s).

In one embodiment, described in greater detail below, a pressure sensing system is provided in injection port 42 to measure the fluid pressure within the closed hydraulic circuit of implanted portion 32. The pressure within the circuit may correspond to the amount of restriction applied by adjustable band 38 to the patient's stomach. Accordingly, measuring the fluid pressure may enable a physician to evaluate the restriction created by a band adjustment. Fluid pressure may be measured before, during, and/or after an adjustment to verify that the band is properly adjusted. In the embodiment shown in FIG. 7, the pressure sensing system comprises a sensor system 1088 positioned at the bottom of fluid reservoir 80 within housing 70. A retaining cover 86 extends above sensor system 1088 to substantially separate the sensor system 1088 from reservoir 80, and to protect components of the sensor system 1088 from needle penetration. Retaining cover 86 may be made of a ceramic material such as, for example, alumina, which resists needle penetration yet does not interfere with electronic communications between sensor system 1088 and pressure-reading device 60. Retaining cover 86 includes a vent 90 that allows fluid inside of reservoir 80 to flow to and impact upon the surface of sensor system 1088.

Figure 8:
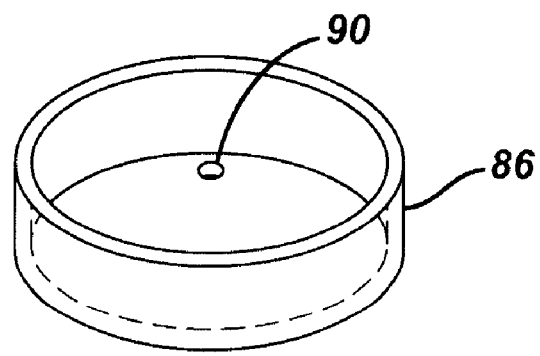
FIG. 8 is an isometric view of the retaining cover shown in FIG. 7.

FIG. 8 is an isometric view of retaining cover 86 illustrating vent 90 in the bottom surface of the cover. Housing 94 is sealed to port housing 70 to prevent the loss of fluid from the injection port 42. As fluid flows through vent 90 in reservoir 80, the fluid impacts upon the surface of sensor system 1088. The fluid flow through vent 90 enables sensor system 1088 to respond to fluid pressure changes within the hydraulic circuit and convert the pressure changes into a usable form of data.

Figure 9:
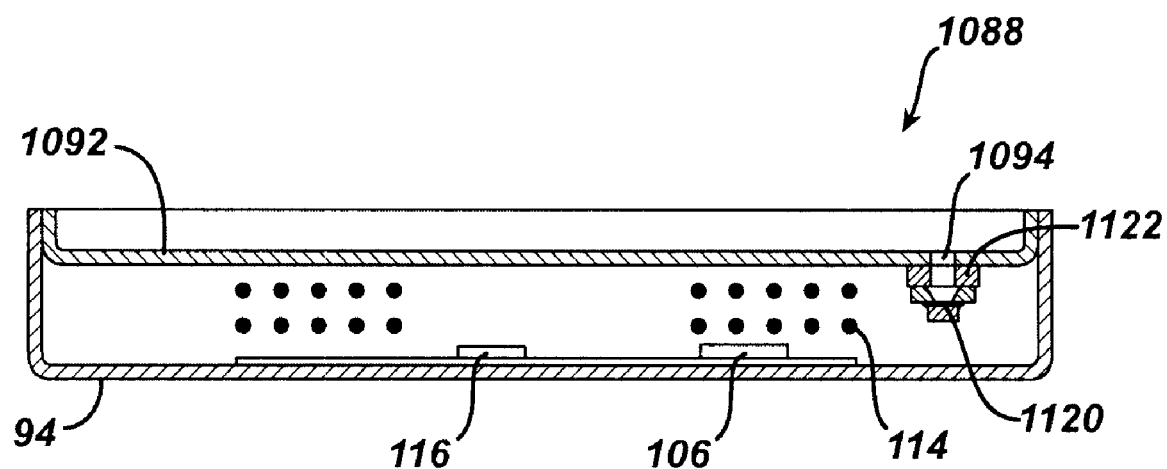
FIG. 9 is a side cross-sectional view illustrating an exemplary pressure sensing system incorporated into the injection port shown in FIG. 2.
Figure 10:
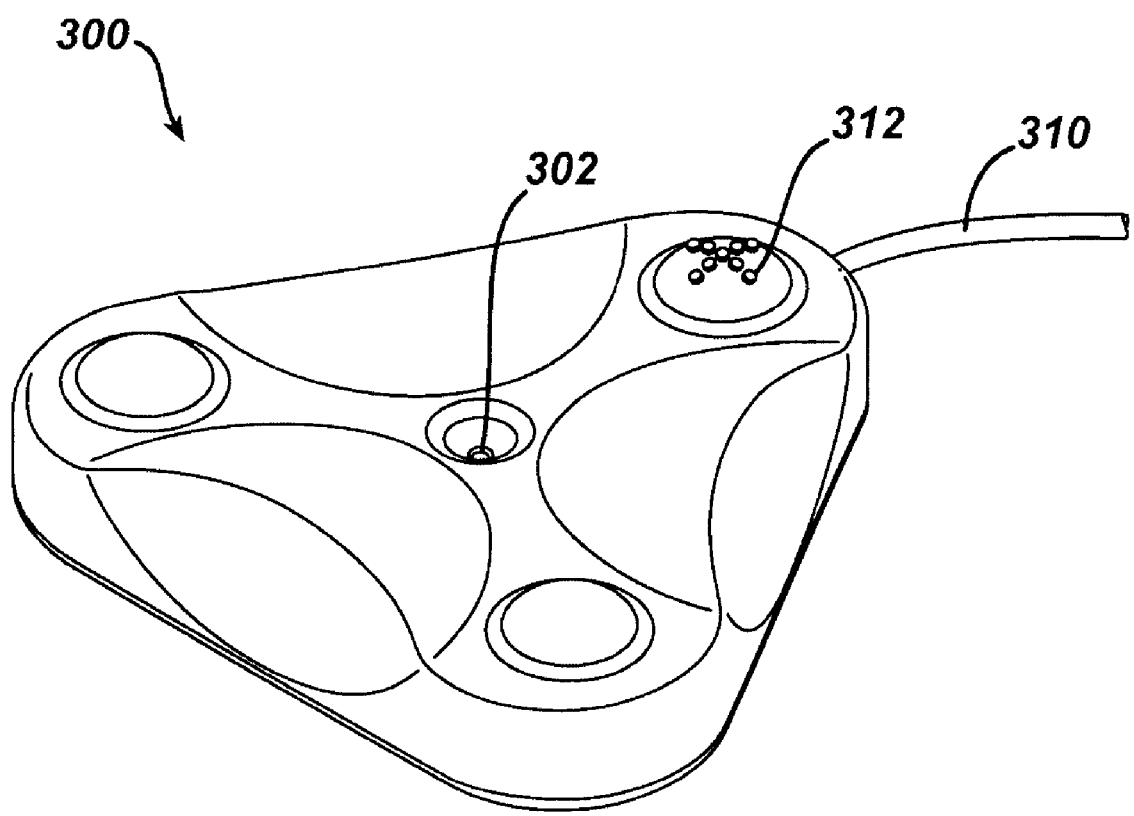
FIG. 10 is a perspective view of an exemplary sense head.
Figure 11:
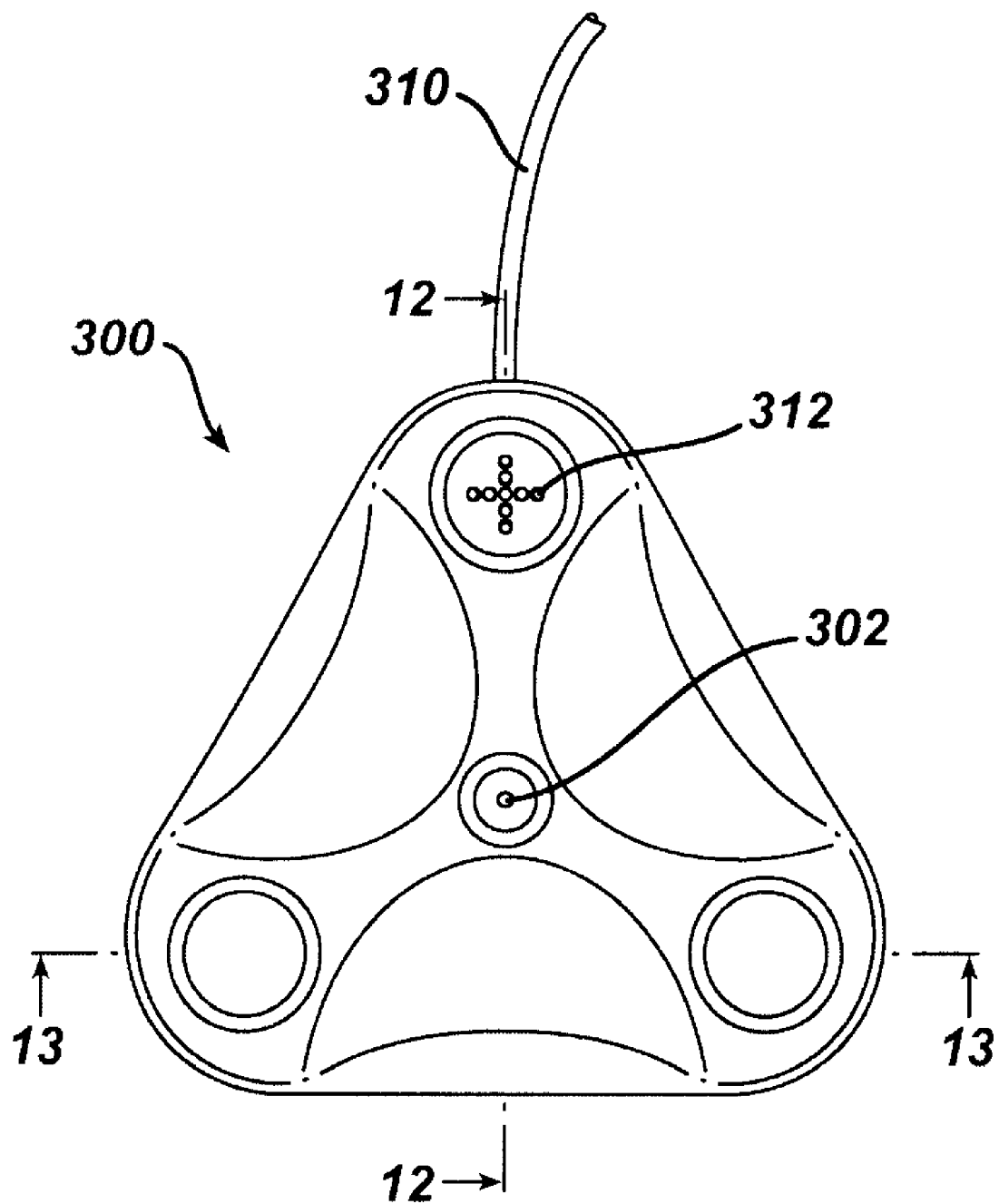
FIG. 11 a plan view of the sense head of FIG. 10.

An exemplary sensor system 1088 suitable for incorporation into port 42 is shown in FIG. 9. In this example, pressure sensing system 1088 comprises an upper member 1092 and a housing 94. Pressure sensing system 1088 may be positioned beneath retaining cover 86 of port 42. Alternatively, upper member 1092 may be integral with retaining cover 86, such that upper member 1092 provides a bottom for retaining cover 86 or reservoir 80. Other suitable configurations will be apparent to those of ordinary skill in the art. In the present example, upper member 1092 is in fluid communication with fluid located within port 42, such that the pressure of such fluid is exerted against upper member 1092. Pressure sensing system 1088 further comprises a microcontroller 106, a TET/telemetry coil 114, and a capacitor 116. Optionally, pressure sensing system 1088 may further comprise a temperature sensor (not shown). Microcontroller 106, TET/telemetry coil 114, and capacitor 116 may be in communication via a circuit board (not shown) or any via any other suitable component(s). It will also be appreciated that TET/telemetry coil 114 and capacitor 116 may collectively form a tuned tank circuit for receiving power from external portion 36, and transmitting the pressure measurement to pressure reading device 60.

In the embodiment of pressure sensing system 1088 depicted in FIG. 9, a fluid access port 1094 is provided in upper member 1092, and is in fluid communication with a pressure sensor 1120. A hermetic seal 1122 secures pressure sensor 1120 to the bottom of upper member 1092. Pressure sensor 1120 is configured to sense pressure of fluid adjacent to upper member 1092, which is communicated to pressure sensor 1120 via fluid access port 1094. Pressure sensor 1120 is further in communication with microcontroller 106, such that pressure measurements obtained using pressure sensor 1120 may be communicated to or through microcontroller 106 and thus via coil 114 to an external telemetry device (e.g., pressure reading device 60).

In one embodiment, pressure sensor 1120 comprises a wireless pressure sensor provided by CardioMEMS, Inc. of Atlanta, Ga., though a suitable MEMS pressure sensor may be obtained from any other source, including but not limited to Integrated Sensing Systems (ISSYS), and Remon Medical. In one example, MEMS pressure sensor 1120 comprises a pressure sensor described in U.S. Pat. No. 6,855,115, the disclosure of which is incorporated by reference herein for illustrative purposes only. It will also be appreciated that suitable pressure sensors may include, but are not limited to, capacitive, piezoresistive, silicon strain gauge, or ultrasonic (acoustic) pressure sensors.

It will be appreciated that pressure sensor 1120 may be configured to wirelessly communicate pressure data to an external telemetry device using a variety of structures and techniques. By way of example only, telemetry may be provided using RF, ultrawideband (UWB), ultrasonics, or any other suitable way of communicating. It will also be appreciated that any protocol (e.g., Bluetooth, etc.) within any modality of communication may be used. Accordingly, pressure sensor 1120 may comprise a telemetry component (e.g., a coil, a transmitter, etc.), or may be in communication with another telemetry component (e.g., coil 114). To the extent that a telemetry component of pressure sensor 1120 is unable to reach a telemetry device external to patient 34 without some assistance, such assistance may provided by any suitable number of relays (not shown) or other devices.

It will also be appreciated that sensor system 1088 depicted in FIG. 9 may provide functionality similar to internal control module 132 described above and depicted in FIG. 6. For instance, coil 114 of sensor system 1088 may be configured and operable in a manner similar to TET/telemetry coil 156 of internal control module 132. Similarly, pressure sensor 1120 of sensor system 1088 may be configured and operable in a manner similar to pressure sensor 84 of internal control module 132. In addition, microcontroller 106 of sensor system 1088 may be configured and operable in a manner similar to microcontroller 106 of internal control module 132. Other ways in which internal control module 132 components illustrated in FIG. 6, or variations of such components, may be incorporated into sensor system 1088 will be apparent to those of ordinary skill in the art.

While sensor system 1088 has been described herein as an exemplary sensor system, it will be appreciated that any other type of sensor system may be used in any suitable location. Suitable alternative sensor systems, as well as other suitable sensor system locations (e.g., somewhere external to an injection port), are described in many of the various patents, patent applications, and patent publications that have been referred to and incorporated by reference herein. Still other sensor system variations will be apparent to those of ordinary skill in the art. Furthermore, it is contemplated that some alternative embodiments may lack a sensor system altogether.

FIGS. 10-13 show an exemplary sense head 300, which is operable to externally sense the location and orientation of port 42. Sense head 300 of this example comprises a needle window 302, a set of horizontal coils 304, a set of vertical coils 306, a TET coil (not shown), and a cable 310. The TET coil is wrapped around a generally triangular bobbin (not shown), though any other configuration may be used. In the present example, the TET coil is tuned in parallel with a low ESR capacitor at 50 kHz to form a parallel tuned tank circuit. Coil 114 of port 42 is tuned in series with capacitor 116 such that the resonant impedance is minimized at a resonant frequency of 50 kHz. With an input power of 5 W on the TET coil, coil 114 may deliver approximately 10 mW of power. Of course, any other configurations and parameters may be used.

Each vertical coil 306 of sense head 300 is positioned perpendicularly within a corresponding horizontal coil 304. While three horizontal coils 304 and three vertical coils 306 are shown, it will be appreciated that any suitable number of coils 304, 306 may be used. In addition, while the coils 304, 306 are shown as being in a generally triangular arrangement, it will be appreciated that any other suitable arrangement or configuration may be used. Cable 310 is in communication with coils 304, 306, and is further in communication with a display device 350 as will be described in greater detail below. Of course, sense head 300 may be in communication with any other external device via wire, wirelessly, or otherwise.

Sense head 300 of the present example is configured to communicate with an injection port, such as injection port 42 by way of example only. It will be appreciated that sense head 300 may communicate with any other injection port or other device, including but not limited to alternative ports described herein and variations thereof. It will be understood, however, that with some embodiments, the type or amount of metal within a port 42 may have an adverse effect on operation of the port 42 and/or sense head 300. For instance, such effects may be in the form of undesirable eddy currents, to the extent that eddy currents are undesirable. To the extent that a metal port 42 housing provides undesirable results it will be appreciated that a coil 114 may be positioned outside of such metal and hermetically wired to a pressure sensor 87 or to other port components. However, such measures are not necessary with port 42 of the present example.

In the present example sense head 300 is operable to provide power to port 42 via the TET coil. Sense head 300 is also operable to detect the position and orientation of port 42, as will be described in greater detail below. Furthermore, sense head 300 is operable to receive pressure data and other data communicated from port 42 in a manner similar to pressure reading device 60, described above. In other words, in one embodiment, sense head 300 provides the same functionalities and serves the same purposes as pressure reading device 60 described above. For instance, a coil within sense head 300 (e.g., any one or more of coils 304, 306) may receive communications from coil 114 indicating pressure data obtained by pressure sensor 1120. Sense head 300 may thus provide a coil that is configured and operable like the telemetry coil 144 shown in FIG. 6 and described above. Alternatively, sense head 300 may lack such functionality, or may otherwise be used in a manner that does not include receiving pressure data.

While location, orientation, and pressure-related communications will be described in greater detail below, those of ordinary skill in the art will appreciate that any other types of information may be communicated between port 42 and sense head 300 in any other suitable manner. It will also be appreciated that sense head 300 need not necessarily be used to obtain any or all of location, orientation, and/or pressure-related communications.

In one exemplary use, sense head 300 is placed adjacent to a patient 34 in a region generally near port 42. As will be described in greater detail below, sense head 300 may be used to determine the location and orientation of port 42, thereby permitting a user to position sense head 300 directly over or sufficiently near port 42. When sense head 300 is so positioned, the user may insert a needle 430 of syringe 400 through needle guide 302 of sense head 300 and reach septum 76 of port 42 on the first try. The user may then use syringe 400 to adjust the pressure of fluid within implanted portion 32.

With sense head 300 placed in an initial position, horizontal coils 304 are configured to sense an RF signal provided by coil 114 in port 42. It will be appreciated that characteristics of such RF signal may vary as a function of the position of sense head 300 relative to port 42. Display device 350, which will be described in greater detail below with reference to FIGS. 20-23, may receive indications of such RF signals from each horizontal coil 304, and may process these signals through a logic operable to compare the signal picked up at each horizontal coil 304. Sense head 300 may thus be used to determine the position of port 42 through triangulation. For instance, when sense head 300 is positioned directly over port 42, the three received signals may have an approximately equal amplitude, and a phase shift of approximately zero. It will be appreciated, however, that it may not be possible to position sense head 300 such that the RF signal sensed at each horizontal coil 304 has equal amplitude and a zero phase shift relative to the RF signal as sensed at the other horizontal coils 304. Accordingly, sense head 300 may be moved around adjacent patient 34 until the differences between the amplitudes and phases of the RF signals sensed at horizontal coils 304 are minimized.

As will be described in greater detail below, a display device 350 may further comprise a logic operable to provide a visual representation to the user indicating the relative positioning of sense head 300 and port 42, and further provide a particular indication when sense head 300 is positioned directly over port 42.

Sense head 300 may further comprise a feature operable to visually display location information. In the present example, sense head 300 comprises a plurality of LEDs 312, which are arranged in a "plus sign"-like configuration. LEDs 312 may provide a visual indication to the user as to the relative positioning of sense head 300 and port 42. In particular, lit LEDs 312 may represent position of port 42 relative to sense head 300. For instance, if sense head 300 needs to be moved down and to the right in order to be positioned directly over port 42, the right-most and lower-most LEDs 312 may be lit. As sense head 300 is moved closer to being located directly over port 42, LEDs may provide feedback indicating such proximity as sense head 300 is moved, until the center LED 312 is lit to indicate that sense head 300 is positioned generally over port 42. When the center LED 312 is lit, the user may then desire to refer to display device 350, as will be described in greater detail below, to further adjust positioning of sense head 300.

To the extent that LEDs 312 are used, such LEDs 312 may be arranged in any suitable configuration other than a "plus sign." Such alternative configurations may comprise a Cartesian representation, a polar representation, a numerical representation, or any other type of representation. By way of example only, a star or compass rose configuration may be used. In another embodiment, an array of LEDs 312 are provided, and are operable to be selectively lit in the form of an arrow indicating direction. The length of such an arrow may further be varied to indicate distance. It will also be appreciated that additional LEDs 312 may be used to increase spatial resolution of distance and/or direction indicated by such LEDs 312. Of course, any suitable alternative to LEDs 312 may be used, including but not limited to an LCD screen or other display. Alternatively, a sense head 300 may lack LEDs 312 or any substitute therefor.

In one embodiment, a logic configured to process signals received by horizontal coils 304 to provide positioning feedback through LEDs 312 resides within sense head 300. In another embodiment, such logic resides in display device 350, and is communicated to LEDs 312 in part through cable 310. In still another embodiment, the logic for driving LEDs 312 resides within both sense head 300 and display device 350. Still other suitable locations for logic to drive LEDs 312, and other ways in which LEDs 312 may be driven, will be apparent to those of ordinary skill in the art. It will also be appreciated that, as with any other component and feature described herein, LEDs 312 may simply be omitted altogether.

With sense head 300 placed in an initial position adjacent to a patient 34 in a region generally near port 42, vertical coils 306 configured to sense an RF signal provided by coil 114 in port 42. It will be appreciated that characteristics of such RF signal may vary as a function of the orientation (e.g., pitch, yaw, roll, attitude, etc.) of sense head 300 relative to port 42. Display device 350 may receive indications of such RF signals from each vertical coil 306, and may process these signals through a logic operable to compare the signal picked up at each vertical coil 306. When sense head 300 is oriented parallel with port 42, the three received signals may have an approximately equal amplitude, and a phase shift of approximately zero. As will be described in greater detail below, display device 350 may further comprise a logic operable to provide a visual representation to the user indicating the relative orientation of sense head 300 and port 42, and further indicate when sense head 300 is oriented substantially parallel with port 42.

In another embodiment, sense head 300 and port 42 are configured such that orientation characteristics may detected based on the phase relationship between signals emitted by coil 114 and signals from within sense head 300 (e.g., a launch/drive signal from a TET coil in sense head 300). For instance, if the signals are in phase, such a relationship may indicate that port 42 is oriented parallel with sense head 300, and that septum 76 is facing sense head 300; whereas the signals being 90° out of phase may indicate that port 42 is at approximately a 45° to 90° angle with respect to sense head 300; while the signals being 180° out of phase may indicate that port 42 is approximately flipped over relative to sense head 300 (e.g., septum 76 is facing inward within patient 34). When port 42 is oriented at an angle of about 90° relative to sense head 300, the phase difference may abruptly flip between the signals being substantially in phase to the signals being substantially out of phase. Other orientations may be detected based on other corresponding phase relationships. The phase relationship of signals may be compared using any suitable logic (e.g., microprocessor, etc.) in any suitable location (e.g., within sense head 300, within display device 350, etc.).

In some embodiments, it may be desirable to position sense head 300 directly over port 42, if possible, to determine the orientation of port 42. In particular, in some embodiments, if sense head 300 is too far from being over the center of port 42, it may not be possible to obtain signals emitted by port 42, or the results may otherwise be unsatisfactory or untrustworthy. Accordingly, there may be a target boundary around a location that is approximately over the center of port 42, within which it may be desirable to position sense head 300 to determine port orientation 42 in some embodiments. By way of example only, a position that is approximately over the center of port 42 may be located using sense head 300 in a manner as described herein. Alternatively, the center of port 42 may be approximately located simply by palpation or using some other device or technique. Such alternatives may be desirable where sense head 300 has only a single coil, or where sense head is not able to detect the location of port 42. Other ways in which the center of port 42 may be located will be apparent to those of ordinary skill in the art. In other embodiments, the center of port 42 need not be approximately determined in order for port orientation 42 to be determined.

It will be appreciated that port 42 orientation information may be obtained by moving sense head 300 within a boundary over the approximate center of port 42. For instance, in some embodiments, where coil 114 in port 42 is at some angle other than approximately 0° or approximately 180° relative to a coil in sense head 300, the phase of the signals may change significantly as sense head 300 is moved away from a position that is over the approximate center of port 42. By contrast, where coil 114 in port 42 is at approximately 0° or approximately 180° relative to a coil in sense head 300, the change in the phase of the signals may be minimal as sense head 300 is moved away from a position that is over the approximate center of port 42. Furthermore, if coil 114 in port 42 is between approximately 0° and approximately 45° relative to a coil in sense head 300, then the signals may remain substantially in phase as sense head 300 is moved away from a position that is over the approximate center of port 42; whereas the signals may be either out of phase or switch between being in phase and out of phase as sense head 300 is moved away from a position that is over the approximate center of port 42 when coil 114 in port 42 is at an angle that is greater than approximately 45° relative to a coil in sense head 300.

In some embodiments, it may be desirable to compare the phase of the signals when the sensed amplitude of the signals is at a maximum. Furthermore, where coil 114 in port 42 is at some angle other than approximately 0° or approximately 180° relative to a coil in sense head 300, the sensed amplitude of the signal from coil 114 may be at its highest when sense head 300 is positioned on the side or region that port 42 is facing. Accordingly, where a non-zero angle of port 42 tilt is determined using any technique, the angle at which port 42 is facing may be determined by moving sense head 300 within a region around a position that is approximately over the center of port 42 until the maximum signal amplitude is measured.

Accordingly, it will be appreciated that orientation of port 42 may be determined based upon changes in phase relationships and/or amplitude as sense head 300 is moved within a boundary over the approximate center of port 42, in addition to or as an alternative to determining orientation simply by comparing a phase relationship when sense head 300 is located approximately over the center of port 42. It will also be appreciated that a ratio may be used to determine port 42 orientation. By way of example only, a suitable ratio may be the percentage of maximum signal amplitude when the signals are in phase to the maximum signal amplitude when the signals are out of phase. Little or no phase change may be interpreted to indicate that the coil 114 in port 42 is substantially parallel to a coil in sense head 300 (e.g., which may indicate that port 42 is "flat" and properly oriented); while a significant phase change may be interpreted to indicate that coil 114 in port 42 is not "flat" or is "tilted," or that coil 114 in port 42 is "flipped."

In some situations, a comparison of signals may reveal that port 42 is tilted relative to sense head 300, and that septum 76 may not be reached by a needle inserted directly through needle window 302 of sense head 300 when sense head 300 is placed flat against patient 34. In some such situations, sense head 300 may be tilted relative to patient 34 until the signals are in phase, such that the tilt of sense head 300 relative to the adjacent surface of patient 34 may mimic the tilt of port 42. In other words, tilting of sense head 300 may cause the signals to be in phase when sense head 300 is tilted to an orientation making sense head 300 substantially parallel with port 42. In some such situations, where sense head 300 is tilted in a manner to orient sense head 300 substantially parallel with port 42, a needle may then be inserted through needle window 32 of sense head 300 to reach septum 76 of port 42. Accordingly, sense head 300 may be used to not only determine a proper insertion point for a needle, but also to determine a proper insertion angle for a needle in certain situations.

Figure 14:
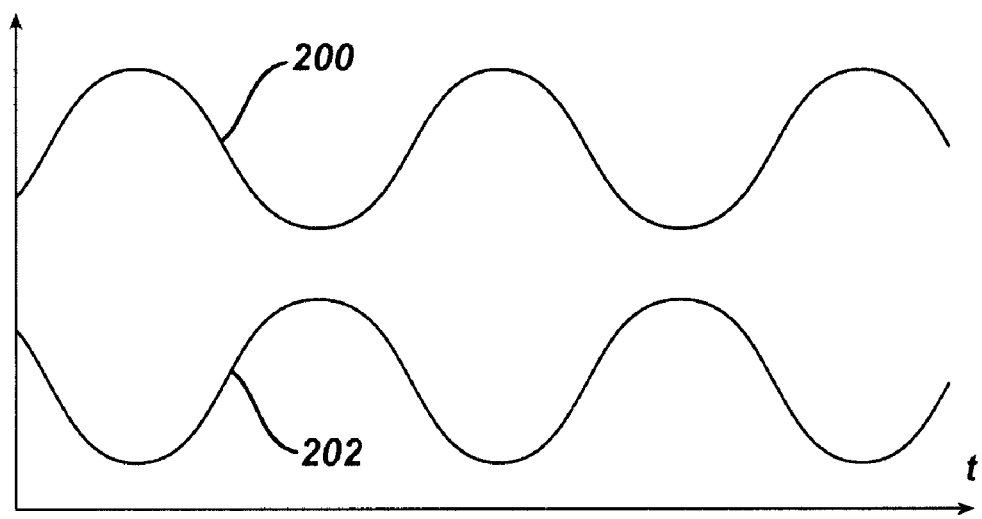
FIG. 14 is a graph showing a pair of curves representing signals that are out of phase.
Figure 15:
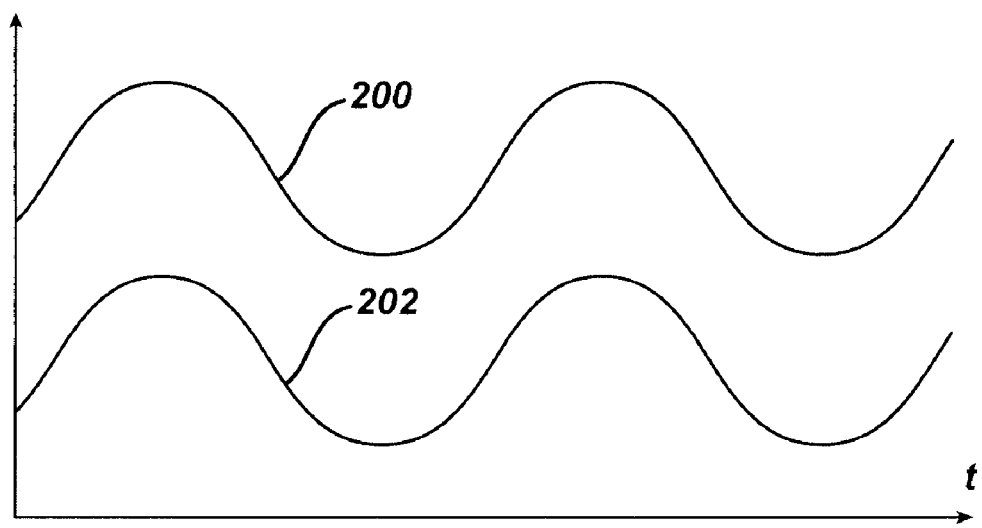
FIG. 15 is a graph showing a pair of curves representing signals that are in phase.

By way of example only, a drive frequency of approximately 50 kHz may be used when determining phase relationships to determine orientation of port 42. Of course, any other suitable frequency or frequencies may be used. By way of illustration, FIG. 14 shows a curve 200 representing an RF signal in a coil in sense head 300, and a curve 202 representing an RF signal emitted by coil 113 in port 42. As shown in FIG. 14, the signals are approximately 180° out of phase, which may indicate that port 42 is flipped over relative to sense head 300 (e.g., septum 76 is facing inward within patient 34). By contrast, FIG. 15 shows curve 200 representing an RF signal in a coil in sense head 300, and curve 202 representing an RF signal emitted by coil 114 in port 42, representing with the signals being in phase. This may indicate that port 42 is oriented parallel with sense head 300, and that septum 76 is facing sense head 300. In other embodiments, a different phase relationship may indicate a flipped port 42 or parallel port 42. For instance, sense head 300 or port 42 may be configured such that a flipped port 42 will provide a signal that is in phase with signal in sense head 300; and such that the signals are approximately 180° out of phase when septum 76 is facing sense head 300. Interpretation of phase relationships may therefore be dependent upon the orientation of coil 114 within port 42 or the orientation of a relevant coil within sense head 300.

It will be appreciated that any suitable number of coils within sense head 300 may be used to compare the "external phase" of sense head 300 with the "internal phase" of coil 114 in port 42. For instance, the phase of a single coil within sense head 300 may be compared with the phase of coil 114 in port 42. Alternatively, the phase of a plurality of coils (e.g., three sets of coils 304) within sense head 300 may be compared with the phase of coil 114 in port 42.

Figure 16:
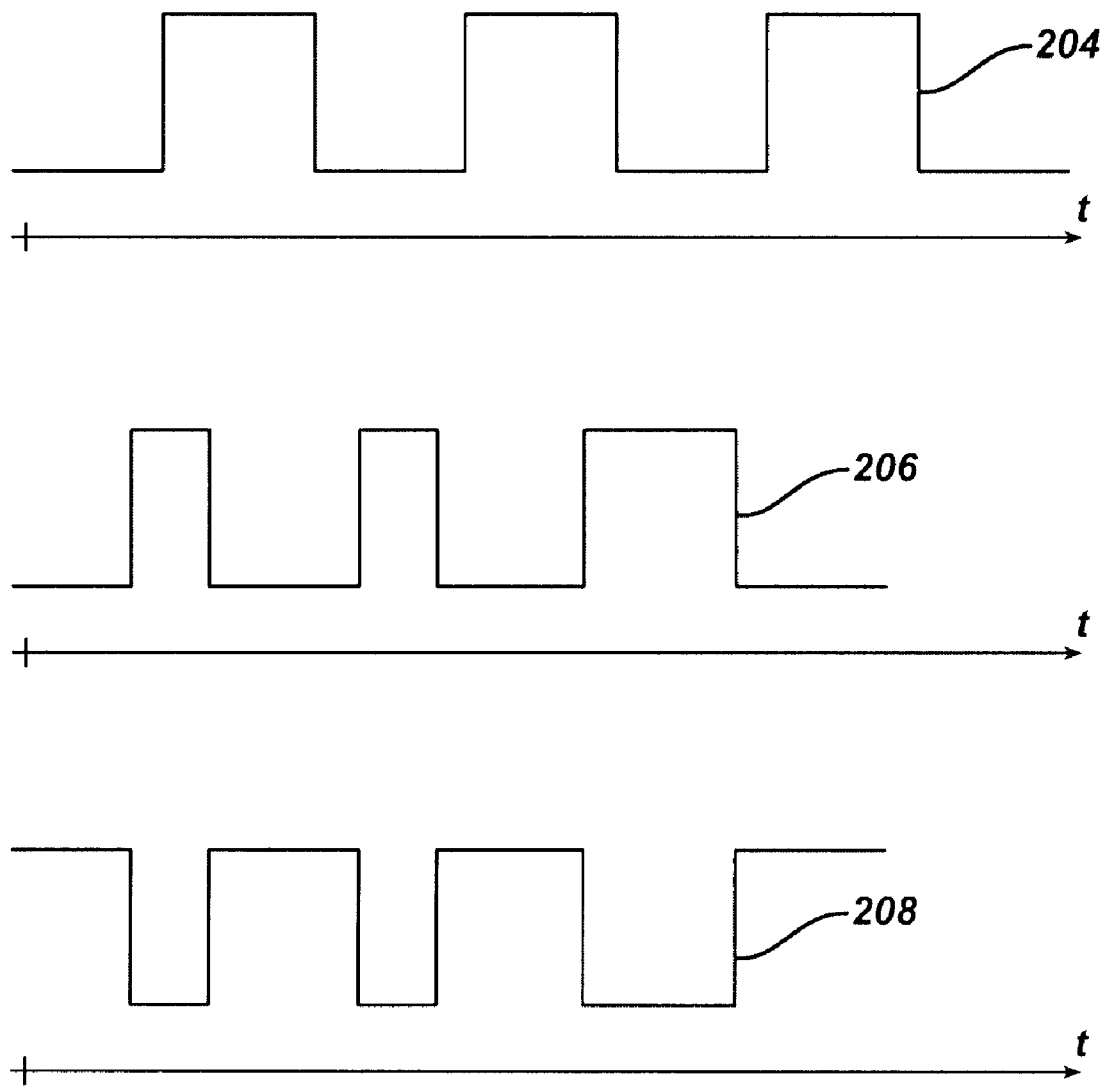
FIG. 16 illustrates two patterned pulsed signals compared to a reference pulsed signal.

In another embodiment, coil 114 in port 42 emits a pattern of pulses when sense head 300 is passed over port 42, such as two short pulses followed by a longer pulse (e.g., about 3-4% longer than the short pulses) when port 42 is right side up. When port 42 is flipped 180°, the pattern may be reversed. By way of illustration, FIG. 16 illustrates curve 204 representing a pulsed reference signal, a curve 206 representing a signal emitted by a port 42 that is right side up, and a curve 208 representing a signal emitted by a port that is flipped 180°. Sense head 300 may receive these signals, and sense head 300 or any other device (e.g., display device 350, etc.) may process such signals, such that the user may be provided with an audio or visual indication relating to the orientation of port 42 as described in greater detail below. Accordingly, it will be appreciated that vertical coils 306 are not necessarily needed to obtain orientation information, and that the phase of signals need not necessarily be compared in order to obtain orientation information. It will also be appreciated that, where a signal patterns are used to provide orientation information, such patterns may come in any of a variety of forms and may have any suitable durations.

Figure 17:
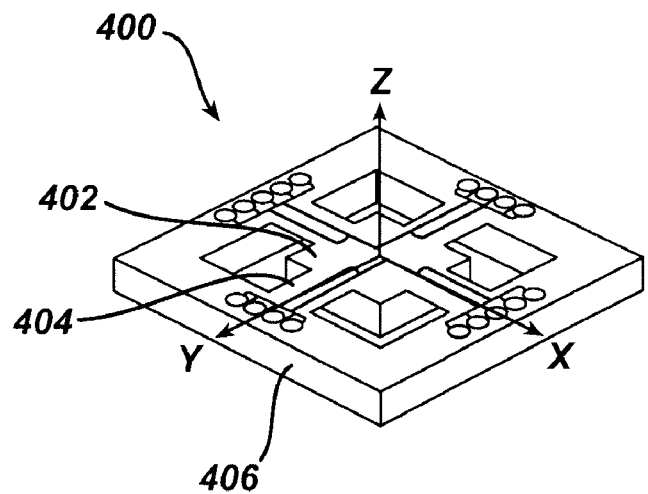
FIG. 17 is a perspective view of an exemplary accelerometer.
Figure 18:
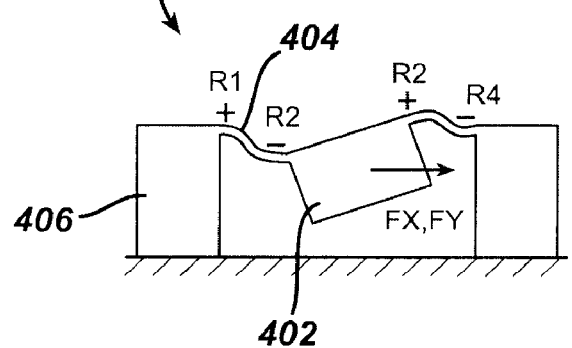
FIG. 18 is a side, cross-sectional view of the accelerometer of FIG. 17, under an acceleration in at least one lateral direction.
Figure 19:
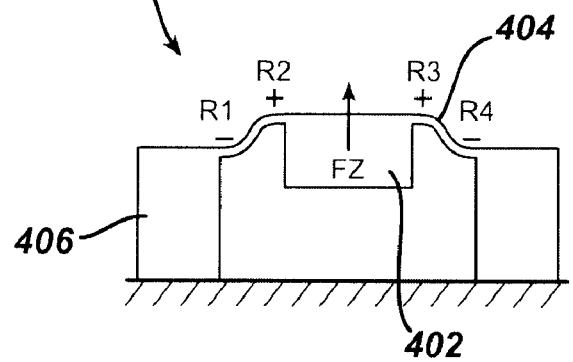
FIG. 19 is a side, cross-sectional view of the accelerometer of FIG. 17, under an acceleration in a vertical direction.

In yet another embodiment, port orientation information is obtained using an accelerometer, such as a tri-axis accelerometer 400 as illustrated in FIGS. 17-19. In this example, accelerometer 400 comprises a mass 402 suspended by piezo-resistive doped silicone beams 404 within a ring 406. Accelerometer 400 is positioned within port 42, and is in communication with coil 114. Accelerometer 400 is therefore operable to communicate port orientation information to sense head 300 via telemetry. In other embodiments, accelerometer 400 may be located on port 42, elsewhere within patient 34, and/or may be configured to communicate with sense head 300 or any other device using any other suitable telemetry structures or techniques.

It will also be appreciated that, when piezo-resistive doped silicon beams 404 are interfaced with appropriate signal conditioning circuitry (not shown), an analog output voltage may be provided that is proportional to the acceleration imparted on accelerometer 400. For instance, in a stationary context, the earth's gravity may be realized and reported as 1 g. The orientation of accelerometer 400 may be determined by comparing a gravitational signal obtained through accelerometer 400 to 1 g. The gravitational signal obtained through accelerometer 400 may be a function of the electro-resistive properties of silicon beams 404, or of a change in the electro-resistive properties of silicon beams. By way of example only, FIG. 18 depicts mass 402 of accelerometer 400 undergoing an acceleration in a lateral direction, which is sensed by a change in electro-resistive properties in silicon beams 404 that is caused by deformation of the silicon beams 404. Such acceleration may be realized when port 42 is tilted within patient 34. As another example, FIG. 19 depicts mass 402 of accelerometer 400 undergoing an acceleration in a vertical direction, which is sensed by another change in electro-resistive properties in silicon beams 404 that is caused by deformation of the silicon beams 404. Such acceleration may be realized when port 42 is flipped within patient 34.

Suitable configurations for signal conditioning circuitry that may be used with accelerometer 400 will be apparent to those of ordinary skill in the art, as will other ways in which accelerometer 400 may be used to obtain port 42 orientation information.

Figure 20:
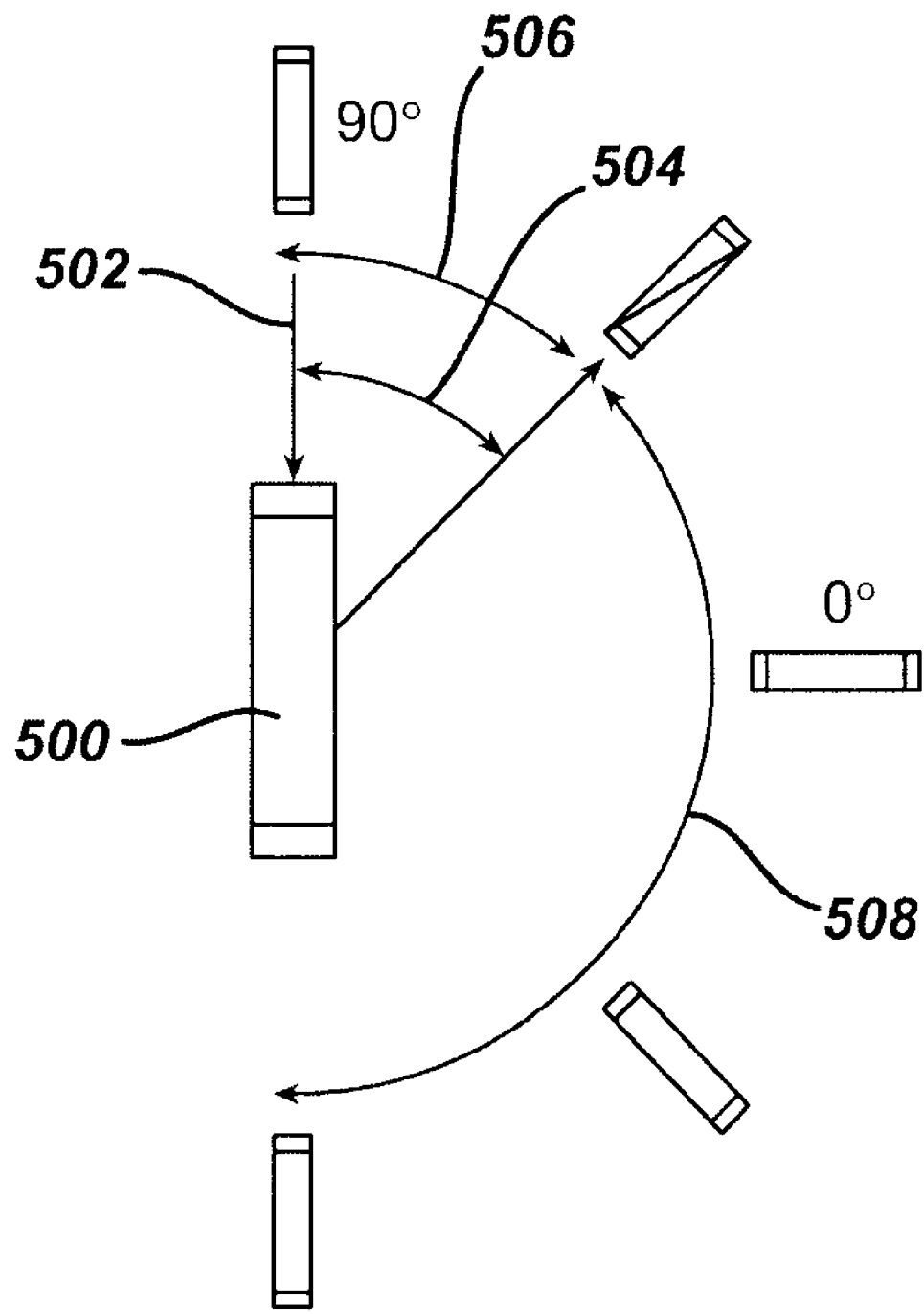
FIG. 20 is a plan view of an exemplary tilt sensor.

In another embodiment, a tilt sensor 500 is used. An exemplary tilt sensor 500 is illustrated in FIG. 20, in which arrow 502 represents the direction of gravity. In this example, tilt sensor comprises a switch (not shown) that is normally open when tilt sensor 500 is vertical. As tilt sensor 500 is tilted (e.g., rotated relative to arrow 502), the switch remains open until the degree of tilt passes a predefined switch angle 504. After tilt sensor 500 has been tilted past switch angle 504, the switch in tilt sensor 500 closes, and remains closed as tilt sensor 500 continues to be tilted past switch angle 504.

Accordingly, the switch in tilt sensor 500 remains open while tilt sensor 500 is oriented within a first angular range 506; and the switch in tilt sensor 500 is closed while tilt sensor 500 is oriented within a second angular range 508. In one embodiment, tilt sensor 500 comprises a SQ-SEN6XX by SignalQuest, Inc. of Lebanon, N.H. Of course, any other suitable type of tilt sensor 500 may be used. It will also be apparent to those of ordinary skill in the art that the normally open and normally closed conditions may be reversed, and that the switch may be designed to change from a closed or open state at any desired switch angle 504 or angles. For example the switch may be normally closed at tilt angles between approximately 0° and approximately +/−30°, and normally open at tilt angles between approximately 180° and +/−150°. Other suitable angular ranges 506, 508 and switch conditions for such angular ranges 506, 508 will be apparent to those of ordinary skill in the art.

Furthermore, a tilt sensor 500 may be incorporated directly into or onto port 42, and may be in communication with coil 114 (e.g., directly, via some other component, or otherwise in communication with coil 114). Tilt sensor 500 of the present example is therefore operable to communicate port orientation information to sense head 300 via telemetry. In other embodiments, tilt sensor 500 may be located elsewhere within patient 34, and/or may be configured to communicate with sense head 300 or any other device using any other suitable telemetry structures or techniques. Alternatively, tilt sensor 500 may be used to obtain port 42 orientation information in any other suitable fashion using any other suitable structures, circuits, or techniques.

In yet another embodiment, an inclinometer (not shown), such as a MEMS inclinometer by way of example only, is incorporated into port 42 for obtaining orientation information. Still other suitable structures and techniques for determining port orientation information (e.g., other than phase comparisons and/or an accelerometer, inclinometer, tilt sensor, position sensitive switch, etc.) will be apparent to those of ordinary skill in the art.

While port orientation detection is discussed herein in the context of a system that is operable to obtain pressure data, it will be appreciated that the structures and techniques described herein for determining port orientation need not necessarily be incorporated into a system that is also operable to obtain pressure data. For instance, pressure data may be essentially irrelevant in some systems (e.g., drug infusion systems, etc.), while orientation of an injection port (or the orientation of some other system component) may be relevant. Accordingly, it is contemplated that the structures and techniques described herein for determining port orientation may also be used in systems where there is no sensing of any type of pressure whatsoever. It is also contemplated that the structures and techniques described herein for determining port orientation may be incorporated into components other than injection ports, and may be used to determine the orientation of such non-port components. For instance, the phase of a signal emitted by a coil about an implanted pressure sensor or other implanted device may be compared with the phase of an external coil to determine the orientation of the implanted pressure sensor or other implanted device for any suitable purpose(s). Other ways in which the orientation detection structures and techniques described herein may be used in various structural contexts will be apparent to those of ordinary skill in the art.

Figure 21:
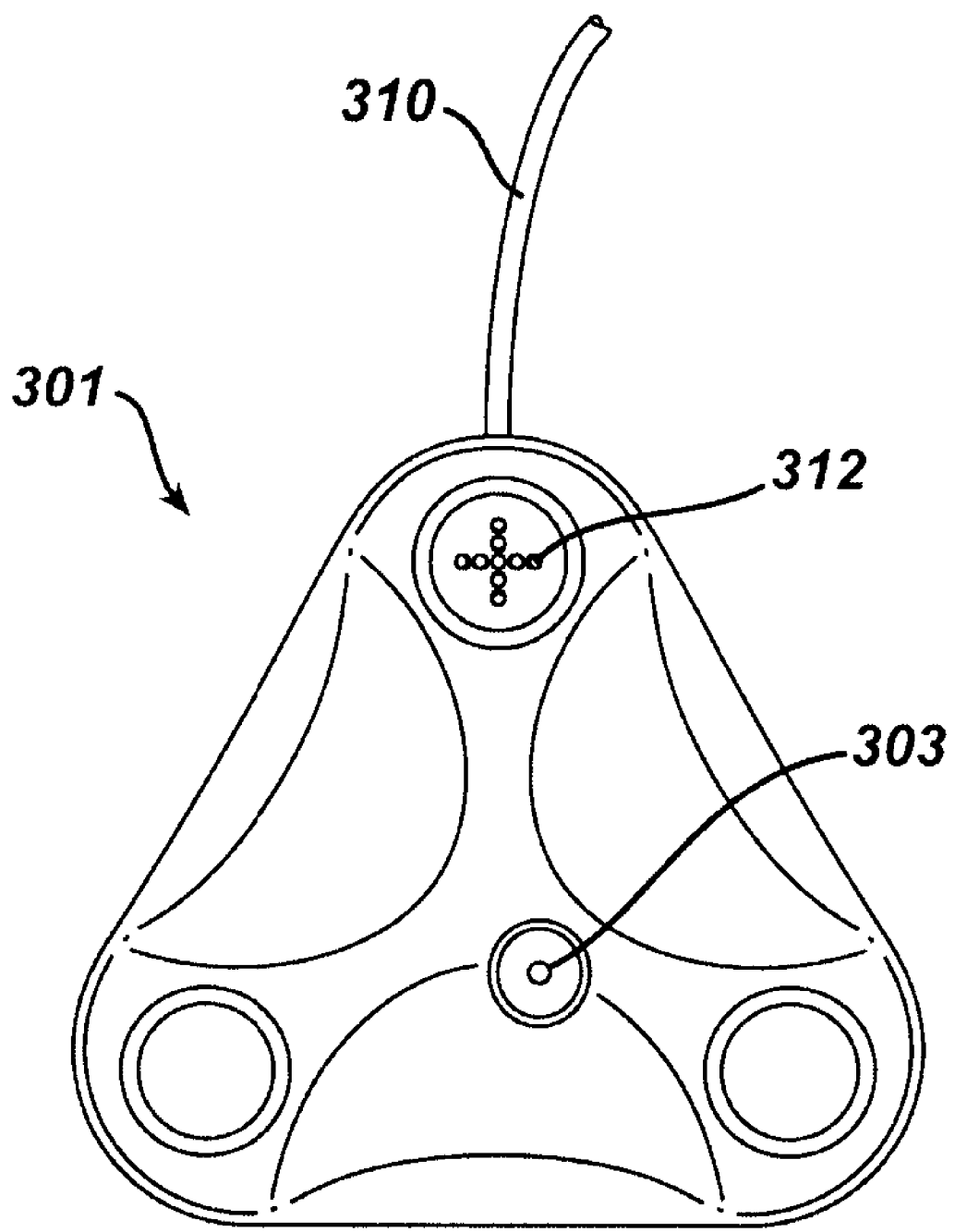
FIG. 21 is a plan view of an alternative exemplary sense head.

An alternative sense head 301 is shown in FIG. 21. In this variation, needle window 303 is offset from the center of sense head 301, but is otherwise configured similar to sense head 300. Such an offset of needle window 303 may reduce the likelihood that the housing of sense head 301 will physically interfere with external anatomical structures of patient 34 where such interference would otherwise create difficulties in positioning the centered needle window 302 of sense head 300 over port 42. The offset of needle window 303 as shown in FIG. 21 is merely exemplary, and it will be appreciated that needle window 303 may be located elsewhere (e.g., proximate to an edge or corner of the housing of sense head 301, etc.). It will also be appreciated that, with needle window 303 not being positioned at the center of sense head 301, needle window 303 will not be positioned at the collective center of the arrangement of horizontal coils 304 and vertical coils 306. Nevertheless, coils 304, 306 may still be used to determine the relative positioning of needle window 303 and port 42 using techniques similar to those employed with sense head 300. For instance, a corrective constant (e.g., a vector) may be factored into an algorithm used to process RF signals sensed by coils 304, 306. Such a corrective constant may represent the displacement (e.g., in terms of distance and direction) of needle window 303 relative to the center of sense head 301 (or relative to the center of the arrangement of coils 304, 306). Various ways in which such a corrective constant may be factored into the algorithm will be apparent to those of ordinary skill in the art.

By way of example only, the position of the center of sense head 301 relative to port 42 may first be found by comparing RF signals (e.g., in terms of phase and amplitude) received by horizontal coils 304 (thereby obtaining a "determined position"). The corrective constant may then be added to that determined position to further determine the position of needle window 303 relative to port 42. Alternatively, the properties of RF signals received by coils 304 may have one or more characteristic disparities (or one or more characteristic disparity ranges) when needle window 303 is positioned directly over port 42, such that the algorithm may treat that disparity in a manner similar to the minimized phase and amplitude differences of RF signals received by coils 304 in sense head 300. In other words, the algorithm may treat such disparity as a target to be reached. The characteristic disparities in the properties of RF signals sensed by horizontal coils 304 when needle window 303 is positioned directly over port 42 may be a function of the displacement of the needle window 303 relative to sense head 301, such that the characteristic disparities may be predetermined. Of course, any other techniques or structures suitable for determining the position of needle window 303 relative to port 42 may be used.

Figure 22:
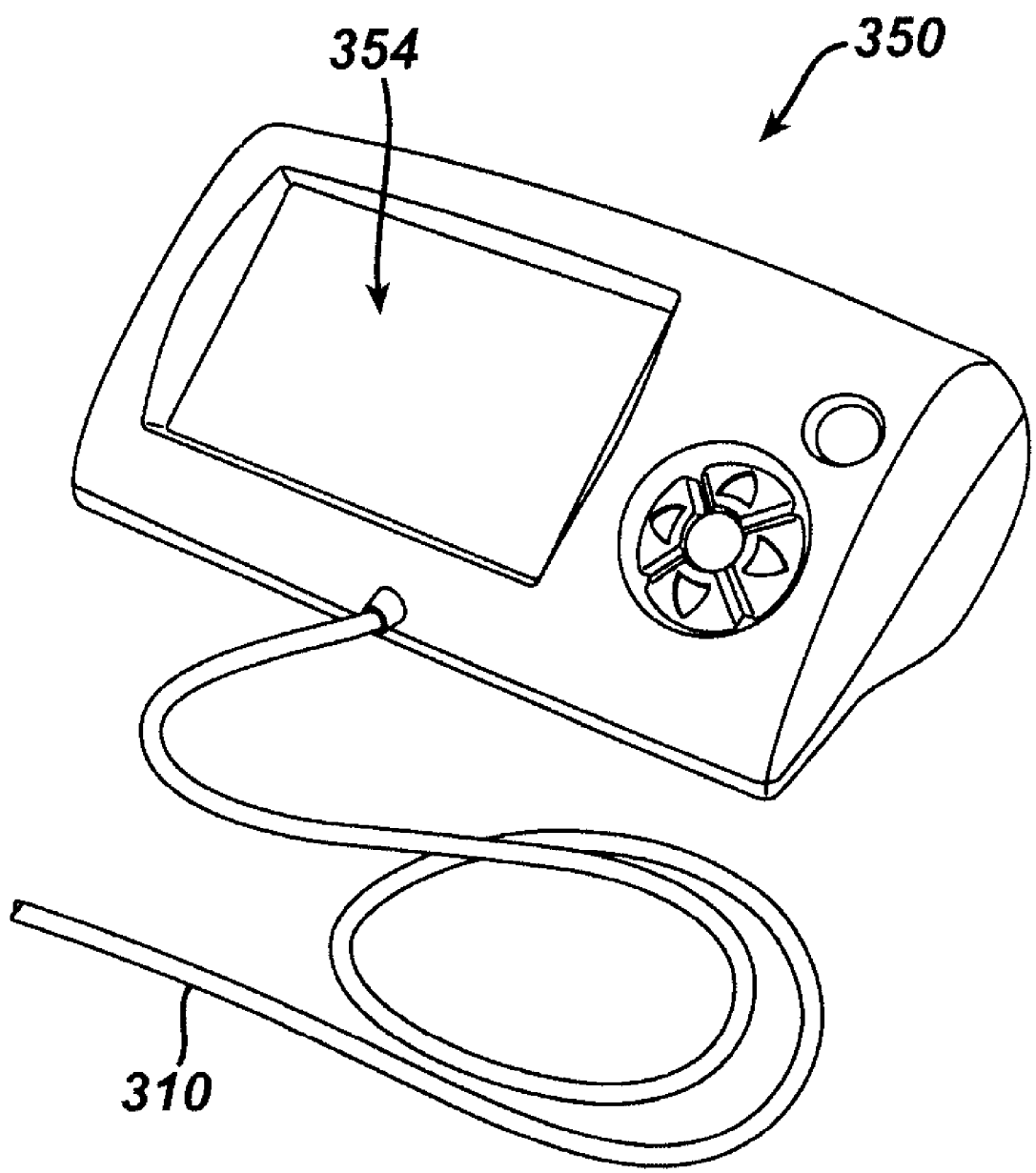
FIG. 22 is a perspective view of an exemplary display device suitable for coupling with the sense head of FIG. 10.
Figure 23:
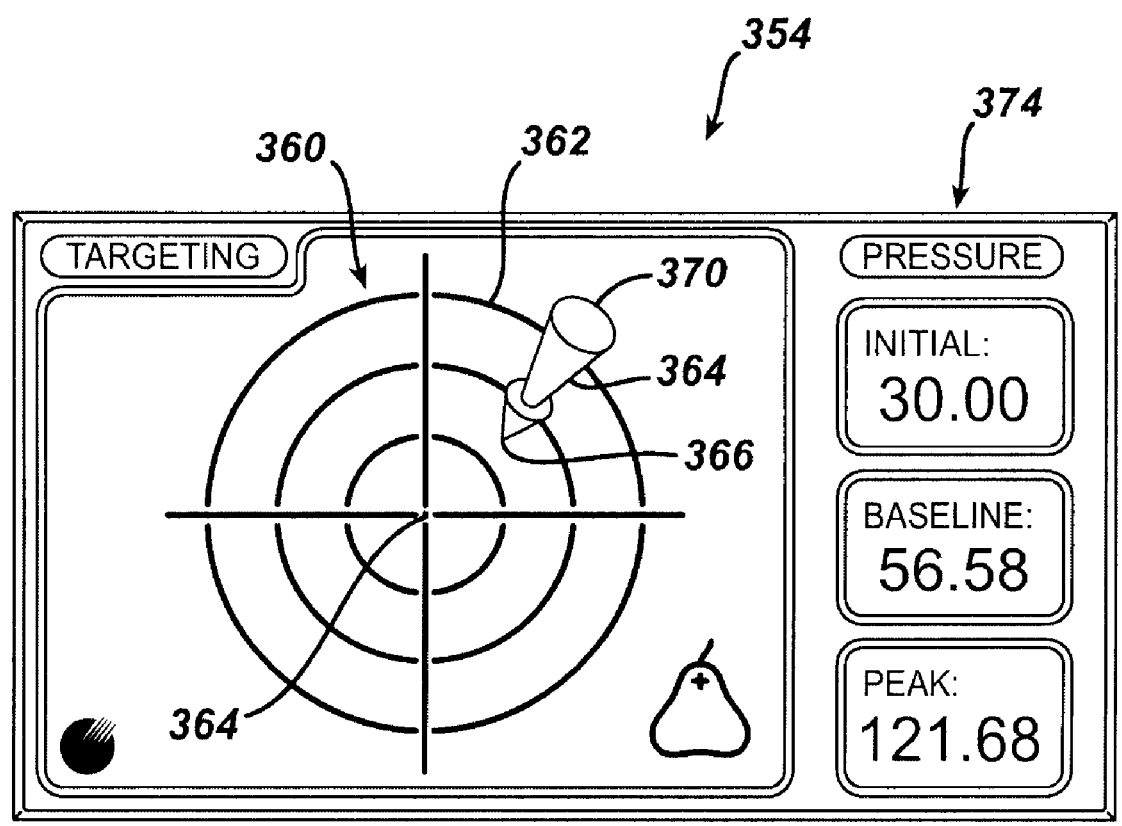
FIG. 23 is an exemplary graphical display suitable for the display device of FIG. 22.
Figure 24:
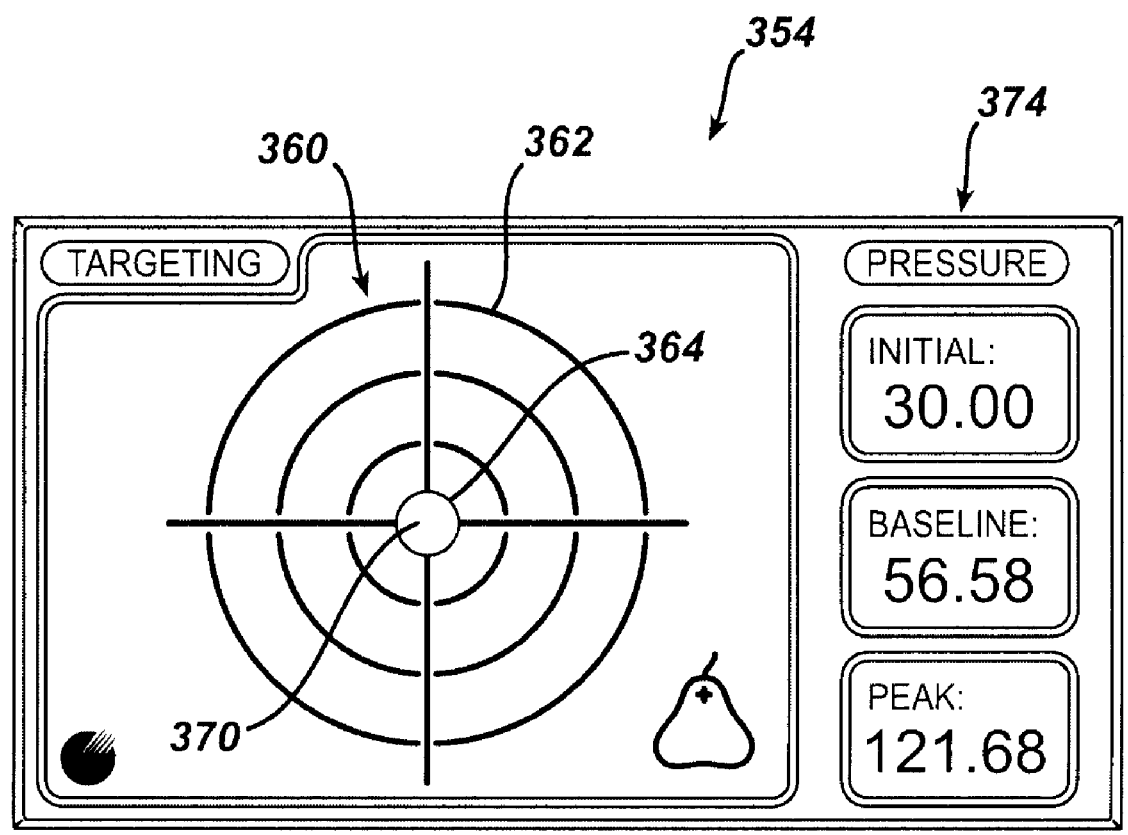
FIG. 24 is the graphical display of FIG. 23 indicating suitable positioning of the sense head of FIG. 10.

FIG. 22 shows an exemplary display device 350 that is configured to translate information communicated from the sense head 300 into visual representations readable by a user. In the present example, display device 350 is in communication with sense head 300 via cable 310, but again, any alternative to cable 310 may be used. Display device 350 further comprises a graphical display 354, which includes a target display 360, and is illustrated in FIGS. 23-24. The target display 360 of the present example includes a crosshairs 362 and an arrow indicator 364. The target display 360 of this example is operable to render location and orientation information relating to the location and orientation of sense head 300 relative to port 42. In particular, the position of the tip 366 of arrow indicator 366 relative to the center 364 of crosshairs 362 may serve to indicate the position of needle window 302 relative to the center of port 42 (e.g., septum 76). In other words, the center 364 of crosshairs 360 may represent the center of septum 76; with the tip 366 of arrow indicator 366 representing needle window 302. The positioning data may be refreshed at any suitable rate, such as in approximate real-time, to provide the user location feedback via targeting display 360. The user may thus move sense head 300 until targeting display 360 indicates that the needle window 302 is located directly over port 42.

Orientation data may be rendered via targeting display 360 in terms of the tilt of arrow indicator 366. In other words, the direction and amount of tilt of arrow indicator 366 may represent the orientation of sense head 300 relative to port 42, such that arrow indicator 366 pivots about its tip 366 to indicate such orientation. As with positioning/location data, the orientation data may be refreshed at any suitable rate, such as in approximate real-time, to provide the user orientation feedback via targeting display 360. To the extent that sense head 300 cannot be satisfactorily oriented relative to port 42 (e.g., if port 42 has flipped upside-down or on its side relative to the fascial plane of patient), surgery may be required to re-orient port 42. Furthermore, to the extent that indicating the orientation of port 42 with arrow indicator 366 is not feasible, any other suitable type of indication may be used. For instance, a textual indication may be provided (e.g., text indicating that that port is flipped over 180°), an indication may be audible (e.g. number, frequency, or tone of beeps), or indication of port orientation may be provided in any other suitable way.

FIG. 24 shows a view of display device 350 with a target display 360 indicating that the sense head 300 is positioned substantially directly over port 42 and substantially parallel with port 42. Accordingly, arrow indicator 366 is positioned over center 364 of crosshairs 362, and pivoted upright (i.e., perpendicular to the screen), such that only the tail 370 of arrow indicator 366 can be seen. Such a display may indicate to the user that a needle 403 inserted straight into needle window 302 will successfully reach septum 76 of port.

It will also be appreciated that further visual indication may be given to a user to represent location and orientation information, such as with the use of colors. For instance, in the targeting display 360 shown in FIG. 23, the arrow indicator 366 may be shown in red to indicate that insertion of needle 403 through needle window 302 would not be appropriate (e.g., needle 403 would not reach septum 76). By contrast, in the targeting display 360 shown in FIG. 24, tail 370 of arrow indicator 366 may be shown in green to indicate that insertion of needle 403 through needle window 302 would be appropriate (e.g., the needle would reach septum 76).

It will also be appreciated that sense head 300 need not be perfectly parallel with port 42 in order to successfully pass needle 403 through needle window 302 into septum 76. Accordingly, display device 350 may provide an indication showing that needle 403 may successfully reach septum 76 through needle window 302, despite a non-parallel orientation of sense head 300 relative to port 42. For instance, such orientation may be indicated where tail 370 of arrow indicator 366 is within a particular ring of crosshairs 362. Alternatively, such orientation may be indicated by coloring arrow indicator 366 yellow or some other color. Still other ways in which the sufficiency of a non-parallel orientation may be indicated in target display 360 will be apparent to those of ordinary skill in the art.

Similarly, there may be a situation in which sense head 300 cannot be located directly over port 42 without having unsatisfactory orientation of sense head 300 relative to port 42; while sense head 300 may be oriented generally parallel with port 42 when not positioned directly over port 42. In some such situations, the septum 76 may nevertheless be reached by needle 403 inserted through needle window 302 if needle 403 is oriented properly with respect to sense head 300 (e.g., at an angle of approximately 80° or a 10° deflection). Accordingly, display device 350 may provide an indication showing that needle 403 may successfully reach septum 76 through needle window 302, despite sense head 300 not being positioned directly over port 42. For instance, such orientation may be indicated where tail 370 of arrow indicator 366 is within a particular ring of crosshairs 362. Alternatively, such orientation may be indicated by coloring arrow indicator 366 yellow or some other color. Still other ways in which the sufficiency of an indirect sense head 300 location may be indicated in target display 360 will be apparent to those of ordinary skill in the art.

It will also be appreciated that sense head 300 may be configured to obtain depth data indicating the distance from needle window 302 to port 42 (and, hence, depth to septum 76). Such depth data may be represented on display device 350 in a variety of ways. For instance, the depth may be indicated as a numerical value and/or in any other suitable way. In addition to location, orientation, and depth-related information, other geometric information that may be obtained by sense head 300 and communicated to display device 350 will be apparent to those of ordinary skill in the art.

In addition to displaying information relating to the location and orientation of sense head 300 relative to port 42, display device 350 may also display pressure data communicated from port 42 to sense head 300. Accordingly, display device 350 of the present example comprises a pressure display portion 374. As shown, pressure display portion 374 provides an initial pressure reading, a baseline pressure, and a peak pressure. The initial pressure reading represents the pressure within implanted portion 32 before fluid is added or withdrawn. The baseline pressure reading represents the current pressure within implanted portion 32 (e.g., as fluid is being added or withdrawn or after fluid has been added or withdrawn). The peak pressure reading represents the peak pressure sensed during peristaltic motion of the stomach. Of course, any other pressure parameters may be displayed, as may other data such as temperature, etc. It will therefore be appreciated that, in one embodiment, display device 350 provides the similar functionalities and serves similar purposes as display 66 described above.

As noted above, sense head 300 may be configured to receive pressure data from port 42 in a manner similar to pressure-reading device 60. It will therefore be appreciated that the TET coil of sense head 300 may also serve as a telemetry coil to receive telemetry signals from coil 114 in port 42 indicating pressure or other data. Alternatively an additional coil dedicated to such telemetry may be provided in sense head 300. As yet another variation any of vertical coils 306 and/or horizontal coils 304 may be used for such telemetry. Still other suitable configurations will be apparent to those of ordinary skill in the art.

In view of the foregoing, it will be appreciated that sense head 300 and display device 350 may be used to provide approximately real-time pressure measurements to a user before, during, and after the addition or withdrawal of fluid to or from implanted portion 32. For instance, a surgeon may adjust the saline content of implanted portion 32 while patient 34 swallows a fixed amount of water, and may monitor the pressure level in implanted portion via sense head 300 and display device 350 during such activities. It will be appreciated that an optimal pressure adjustment may be determined based on a variety of factors related to pressure data, including but not limited to any of the following: the original baseline pressure; the new baseline pressure; the maximum peristaltic pressure; the minimum peristaltic pressure; the length of a peristaltic contraction; the Fourier transform of a peristaltic contraction data spike; the pressure decay time constant during persistaltic contractions; the total averaged pressure decay time constant during a water swallowing period; the number of peristaltic contractions to swallow a fixed amount of water; one or more forces exerted by an implanted device and/or an anatomical structure; energy of an implanted device or of fluid therein; the fill rate of fluid into an implanted device; the volume of fluid in an implanted device; the capacity of an implanted device; the flow rate of fluid into or within an implanted device; the pressure pulse rate of fluid within an implanted device; a counted number of pressure pulses of fluid within an implanted device; one or more electrical signals communicated from tissue prior to and/or in response to adjustment of an implanted device; chemical(s) output from tissue prior to and/or in response to adjustment of an implanted device; other tissue feedback responsive to adjustment of an implanted device; or any other factors.

In one embodiment, display device 350 is operable to receive data indicative of the above-noted factors in any suitable fashion (e.g., from sensors, etc.), and is further operable to automatically process such factors and present the result of such processing to the user. For instance, display device 350 may be configured to determine an ideal amount of fluid to be added or withdrawn based on such processing of factors, and may simply display a message to the user such as "Add 4 cc's of fluid," "Withdraw 0.5 cc's of fluid," or the like. Such messages may be displayed in addition to or in lieu of displaying pressure measurements, changes in pressure, or other data. Other suitable processes of any of the above-noted factors or other factors, as well as ways in which results of such processes may be presented to the user, will be apparent to those of ordinary skill in the art.

In the present example, pressure sensor 84 provides pressure data at an update rate of approximately 20 Hz. Such a rate may provide a telemetry/TET mode cycle completion at approximately every 50 ms. For instance, coil 114 may provide TET for port 42 for approximately 45 ms to power port 42, then provide telemetry of pressure data for approximately 5 ms. Of course, any other switching topology may be used. It will also be appreciated that switching between TET and telemetry may be unnecessary. For instance, port 42 may be active, such that TET is not required. As another example, a second coil (not shown) may be added to port 42, with one of the coils in port 42 being dedicated to TET and the other to telemetry. Still other alternatives and variations will be apparent to those of ordinary skill in the art.

While display device 350 of the present example shows pressure data being represented numerically, it will be appreciated that pressure data may be represented in a variety of other ways. For instance, a graph may show pressure as a function of time, which may be useful for monitoring pressure during peristaltic activity or for other purposes.

Figure 25:
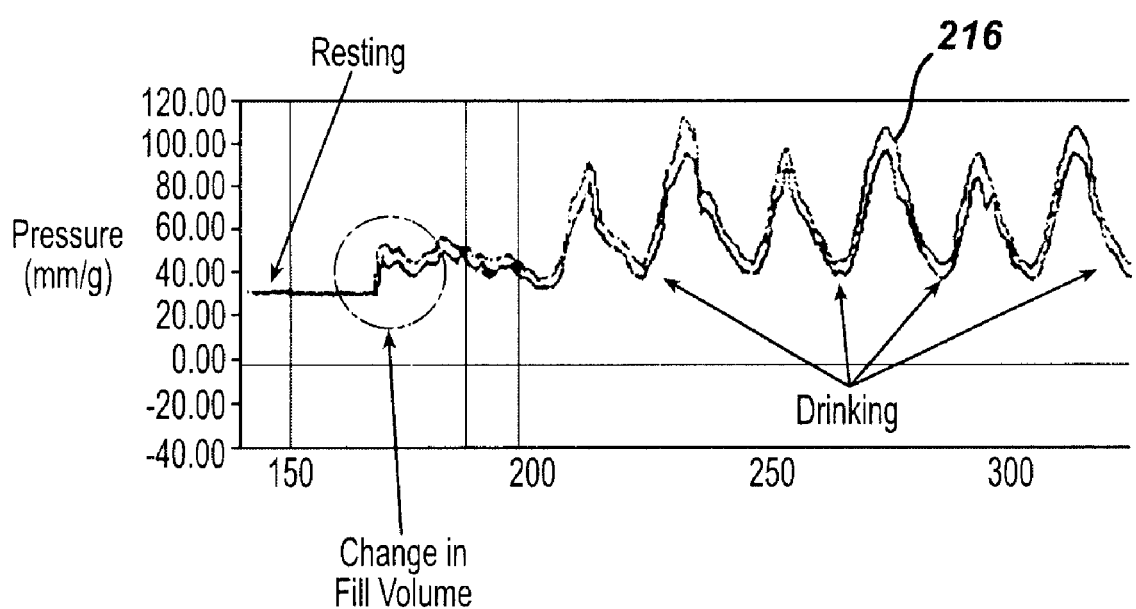
FIG. 25 is a graph indicating a pressure signal from a pressure sensing system, such as may appear on an external monitor display during interrogation by a user.

By way of example only, FIG. 25 is a graphical representation of a pressure signal 216 from the pressure sensing system of the invention, such as may appear on display device 350 or some other display 66 during interrogation by a user. In the example shown in FIG. 25, the fluid pressure is initially obtained by pressure sensor 1120 in communication with sense head 300 via coil 114 while the patient is stable, resulting in a steady pressure reading as shown. Next, an adjustment is applied to band 38 to decrease the stoma size. During the band adjustment, the pressure sensing system 1088 continues to measure the fluid pressure and transmit the pressure readings through the patient's skin to sense head 300. As seen in the graph of FIG. 25, the pressure reading rises slightly following the band adjustment. In the example shown, the patient is then asked to drink a liquid to check the accuracy of the adjustment. As the patient drinks, the pressure sensing system continues to measure the pressure spikes due to the peristaltic pressure of swallowing the liquid, and transmit the pressure readings to display device 350 for display.

It will also be appreciated that absolute values of pressure at particular moments in time need not be displayed, and that display device 350 may instead display changes in pressure value. Other ways in which pressure data or other data may be displayed will be apparent to those of ordinary skill in the art.

As discussed above, it may be desirable to account for temperature, atmospheric pressure, and other factors when considering measurements of pressure within implanted portion 32. Accordingly, sense head 300 may receive additional data such as temperature measurements taken within implanted portion 32, and display device 350 may comprise logic configured to adjust pressure readings in accordance with a variety of such factors.

By measuring and visually depicting the loading of the restriction device against the peristaltic motion of the stomach both during and after an adjustment, a physician may be provided with an accurate, real-time visualization of the patient's response to the adjustment. This instantaneous, active display of recorded pressure data may enable the physician to perform more accurate band adjustments. The data may be displayed over time to provide a pressure verses time history.

In addition to use during adjustments, a pressure sensing system may also be used to measure pressure variations in a restriction device at various intervals during treatment. Periodic pressure readings may enable a pressure sensing system to function as a diagnostic tool, to ensure that the food intake restriction device is operating effectively. In particular, a pressure sensing system may be utilized to detect a no pressure condition within the band, indicating a fluid leakage. Alternatively, the system may be used to detect excessive pressure spikes within the band, indicating a kink in catheter 44 or a blockage within the stoma.

A pressure sensing system may also enable a patient to track their own treatment, utilizing an external monitor, such as external device 36, at home. Using the external device, the patient may routinely download pressure readings to their physician's office, thereby reducing the number of office visits required to monitor the patient's treatment. Additionally, the patient could perform pressure readings at home and notify their physician when the band pressure drops below a specified baseline or exceeds a threshold, indicating the need for an adjustment of the device. A pressure sensing system may thus have benefits as both a diagnostic and a monitoring tool during patient treatment with a bariatric device.

In one version, sense head 300 comprises a switch (not shown) which is operable to switch sense head 300 between a positioning mode and a pressure sensing mode. Thus, the user may switch sense head 300 to positioning mode to obtain location and orientation data to sufficiently position sense head 300 over port 42. The user may then switch sense head 300 to pressure sensing mode to obtain pressure measurements before, during, and after the addition or withdrawal of fluid to or from implanted portion 32. Alternatively, a similar switch may be provided on display device 350. In yet another version, no switch is used, such that sense head 300 is operable for use in a positioning mode and pressure sensing mode simultaneously. Still other possible modes and features for effecting switching between such modes will be apparent to those of ordinary skill in the art.

It will also be appreciated that sense head 300 may be used in conjunction with a port that has a coil but lacks a pressure sensor. In other words, sense head 300 may be used simply to determine the location and/or orientation of a port. Upon such a determination, pressure data may be obtained from a source other than the port (e.g., from a sensor elsewhere in implanted portion, from a sensor external to the patient, etc.) or not be obtained at all. Other suitable methods and devices for obtaining pressure data are disclosed in U.S. Non-Provisional application Ser. No. 11/668,122, entitled "External Mechanical Pressure Sensor for Gastric Band Pressure Measurements," filed Jan. 29, 2007, the disclosure of which is incorporated by reference herein; U.S. Non-Provisional application Ser. No. 11/673,642, entitled "Apparatus for Adjustment and Sensing of Gastric Band Pressure," filed Feb. 12, 2007, the disclosure of which is incorporated by reference herein; and U.S. Non-Provisional application Ser. No. 11/682,459, entitled "Pressure Sensors for Gastric Band and Adjacent Tissue," filed Mar. 6, 2007, the disclosure of which is incorporated by reference herein.

It will also be appreciated that a plurality of pressure sensors may be used, including but not limited to several pressure sensors within a port and/or located elsewhere. For instance, a gastric band system may comprise a pressure sensor within a gastric band 38 in addition to a pressure sensor within a catheter 44 that is in fluid communication with band. Such a plurality of pressure sensors may provide an indication of how well fluid pressure is distributed among components of a gastric band system. Such a plurality of pressure sensors may also provide greater accuracy in pressure readings, reduce the likelihood of catheter obstruction (e.g., pinching) affecting pressure reading, may reduce effects of hydrostatic pressure changes from patient movement, or may provide a variety of other results. It will also be appreciated that any system that includes a plurality of pressure sensors may include a pressure sensor in a port 42 and/or a pressure sensor external to patient 34 (e.g., a pressure sensor in a syringe and/or a pressure sensor portion coupled with a syringe), in addition to any of the internal pressure sensors described above. Still other structures and techniques suitable for sensing or measuring pressure, and locations for sensing or measuring pressure, will be apparent to those of ordinary skill in the art. The particular structures and techniques described herein for sensing or measuring pressure are not deemed critical, and the inventors contemplate that any suitable structures, techniques, and locations for measuring pressure may be used.

In addition to sensing pressure of fluid within implanted portion 32 as described in various embodiments above, it will be appreciated that pressure of fluid within esophagus 48, upper pouch 50, and/or stomach 40 may also be sensed using any suitable device, such as an endoscopic manometer. By way of example only, such fluid pressure measurements may be compared against measured pressure of fluid within implanted portion 32 before, during, and/or after adjustment of pressure within implanted portion 32. Other suitable uses for measured pressure within esophagus 48, upper pouch 50, and/or stomach 40 will be apparent to those of ordinary skill in the art.

Furthermore, a device such as an internal or external inclinometer (or a substitute therefor) may be used to determine the angle at which patient 34 and/or implanted portion 32 is oriented (e.g., standing, lying down, etc.), which may be factored into pressure data sensed by one or more sensors to account for hydrostatic pressure effects caused by a patient's 34 orientation. Such a factor (or any other factor) may be accounted for prior to or in conjunction with the rendering of a pressure reading.

It will become readily apparent to those skilled in the art that the above invention has equally applicability to other types of implantable bands. For example, bands may be used for the treatment of fecal incontinence. One such band is described in U.S. Pat. No. 6,461,292, which is hereby incorporated herein by reference. Bands may also be used to treat urinary incontinence. One such band is described in U.S. Pub. No. 2003/0105385, which is hereby incorporated herein by reference. Bands may also be used to treat heartburn and/or acid reflux. One such band is described in U.S. Pat. No. 6,470,892, which is hereby incorporated herein by reference. Bands may also be used to treat impotence. One such band is described in U.S. Pub. No. 2003/0114729, which is hereby incorporated herein by reference. Other suitable types of and uses for implantable bands will be apparent to those of ordinary skill in the art.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated in relation to providing a pressure sensor within the injection port. Alternatively, a sensor could be positioned within a fluid filled portion of the band in order to measure pressure changes within the band. Additionally, a pressure sensor could be associated with an elastomeric balloon implanted within the stomach cavity to measure fluid pressure within the balloon. A pressure sensor could also be associated with a device external to a patient (e.g., as part of a syringe assembly), or could be provided in any other suitable location. The structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

What is claimed is:

1. A system for detecting the orientation of an implant component, the system comprising:
  (a) an implantable component, wherein the implantable component comprises a first coil operable to transcutaneously transmit a first signal comprising a pattern of pulses, wherein either at least two adjacent pulses in the pattern have a different duration or pulses within the pattern are provided at a different frequency relative to the frequency of other pulses within the pattern, wherein the implantable component is configured to be implanted within a patient;
  (b) an external component, wherein the external component comprises a second coil operable to detect the pattern of pulses transcutaneously transmitted by the first coil; and
  (c) a logic component in communication with the second coil, wherein the logic component is configured to process the pattern of pulses emitted by the first coil as detected by the second coil and determine the orientation of the first coil relative to the second coil based on the pattern of pulses emitted by the first coil as detected by the second coil.

2. The system of claim 1, further comprising an implantable gastric band system, wherein the implantable component is part of the implantable gastric band system.

3. The system of claim 2, wherein the gastric band system comprises an injection port.

4. The system of claim 3, wherein the implantable component comprises the injection port.

5. The system of claim 4, wherein the first coil is located within the injection port.

6. The system of claim 2, further comprising a pressure sensor, wherein the pressure sensor is configured to sense fluid pressure within the gastric band system.

7. The system of claim 6, wherein the first coil is in communication with the pressure sensor, wherein the first coil is operable to transmit pressure information obtained by the pressure sensor.

8. The system of claim 6, wherein the gastric band system comprises an injection port, wherein the pressure sensor is located within the injection port.

9. The system of claim 1, wherein the external component comprises a sense head operable to detect the position of the implantable component when the implantable component is located within the patient.

10. The system of claim 9, wherein the sense head comprises a plurality of coils, wherein the plurality of coils are operable to detect the position of the implantable component when the implantable component is located within the patient.

11. The system of claim 1, wherein the first signal has a first amplitude, wherein the second coil is further operable to transmit a second signal having a second amplitude, wherein the logic component is further operable to detect the orientation of the first coil relative to the second coil by comparing the first amplitude with the second amplitude.

12. The system of claim 1, wherein the external component comprises a plurality of additional coils.

13. The system of claim 11, wherein the external component comprises a plurality of additional coils, wherein the plurality of additional coils are operable to transmit the second signal.

14. A system for detecting the orientation of an implant component, the system comprising:
  (a) an implantable component, wherein the implantable component is configured to be implanted within a patient;
  (b) an external component, wherein the external component is operable to communicate with at least a portion of the implantable component; and
  (c) a orientation detection component, wherein the orientation detection component is operable to determine an orientation of the implantable component relative to the external component, wherein the orientation detection component comprises an accelerometer or a tilt sensor, wherein the accelerometer or tilt sensor is positioned on or in the implantable component, wherein the accelerometer or tilt sensor comprises a member configured to move relative to the implantable component in accordance with the orientation of the implantable component.

15. The system of claim 14, wherein the implantable component comprises a first coil, wherein the external component comprises a second coil configured to communicate with the first coil.

16. The system of claim 1, wherein the first coil is operable to transmit a first signal having a phase, wherein the second coil is operable to transmit a second signal having a phase, and wherein the orientation detection component comprises a logic component operable to compare the phase of the first signal with the phase of the second signal, wherein the logic component is further configured to determine an orientation of the first coil relative to the second coil based on a comparison of the phase of the first signal with the phase of the second signal.

17. A method of detecting the orientation of an implanted component, the method comprising:
  (a) providing an external coil external to a patient, wherein the patient has an implanted component operable to transmit a first signal having a phase, wherein the implanted component has a center, wherein the external coil is operable to transmit a second signal having a phase;
  (b) positioning the external coil at a location approximately over the center of the implanted component;
  (c) receiving the first signal transmitted by the implanted component;
  (d) comparing the phase of the first signal with the phase of the second signal;
  (e) determining the orientation of the implanted component relative to the external coil, based on the comparison of the phase of the first signal and the phase of the second signal; and
  (f) moving the external coil within a region surrounding the location approximately over the center of the implanted component, wherein the act of determining the orientation of the implanted component relative to the external coil further comprises monitoring changes between the phase of the first signal and the phase of the second signal as the external coil is moved within the region.

* * * * *